(12) United States Patent
Vincent et al.

(10) Patent No.: US 12,012,561 B2
(45) Date of Patent: Jun. 18, 2024

(54) METHODS FOR CONVERTING C2+ OLEFINS TO HIGHER CARBON NUMBER OLEFINS

(71) Applicant: ExxonMobil Technology and Engineering Company, Annandale, NJ (US)

(72) Inventors: Matthew J. Vincent, Kingwood, TX (US); Keith H. Kuechler, Friendswood, TX (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 0 days.

(21) Appl. No.: 17/820,147

(22) Filed: Aug. 16, 2022

(65) Prior Publication Data

US 2022/0396534 A1    Dec. 15, 2022

Related U.S. Application Data

(60) Provisional application No. 63/362,565, filed on Apr. 6, 2022, provisional application No. 63/362,566, filed on Apr. 6, 2022.

(51) Int. Cl.
*C10G 69/12* (2006.01)
*B01D 3/14* (2006.01)
(Continued)

(52) U.S. Cl.
CPC ............. *C10G 69/126* (2013.01); *B01D 3/14* (2013.01); *B01D 3/143* (2013.01); *C07C 1/24* (2013.01);
(Continued)

(58) Field of Classification Search
None
See application file for complete search history.

(56) References Cited

U.S. PATENT DOCUMENTS 3,354,078 A    11/1967  Miale
4,016,218 A     4/1977  Haag et al.
(Continued)

FOREIGN PATENT DOCUMENTS

EP    0 882 692 A1    12/1998
EP    2123736 A1      11/2009
(Continued)

OTHER PUBLICATIONS

International Search Report and Written Opinion received for PCT Application No. PCT/US2023/017394, dated Jun. 23, 2023, 10 pages.

(Continued)

*Primary Examiner* — Ali Z Fadhel
(74) *Attorney, Agent, or Firm* — Shook, Hardy & Bacon L.L.P.

(57) ABSTRACT

A method for producing an isoolefinic stream may include: oligomerizing an ethylene stream to a C4+ olefin stream in a first olefin oligomerization unit comprising a serial reactor and a lights removal column, wherein the C4+ olefin stream contains no greater than 10 wt % of methane, ethylene, and ethane combined; and wherein the ethylene stream contains at least 50 wt % ethylene, at least 2000 wppm ethane, no greater than 1000 wppm of methane, and no greater than 20 wppm each of carbon monoxide and hydrogen; and oligomerizing the C4+ olefin stream and a propylene/C4+ olefin stream in a second oligomerization unit to produce the isoolefinic stream.

20 Claims, 9 Drawing Sheets

(51) Int. Cl.
| | |
|---|---|
| *C07C 1/24* | (2006.01) |
| *C07C 2/08* | (2006.01) |
| *C07C 2/12* | (2006.01) |
| *C07C 5/03* | (2006.01) |
| *C07C 7/04* | (2006.01) |
| *C07C 7/08* | (2006.01) |
| *C10L 1/08* | (2006.01) |

(52) U.S. Cl.
CPC ............... *C07C 2/08* (2013.01); *C07C 2/12* (2013.01); *C07C 5/03* (2013.01); *C07C 7/04* (2013.01); *C07C 7/08* (2013.01); *C10L 1/08* (2013.01); *C07C 2529/85* (2013.01); *C07C 2529/89* (2013.01); *C10G 2300/1092* (2013.01); *C10G 2300/301* (2013.01); *C10G 2400/08* (2013.01); *C10L 2270/04* (2013.01)

(56) References Cited

U.S. PATENT DOCUMENTS

| | | | | |
|---|---|---|---|---|
| 4,025,575 | A | | 5/1977 | Chang et al. |
| 4,677,243 | A | | 6/1987 | Kaiser |
| 4,777,316 | A | * | 10/1988 | Harandi ............... C07C 2/00 585/722 |
| 6,673,978 | B2 | | 1/2004 | Coute et al. |
| 7,667,086 | B2 | | 2/2010 | Kowalik et al. |
| 7,678,953 | B2 | | 3/2010 | Kuechler et al. |
| 7,692,049 | B2 | | 4/2010 | Kuechler et al. |
| 8,318,994 | B2 | | 11/2012 | Kowalik et al. |
| 2009/0000185 | A1 | | 1/2009 | Aulich et al. |
| 2011/0005190 | A1 | | 1/2011 | Bauldreay et al. |
| 2012/0197053 | A1 | | 8/2012 | Cantrell et al. |
| 2012/0271081 | A1 | * | 10/2012 | Nesterenko ............ B01J 29/40 585/315 |
| 2014/0051897 | A1 | | 2/2014 | Peters et al. |
| 2014/0275669 | A1 | | 9/2014 | Daage et al. |
| 2015/0247100 | A1 | | 9/2015 | Bradin |
| 2017/0306253 | A1 | | 10/2017 | Wrigley et al. |
| 2017/0369804 | A1 | * | 12/2017 | Lilga ............... C10G 29/205 |
| 2018/0230392 | A1 | | 8/2018 | Ginestra et al. |
| 2019/0093036 | A1 | | 3/2019 | Berkhous et al. |
| 2020/0056106 | A1 | * | 2/2020 | Deimund ............ B01J 29/7261 |
| 2021/0363446 | A1 | | 11/2021 | Kar et al. |
| 2021/0363449 | A1 | | 11/2021 | Rubin-Pitel et al. |
| 2022/0073830 | A1 | | 3/2022 | Harada et al. |

FOREIGN PATENT DOCUMENTS

| | | | |
|---|---|---|---|
| WO | 2004/016572 | A1 | 2/2004 |
| WO | 2004/018089 | A1 | 3/2004 |
| WO | 2017/187289 | A1 | 11/2017 |
| WO | 2022/063993 | A1 | 3/2022 |

OTHER PUBLICATIONS

Non-Final Office Action dated Nov. 9, 2023 in U.S. Appl. No. 17/820,152, 6 pages.
Dagle, V. L., et al., "Production and fuel properties of iso-olefins with controlled molecular structure and obtained from butene oligomerization", FUEL, vol. 277, pp. 1-7 (2020).
International Search Report and Written Opinion received for PCT Application No. PCT/US2023/017420, dated Jun. 21, 2023, 10 pages.
International Search Report and Written Opinion received for PCT Application No. PCT/US2023/017401, dated Jun. 22, 2023, 9 pages.
International Search Report and Written Opinion received for PCT Application No. PCT/US2023/017451, dated Jun. 30, 2023, 10 pages.
International Search Report and Written Opinion received for PCT Application No. PCT/US2023/017445, dated Jul. 4, 2023, 12 pages.
International Search Report and Written Opinion received for PCT Application No. PCT/US2023/017456, dated Jul. 5, 2023, 9 pages.
Forestière, A., et al., "Oligomerization of Monoolefins by Homogeneous Catalysts", Oil & Gas Science and Technology—Rev. IFP, vol. 64, No. 6, pp. 649-667 (2009).
Gülder, O. L., et al., "A Rapid Cetane Number Prediction Method for Petroleum Liquids and Pure Hydrocarbons Using Proton NMR", SAE Technical Paper Series (892073), International Fuels and Lubricants Meeting and Exposition, pp. 1-13 (Sep. 25-28, 1989).
Miale, J. N., et al., "Catalysis by Crystalline Aluminosilicates IV. Attainable Catalytic Cracking Rate Constants, and Superactivity", Journal of Catalysis, vol. 6, pp. 278-287 (1966).
Weisz, P. B., and Miale, J. N., "Superactive Crystalline Aluminosilicate Hydrocarbon Catalysts", Journal of Catalysis, vol. 4, pp. 527-529 (1965).
Non-Final Office Action dated Jun. 22, 2023 in U.S. Appl. No. 17/820,159, 6 pages.
Notice of Allowance received for U.S. Appl. No. 17/820,159, mailed on Jan. 24, 2024, 8 pages.
International Search Report and Written Opinion received for PCT Patent Application No. PCT/US2023/017441, mailed on Mar. 25, 2024, 11 pages.
Notice of Allowance received for U.S. Appl. No. 17/820,159, mailed on Mar. 13, 2024, 2 pages.

* cited by examiner

| | | | | |
|---|---|---|---|---|
| on aromatic rings | Ha | 0.17 | 0.13 | 0.17 | 0.15 |
| on olefinic carbons | Ho | 0.03 | 1.29 | 3.03 | 4.38 |
| alpha to aromatic rings | H(alpha) | 0.16 | 0.51 | 1.07 | 1.49 |
| beta to aromatic rings, naphthenic & paraffinic CH | Hc1 | 4.94 | 10.97 | 19.4 | 26.06 |
| paraffinic CH2, CH3 beta to and CH2>= gamma from aromatic ring | Hc2 | 43.3 | 38.8 | 32.59 | 27.69 |
| paraffinic CH3, CH3>=gamma from aromatic ring | Hd | 51.4 | 48.29 | 43.74 | 40.24 |
| | Cetane # | 48.8 | 43.8 | 36.3 | 30.8 |

| | | | | |
|---|---|---|---|---|
| CH/CH2 | 0.11 | 0.28 | 0.60 | 0.94 |
| CH/CH3 | 0.10 | 0.23 | 0.44 | 0.65 |
| CH2/CH3 | 0.84 | 0.80 | 0.75 | 0.69 |
| CH3/(CH2+CH) | 1.07 | 0.97 | 0.84 | 0.75 |
| CH3/CH2 | 1.19 | 1.24 | 1.34 | 1.45 |

FIG. 6

| Analysis | 100% JET-A1 | JET-A1 / 30% IPB-1 | JET-A1 / 70% IPB-1 | 100 % IPB-1 | JET-A1 passing value | JET-A1 Spec |
|---|---|---|---|---|---|---|
| Appearance | C&B | C&B | C&B | C&B | C&B | C&B[1] |
| Acidity, mg KOH/g | 0.010 | 0.010 | 0.010 | 0.015 | 0.015 max | D3242 |
| Aromatics, vol % | 17.1 | 17.0 | 8.3 | 0.245 mM[2] | 25.0 max | D1319 |
| Sulfur, total, wt.% | 0.0363 | 0.0255 | 0.0114 | <0.0010 | 0.30 max | D2622 |
| Naphthalenes, vol % | 1.98 | | | | 3.0 max | D1840 |
| Distillation, °C | - | - | - | - | - | D86 |
|    IBP | 160.1 | 164.3 | 171.1 | 176.2 | Report | " |
|    10% | 191.6 | 189.7 | 187.7 | 187.5 | 205 max | " |
|    20% | | | | | Report | " |
|    50% | 220.7 | 215.8 | 210.9 | 206.8 | Report | " |
|    90% | 251.8 | 253.4 | 257.8 | 265.3 | Report | " |
|    FBP | 269.4 | 281.8 | 293.3 | *303.9* | 300 max | " |
| Distill. Resid., vol % | 1.0 | 1.0 | 1.0 | 1.2 | 1.5 max | " |
| Distill. Loss, vol % | 0.6 | 0.3 | 0.8 | 1.2 | 1.5 max | " |
| Flash Pt., °C | 48.9 | 53.3 | 54.4 | 58.8 | 38 min | D56 |
| Density, kg/m$^3$ | 823.8 | 806.8 | 784.8 | *767.0* | 775 - 840 | D4052 |
| Freeze Pt., °C | -63.0 | -64.0 | -57.0 | -56.0 | -47 max | D2386 |
| Viscosity, -20 °C, cSt | 5.954 | 5.383 | 5.731 | 6.058 | 8.0 max | D445 |
| Heat of Comb, MJ/kg | 43.08 | 43.21 | 43.61 | 43.73 | 42.8 min | D3338 |
| Smoke Pt., mm | 22.0* | 28.0 | 39.0 | 45.0 | 25.0 min | D1322 |
| Copper Corrosion | 1a | 1a | 1a | 1a | 1 max | D130 |
| JFTOT breakpoint, °C | 270 | 270 | 285 | 295 | 260 min | D3241 |
| Ext gum mg/100mL | 2 | 1 | 2 | 2 | 7 max | D381 |
| Hydrogen Cont, wt % | 13.57 | 13.85 | 14.53 | 14.51 | 13.40 min | D3343 |
| MSEP | 96 | 93 | 96 | 100 | 90 min | D3948 |
| Electric Cond., pS/m | <1 | <1 | <1 | <1 | 150-450 | D2642 |
| Peroxides, mg/kg | | | | 0.9 | x | D3703 |
| Cetane Number | | | | 48.2 | x | D613 |
| | Items in BOLD & *Italics* do not meet JET-A1 specifications | | | | | |

1 – C&B refers to "clear and bright"

2 – This value determined according to M-1514

\* - Smoke point below 25 meets specification when the naphthalene content is less than 3.0 vol%

FIG. 7

| Analysis | 100% JET-A1 | JET-A1 / 30% IPB-2 | JET-A1 / 70% IPB-2 | 100 % IPB-2 | JET-A1 passing value | JET-A1 Spec |
|---|---|---|---|---|---|---|
| Appearance | C&B | C&B | C&B | C&B | C&B | C&B[1] |
| Acidity, mg KOH/g | 0.010 | 0.014 | 0.011 | 0.010 | 0.015 max | D3242 |
| Aromatics, vol % | 17.1 | 16.8 | 7.2 | | 25.0 max | D1319 |
| Sulfur, total, wt.% | 0.0363 | 0.0286 | 0.0114 | <0.0010 | 0.30 max | D2622 |
| Naphthalenes, vol % | 1.98 | 1.42 | | | 3.0 max | D1840 |
| Distillation, °C | - | - | - | - | - | D86 |
| | 160.1 | 155.4 | 151.1 | 151.9 | 176.2 | Report | " |
| | 191.6 | 177.9 | 169.3 | 164.6 | 187.5 | 205 max | " |
| | | | | | | Report | " |
| | 220.7 | 213.4 | 205.8 | 197.1 | 206.8 | Report | " |
| | 251.8 | 250.7 | 253.3 | 250.1 | 265.3 | Report | " |
| | 269.4 | 276.6 | 284.6 | 293.1 | *303.9* | 300 max | " |
| Distill. Resid., vol % | 1.0 | 1.3 | 1.0 | 1.1 | 1.5 max | " |
| Distill. Loss, vol % | 0.6 | 1.3 | 1.5 | 1.0 | 1.5 max | " |
| Flash Pt., °C | 48.9 | 47.8 | 45.6 | 43.3 | 38 min | D56 |
| Density, kg/m³ | 823.8 | 804.8 | 778.7 | *758.2* | 775 - 840 | D4052 |
| Freeze Pt., °C | -63.0 | -60.0 | -58.0 | -62.0 | -47 max | D2386 |
| Viscosity, -20 °C, cSt | 5.954 | 5.353 | 5.445 | 4.148 | 8.0 max | D445 |
| Heat of Comb, MJ/kg | 43.08 | 43.28 | 43.62 | 44.01 | 42.8 min | D3338 |
| Smoke Pt., mm | 22.0[3] | 23.0[3] | 40.0 | 41.0 | 25.0 min | D1322 |
| Copper Corrosion | 1a | 1a | 1a | 1a | 1 max | D130 |
| JFTOT breakpoint, °C | 270 | 275 | 285 | >315 | 260 min | D3241 |
| Ext gum mg/100mL | 2 | 2 | 1 | 1 | 7 max | D381 |
| Hydrogen Cont, wt % | 13.57 | 13.85 | 14.63 | 15.12 | 13.40 min | D3343 |
| MSEP | 96 | 97 | 96 | 99.0 | 90 min | D3948 |
| Electric Cond., pS/m | <1 | <1 | <1 | <1 | 150-450 | D2642 |
| Peroxides, mg/kg | | | | 0.6 | x | D3703 |
| Cetane Number | | | | 47.0 | x | D613 |
| Items in BOLD & *Italics* do not meet JET-A1 specifications | | | | | | |

FIG. 8

| | | | | | |
|---|---|---|---|---|---|
| on aromatic rings | Ha | 0.17 | 0.13 | 0.17 | 0.15 |
| on olefinic carbons | Ho | 0.03 | 1.29 | 3.03 | 4.38 |
| alpha to aromatic rings | H(alpha) | 0.16 | 0.51 | 1.07 | 1.49 |
| beta to aromatic rings, naphthenic & paraffinic CH | Hc1 | 4.94 | 10.97 | 19.4 | 26.06 |
| paraffinic CH2, CH3 beta to and CH2>= gamma from aromatic ring | Hc2 | 43.3 | 38.8 | 32.59 | 27.69 |
| paraffinic CH3, CH3>=gamma from aromatic ring | Hd | 51.4 | 48.29 | 43.74 | 40.24 |
| | Cetane # | 48.8 | 43.8 | 36.3 | 30.8 |

| | | | | |
|---|---|---|---|---|
| CH/CH2 | 0.11 | 0.28 | 0.60 | 0.94 |
| CH/CH3 | 0.10 | 0.23 | 0.44 | 0.65 |
| CH2/CH3 | 0.84 | 0.80 | 0.75 | 0.69 |
| CH3/(CH2+CH) | 1.07 | 0.97 | 0.84 | 0.75 |
| CH3/CH2 | 1.19 | 1.24 | 1.34 | 1.45 |

FIG. 9

METHODS FOR CONVERTING C2+ OLEFINS TO HIGHER CARBON NUMBER OLEFINS

CROSS REFERENCE TO RELATED APPLICATIONS

This application claims the benefit of U.S. Provisional Application Nos. 63/362,565 and 63/362,566, both filed on Apr. 6, 2022, the entire contents of each are incorporated herein by reference.

This application is related to two other co-pending U.S. applications U.S. Ser. Nos. 17/820,152 and 17/820,159 both filed on Aug. 16, 2022. These co-pending U.S. applications are hereby incorporated by reference herein in their entirety.

FIELD OF INVENTION

The present application relates to methods for converting C2+ olefins to higher carbon number olefins.

BACKGROUND

Olefins are valued feedstocks in chemical manufacturing. For example, light olefins like ethylene and propylene are useful in polymerization reactions. Higher carbon olefins like C6+ olefins and C8+ olefins, which may be produced by oligomerizing light olefins, are useful in producing specialty surfactants, lubricants, jet/aviation fuel, diesel fuel, fuel additives, and the like. Many oligomerization catalyst systems have been investigated for increasing the yield of preferred higher carbon olefins and with greater yields. However, the steps in upgrading light olefins to higher carbon olefins have remained reasonably unchanged.

SUMMARY OF INVENTION

The present application relates to methods for converting C2+ olefins to higher carbon number olefins.

A nonlimiting example method for producing an isoolefinic stream comprises: oligomerizing an ethylene stream to a C4+ olefin stream in a first olefin oligomerization unit comprising a serial reactor and a lights removal column, wherein the C4+ olefin stream contains no greater than 10 wt % of methane, ethylene, and ethane combined; and wherein the ethylene stream contains at least 50 wt % ethylene, at least 2000 wppm ethane, no greater than 1000 wppm of methane, and no greater than 20 wppm each of carbon monoxide and hydrogen; and oligomerizing the C4+ olefin stream and a propylene/C4+ olefin stream in a second oligomerization unit to produce the isoolefinic stream.

A nonlimiting example method of the present disclosure comprises: converting an oxygenate to olefins to produce a raw olefin stream; wherein the raw olefin stream comprises ethylene, propylene, and C4+ olefins, wherein at least 10 wt % of all olefins in the raw olefin stream are ethylene, and further containing at least 1000 wppm of each methane and ethane, and at least 100 wppm of each carbon monoxide and hydrogen; separating the raw olefin stream to remove hydrogen, carbon monoxide, propylene and C4+ olefins from the raw olefin stream, and produce an ethylene stream containing at least 50 wt % ethylene, at least 2000 wppm ethane, no greater than 1000 wppm of methane, and no greater than 20 wppm each of carbon monoxide and hydrogen, wherein at least 95 wt % of all the ethylene in the raw olefin stream is recovered in the ethylene stream; and oligomerizing at least a portion of the ethylene stream to convert at least 90% of the ethylene contained in the ethylene stream to a C4+ olefin stream containing no greater than 10 wt % of methane, ethylene, and ethane combined.

A nonlimiting example method for producing an isoolefinic stream comprises: providing a raw olefin stream comprising ethylene, propylene and C4+ olefins, wherein at least 10 wt % of all olefins in the raw olefin stream are ethylene, and further containing at least 1000 wppm of each methane and ethane, and at least 100 wppm of each carbon monoxide and hydrogen; separating the raw olefin stream to remove hydrogen, carbon monoxide, propylene and C4+ olefins from the raw olefin stream, and produce an ethylene stream containing at least 50 wt % ethylene, at least 2000 wppm ethane, no greater than 1000 wppm of methane, and no greater than 20 wppm each of carbon monoxide and hydrogen, wherein at least 95 wt % of all the ethylene in the raw olefin stream is recovered in the ethylene stream; oligomerizing at least a portion of the ethylene stream in a first olefin oligomerization unit comprising a serial reactor and a lights removal column, to convert in a single pass through the serial reactor(s) at least 90% of the ethylene contained in the ethylene stream to a C4+ olefin stream containing no greater than 10 wt % of methane, ethylene, and ethane combined; and oligomerizing at least a portion of each of the propylene and the C4+ olefins removed from the raw olefins stream, and at least a portion of the C4+ stream in a second olefin oligomerization unit comprising a serial reactor and a fractionation column to produce the isoolefinic stream.

These and other features and attributes of the disclosed methods of the present disclosure and their advantageous applications and/or uses will be apparent from the detailed description which follows.

BRIEF DESCRIPTION OF THE DRAWINGS

To assist those of ordinary skill in the relevant art in making and using the subject matter hereof, reference is made to the appended drawings. The following figures are included to illustrate certain aspects of the disclosure, and should not be viewed as exclusive configurations. The subject matter disclosed is capable of considerable modifications, alterations, combinations, and equivalents in form and function, as will occur to those skilled in the art and having the benefit of this disclosure.

FIG. 6 illustrates results from the $^1$H NMR analysis.

FIG. 7 illustrates compositional information for blends of an isoparaffinic blend component with a conventional jet fuel.

FIG. 8 illustrates compositional information for blends of another isoparaffinic blend component with a conventional jet fuel.

FIG. 9 illustrates results from $^1$H NMR characterization of isoolefinic and isoparaffinic blend components.

DETAILED DESCRIPTION

Figure 1:
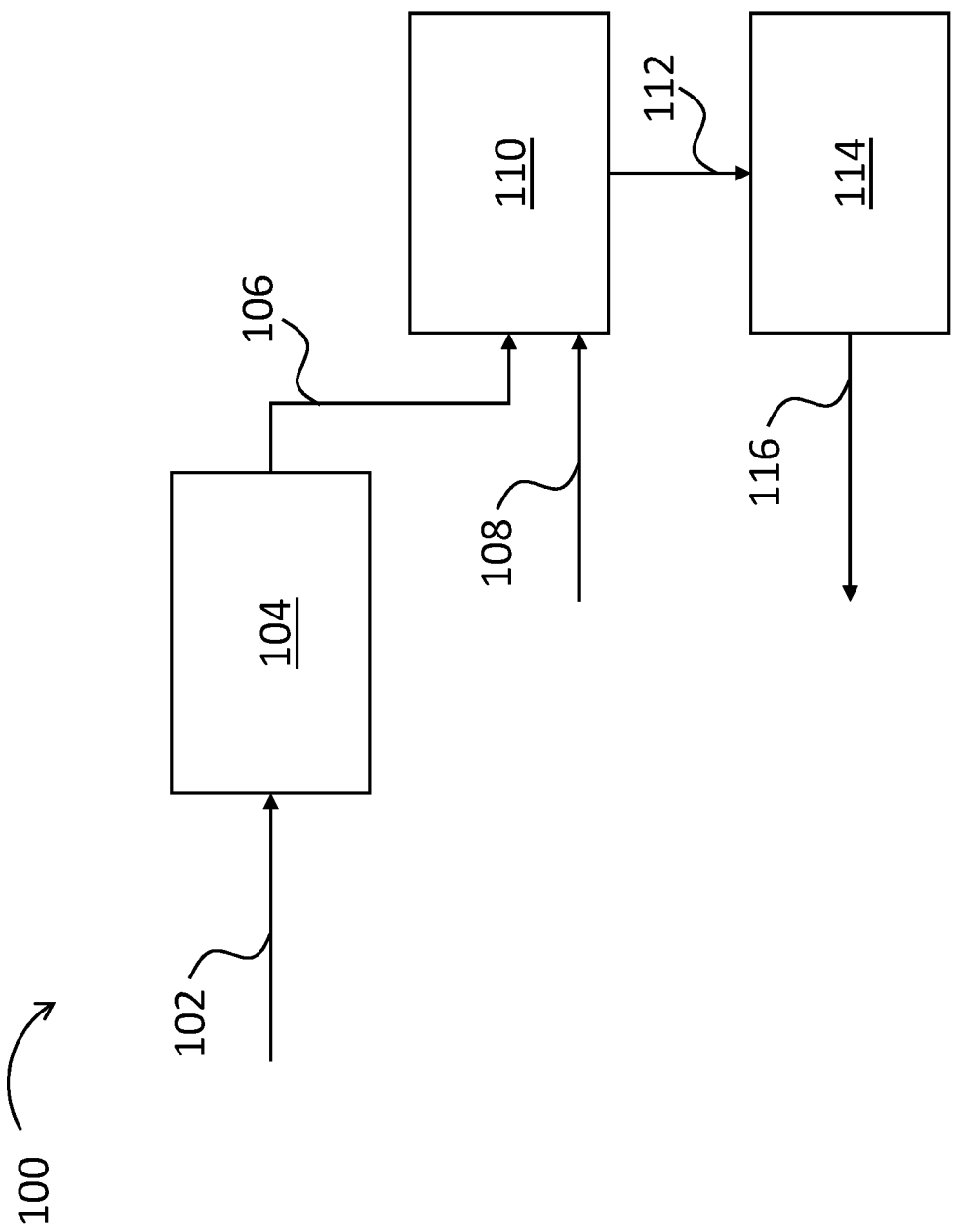
FIG. 1 illustrates a nonlimiting example of a method of the present disclosure.

The present application relates to methods for converting C2+ olefins to higher carbon number olefins. Said olefins and/or said olefins converted to paraffins may be useful for a variety of other applications including fuels and blendstocks for fuels. More specifically, the conversion may include two oligomerization processes that may advantageously improve the overall ethylene conversion while having flexibility and efficiencies that may provide energy and cost savings.

Definitions

All numerical values within the detailed description and the claims herein are modified by "about" or "approximately" the indicated value, and take into account experimental error and variations that would be expected by a person having ordinary skill in the art.

In this discussion, a jet fuel or jet fuel blend component that contains at least a portion of synthesized jet fuel boiling range compounds (i.e., jet boiling range compounds not derived from processing a mineral source) is defined as a synthetic jet fuel or synthetic jet fuel blending component.

In this discussion, if methanol is used as a feedstock for forming olefins, methanol obtained by a variety of processes may be referred to as "sustainable" methanol. Examples of such processes may include, but are not limited to, reforming municipal waste, reforming biomass, fermenting biomass, electrolyzing water to produce hydrogen for reaction with carbon monoxide and/or carbon dioxide, and the like, and any combination thereof.

Current commercial standards for jet fuels typically specify a variety of properties. Examples of property specifications and/or typical properties for commercial jet fuels include a total acidity of 0.1 mg KOH/g or less, or 0.015 mg KOH/g or less, a sulfur content of 3000 wppm or less, a freezing point maximum of −40° C. or −47° C., a viscosity at −20° C. of 8.0 cSt or less, a flash point of at least 38° C., an initial boiling point of 140° C. or more, a T10 distillation point of 205° C. or less, and/or a final boiling point of 300° C. or less. Another example of a property specification is a specification for a maximum deposit thickness on the surface of a heater tube and/or a maximum pressure increase during a thermal stability test at 260° C. (according to ASTM D3241), such as a maximum deposit thickness of 85 nm and/or a maximum pressure increase of 25 mm Hg. Still another example of a property specification can be a water separation rating, such as a water separation rating of 85 or more, as measured according to ASTM D3948. A water separation rating provides an indication of the amount of surfactant present in a jet fuel boiling range sample. Petroleum fractions that have an appropriate boiling range and that also satisfy the various requirements for a commercial standard can be tested (such as according to ASTM D3241) and certified for use as jet fuels. In some aspects, the kerosene boiling range fraction can correspond to a jet fuel fraction that satisfies the specification for a jet fuel under ASTM D1655. This can include a thermal stability breakpoint of 260° C. or more, or 275° C. or more, as defined by ASTM D3241.

Unless otherwise specified, distillation points and boiling points can be determined according to ASTM D2887 for distillates and ASTM D86 for kerosenes and jet fuel. For samples that are not susceptible to characterization using ASTM D2887, ASTM D7169 can be used. It is noted that still other methods of boiling point characterization may be provided in the examples. The values generated by such other methods are believed to be indicative of the values that would be obtained under ASTM D2887, ASTM D7169, and/or ASTM D86.

In this discussion, the distillate boiling range is defined as 140° C. to 370° C. A distillate boiling range fraction is defined as a fraction having a T10 distillation point of 170° C. or more and a T90 distillation point of 370° C. or less. The diesel boiling range is defined as 170° C. to 370° C. A diesel boiling range fraction is defined as a fraction having a T10 distillation point of 170° C. or more, a final boiling point of 300° C. or more, and a T90 distillation point of 370° C. or less. An atmospheric resid is defined as a bottoms fraction having a T10 distillation point of 149° C. or higher, or 350° C. or higher. The vacuum gas oil (VGO) boiling range is defined as 370° C. to 565° C. A vacuum gas oil boiling range fraction (also referred to as a heavy distillate) can have a T10 distillation point of 350° C. or higher and a T90 distillation point of 538° C. or less. A vacuum resid is defined as a bottoms fraction having a T10 distillation point of 500° C. or higher, or 538° C. or higher, or 565° C. or higher. It is noted that the definitions for distillate boiling range fraction, kerosene (or jet fuel) boiling range fraction, diesel boiling range fraction, atmospheric resid, and vacuum resid are based on boiling point only. Thus, a distillate boiling range fraction, diesel fraction, atmospheric resid fraction, vacuum gas oil fraction, and/or vacuum resid fraction can include components that did not pass through a distillation tower or other separation stage based on boiling point.

In this discussion, the jet fuel boiling range or kerosene boiling range is defined as 140° C. to 300° C. A jet fuel boiling range fraction or a kerosene boiling range fraction is defined as a fraction with a T10 distillation point of 140° C. to 205° C. or less, and a final boiling point of 300° C. or less. It is noted that jet fuel boiling range fractions can sometimes also have a flash point of 38° C. or higher, although kerosene boiling range fractions do not necessarily have such a requirement.

In this discussion, a hydroprocessed fraction refers to a hydrocarbon fraction and/or hydrocarbonaceous fraction that has been exposed to a catalyst having hydroprocessing activity in the presence of 300 kPa-a or more of hydrogen at a temperature of 200° C. or more. Examples of hydroprocessed fractions include hydroprocessed distillate fractions (i.e., a hydroprocessed fraction having the distillate boiling range), hydroprocessed kerosene fractions (i.e., a hydroprocessed fraction having the kerosene boiling range) and hydroprocessed diesel fractions (i.e., a hydroprocessed fraction having the diesel boiling range). It is noted that a hydroprocessed fraction derived from a biological source, such as hydrotreated vegetable oil, can correspond to a hydroprocessed distillate fraction, a hydroprocessed kerosene fraction, and/or a hydroprocessed diesel fraction, depending on the boiling range of the hydroprocessed fraction.

With regard to characterizing properties of diesel/distillate boiling range fractions and/or blends of such fractions with other components to form diesel boiling range fuels, a variety of methods can be used. Density of a blend at 15° C. (kg/m$^3$ or equivalently g/cm$^3$) can be determined according to ASTM D4052. Sulfur (in wppm or wt %) can be determined according to ASTM D2622, while nitrogen (in wppm or wt %) can be determined according to D4629. Pour point can be determined according to ASTM D5950. Cloud point can be determined according to D2500. Freeze point can be determined according to ASTM D5972. Cetane number can be determined according to ASTM D4737, procedure A. Kinematic viscosity can be determined according to ASTM D445. Aromatics content can be determined according to ASTM D1319. Flash point can be determined according to ASTM D56.

For various marine fuels, density (in kg/m³) can be determined according to ISO 3675. For marine fuel oils, sulfur (in wppm) can be determined according to ISO 8754. For marine fuel oils, kinematic viscosity at 50° C. (in cSt) can be determined according ISO 3104. For marine fuel oils, pour point can be determined according to ISO 3016. For marine fuel oils, sediment can be determined according to ISO 10307-2. CCAI (calculated carbon aromaticity index) can be determined according Equation F.1 in ISO 8217: 2012. Micro carbon residue content can be determined according to ASTM D4530. The content of n-heptane insolubles can be determined according to ASTM D3279. Flash point can be determined according to ASTM D93. The metals content can be determined according to ASTM D8056. Nitrogen can be determined according to D4629 for lower concentrations and D5762 for higher concentrations, as appropriate.

With regard to characterizing properties of kerosene/jet boiling range fractions and/or blends of such fractions with other components to form kerosene/jet boiling range fuels, a variety of methods can be used. Density of a blend at 15° C. (kg/m³) can be determined according to ASTM D4052. Sulfur (in wppm or wt %) can be determined according to ASTM D2622, while nitrogen (in wppm or wt %) can be determined according to D4629. Kinematic viscosity at either −20° C. or −40° C. (in cSt) can be determined according to ASTM D445. Pour point can be determined according to ASTM D5949. Cloud point can be determined according to D5773. Freeze point can be determined according to D5972. Flash point can be determined according to ASTM D56. Aromatics content can be determined according to ASTM D1319. Cetane number can be determined according to ASTM D613.

In this discussion, the content of n-paraffins, isoparaffins, cycloparaffins, aromatics, and/or olefins can be determined according to test method UOP 990. It is noted that for some of the paraffin, n-paraffin, and isoparaffin contents described below, the contents were determined using gas chromatography according to the Linear Paraffin method. The n-paraffin peaks from a hydrocarbon sample in gas chromatography are well known. The n-paraffin peaks can be separately integrated to determine the n-paraffin content of a sample using gas chromatography. The peaks in a GC spectrum between the n-paraffin peaks can be assigned to isoparaffins with the same carbon number as the lower peak, so that a total amount of paraffins having a given carbon number can be determined. The isoparaffin content for a given carbon number can be determined by subtracting the n-paraffin content from the total paraffin content. It is believed that the values herein determined by the Linear Paraffin method are representative of the values that would be obtained according to UOP 990.

As noted above, UOP 990 can be used to determine paraffin, naphthene, and aromatics content. It is noted that for some paraffin, naphthene, and/or aromatics contents described herein, supercritical fluid chromatography (SFC) was used. It is believed that the SFC characterization values are representative of what would be obtained according to UOP 990. For SFC characterization, the characterization was performed using a commercial supercritical fluid chromatograph system, and the methodology represents an expansion on the methodology described in ASTM D5186 to allow for separate characterization of paraffins and naphthenes. The expansion on the ASTM D5186 methodology was enabled by using additional separation columns, to allow for resolution of naphthenes and paraffins. The system was equipped with the following components: a high pressure pump for delivery of supercritical carbon dioxide mobile phase; temperature controlled column oven; autosampler with high pressure liquid injection valve for delivery of sample material into mobile phase; flame ionization detector; mobile phase splitter (low dead volume tee); back pressure regulator to keep the $CO_2$ in supercritical state; and a computer and data system for control of components and recording of data signal. For analysis, approximately 75 milligrams of sample was diluted in 2 milliliters of toluene and loaded in standard septum cap autosampler vials. The sample was introduced based via the high pressure sampling valve. The SFC separation was performed using multiple commercial silica packed columns (5 micron with either 60 or 30 angstrom pores) connected in series (250 mm in length either 2 mm or 4 mm ID). Column temperature was held typically at 35 or 40° C. For analysis, the head pressure of columns was typically 250 bar. Liquid $CO_2$ flow rates were typically 0.3 ml/minute for 2 mm ID columns or 2.0 ml/minute for 4 mm ID columns. The SFC FID signal was integrated into paraffin and naphthenic regions. In addition to characterizing aromatics according to ASTM D5186, a supercritical fluid chromatograph was used to analyze samples for split of total paraffins and total naphthenes. A variety of standards employing typical molecular types can be used to calibrate the paraffin/naphthene split for quantification.

As used herein, the term "paraffin" refers to saturated hydrocarbons that may be linear or branched. The paraffin may be straight-chain or branched-chain and is considered to be a non-ring compound. "Paraffin" is intended to embrace all structural isomeric forms of paraffins. The term "n-paraffin" has the expected definition of a straight chain alkane (no branches or rings in the carbon chain). The term "isoparaffin" is used herein to refer to any alkane that includes one or more branches in the carbon chain but does not include any ring structures. The term "paraffin" encompasses the terms "n-paraffin" and "isoparaffin."

In this discussion, the term "iso-olefin" is analogous to "isoparaffin", but refers to an alkene rather than an alkane. Thus, an iso-olefin is defined as an alkene that includes at least one branch in the carbon chain but that does not include a ring structure.

In this discussion, the term "naphthene" refers to a cycloalkane (also known as a cycloparaffin). Therefore, naphthenes correspond to saturated ring structures. The term naphthene encompasses single-ring naphthenes and multiring naphthenes. The multi-ring naphthenes may have two or more rings, e.g., two-rings, three-rings, four-rings, five-rings, six-rings, seven-rings, eight-rings, nine-rings, and ten-rings. The rings may be fused and/or bridged. The naphthene can also include various side chains, such as one or more alkyl side chains of 1-10 carbons.

In this discussion, the term "saturates" refers to all straight chain, branched, and cyclic paraffins. Thus, saturates correspond to a combination of paraffins and naphthenes.

In this discussion, the term "aromatic ring" means five or six atoms joined in a ring structure wherein (i) at least four of the atoms joined in the ring structure are carbon atoms and (ii) all of the carbon atoms joined in the ring structure are aromatic carbon atoms. Therefore, aromatic rings correspond to unsaturated ring structures. Aromatic carbons can be identified using, for example, $^{13}C$ Nuclear Magnetic Resonance. Aromatic rings having atoms attached to the ring (e.g., one or more heteroatoms, one or more carbon atoms, etc.) but which are not part of the ring structure are within the scope of the term "aromatic ring." Additionally, it is noted that ring structures that include one or more heteroatoms (such as sulfur, nitrogen, or oxygen) can correspond to an "aromatic ring" if the ring structure otherwise falls within the definition of an "aromatic ring".

In this discussion, the term "non-aromatic ring" means four or more carbon atoms joined in at least one ring structure wherein at least one of the four or more carbon atoms in the ring structure is not an aromatic carbon atom. Non-aromatic rings having atoms attached to the ring (e.g., one or more heteroatoms, one or more carbon atoms, etc.), but which are not part of the ring structure, are within the scope of the term "non-aromatic ring."

In this discussion, the term "aromatics" refers to all compounds that include at least one aromatic ring. Such compounds that include at least one aromatic ring include compounds that have one or more hydrocarbon substituents. It is noted that a compound including at least one aromatic ring and at least one non-aromatic ring falls within the definition of the term "aromatics".

It is noted that that some hydrocarbons present within a feed or product may fall outside of the definitions for paraffins, naphthenes, and aromatics. For example, any alkenes that are not part of an aromatic compound would fall outside of the above definitions. Similarly, non-aromatic compounds that include a heteroatom, such as sulfur, oxygen, or nitrogen, are not included in the definition of paraffins or naphthenes.

As used herein, the term "Cx hydrocarbon" or "Cx" indicates hydrocarbon molecules having the number of carbon atoms represented by the number "x". The term "Cx+ hydrocarbons" indicates those molecules noted above having the number of carbon atoms represented by the number "x" or greater. For example, "C17+ hydrocarbons" would include C17, C18, and higher carbon number hydrocarbons. Similarly "Cx− hydrocarbons" indicates those molecules noted above having the number of carbon atoms represented by the number "x" or fewer.

Methods and Compositions

FIG. 1 illustrates a nonlimiting example of a method 100 of the present disclosure. The illustrated method 100 includes a first oligomerization 104 and a second oligomerization 110 and, optionally, hydroprocessing 114. Briefly, an ethylene stream 102 undergoes the first oligomerization 104, which produces a C4+ olefin stream 106. The C4+ olefin stream 106 and a propylene/C4+ olefin stream 108 then undergo a second oligomerization 110. The second oligomerization 110 produces an isoolefinic stream 112. The isoolefinic stream 112 has many potential uses. In a non-limiting example, the isoolefinic stream 112 undergoes hydroprocessing 114 and produces an isoparaffinic stream 116.

The ethylene stream 102 may contain at least 50 wt % ethylene, at least 2000 wppm ethane, no greater than 1000 wppm of methane, and no greater than 20 wppm each of carbon monoxide and hydrogen (or (i) at least 50 wt % ethylene, at least 2000 wppm ethane, no greater than 1000 wppm of methane, and no greater than 5 wppm each of carbon monoxide and hydrogen, or (ii) at least 50 wt % ethylene, at least 2000 wppm ethane, no greater than 1000 wppm of methane, and no greater than 1 wppm each of carbon monoxide and hydrogen). The ethylene may be present in the ethylene stream 102 in an amount of at least 50 wt %, or at least 70 wt %, or at least 80 wt %, or 50 wt % to 99.9 wt %, or 50 wt % to 99 wt %, or 60 wt % to 95 wt %, or 70 wt % to 90 wt %. The ethane may be present in the ethylene stream 102 in an amount of at least 2000 wppm, or at least 5000 wppm, or at least 1 wt %, or at least 10 wt %, or at least 25 wt %, or at least 45 wt %, or 2000 wppm to 45 wt %, or 2000 wppm to 25 wt %, or 5000 wppm to 10 wt %. The methane may be present in the ethylene stream 102 in an amount of no greater than 1000 wppm, or no greater than 500 wppm, or no greater than 250 wppm, or 10 wppm to 1000 wppm, or 10 wppm to 250 wppm, or 100 wppm to 500 wppm, or 250 wppm to 1000 wppm. Each of carbon monoxide and hydrogen, individually, may be present in the ethylene stream 102 in an amount of no greater than 20 wppm, no greater than 5 wppm, no greater than 1 wppm, or no greater than 0.5 wppm, or no greater than 0.1 wppm, or 0.001 wppm to 20 wppm, or 0.001 wppm to 5 wppm, or 0.001 wppm to 1 wppm, or 0.001 wppm to 0.5 wppm.

The two oligomerizations have similar chemical reactions, but are not identical steps. The chemistries of these steps may be accomplished by very different processes. For example, the first oligomerization 104 may be achieved with high efficiency and efficacy in the liquid phase using a homogenous catalyst. In contrast, the second oligomerization 110 of higher molecular weight olefins, such as propylene and butenes, may be more efficiently and effectively carried out with a heterogeneous catalyst under conditions where some or all of the components are supercritical. By separately oligomerizing the ethylene to a higher molecular weight olefin (the first oligomerization 104), the resultant olefins may be included as a portion of the feedstock in the second oligomerization 110, thereby increasing the overall yield of the higher molecular weight olefins (e.g., C10+ olefins). That is, the feedstock for the second oligomerization 110 has minimal amounts of ethylene. Overall, the process may benefit from separately using (a) a first oligomerization catalyst specific to high yields of ethylene oligomerization and (b) second oligomerization catalysts that have high yields of distillate-range olefins from olefin feedstock that has minimal amounts of ethylene. Because the two oligomerizations are completed as separate processes (although said processes may be performed in different portions of the same vessel), the overall methods and systems may have higher yields of distillate-range olefins that may then be used to produce the isoparaffinic stream and additional fuel products (e.g., distillates, jet fuel, kerosene, and the like).

When the ethylene stream 102 undergoes the first oligomerization 104, at least 95% of the ethylene present in the ethylene stream 102 may be converted to a C4+ olefins (e.g., C4 olefins, C6 olefins, C8 olefins, and C10 olefins). The C4+ olefin stream 106 may contain no greater than 10 wt % of methane, ethylene, and ethane combined (or (i) no greater than 5 wt % of methane, ethylene, and ethane combined, or (ii) no greater than 2000 wppm of methane, ethylene, and ethane combined, or (iii) no greater than 1000 wppm of methane, ethylene, and ethane combined, or (iv) at least 10 wppm and no greater than 10 wt % (or 2000 wppm, or 1000 wppm) of methane, ethylene, and ethane combined). The C4+ olefins may be present in the C4+ olefin stream 106 in an amount of at least 99 wt %, or at least 99.5 wt %, or at least 99.999 wt %, or 99 wt % to 99.999 wt %.

Having a low amount of carbon monoxide and hydrogen in the ethylene stream 102 may allow for high conversion of the ethylene to C4+ olefins in the first oligomerization 104. For example, carbon monoxide and hydrogen may be deleterious to the catalyst system in the first oligomerization 104, especially if the first oligomerization 104 utilizes nickel. However, the first oligomerization 104 may be largely unaffected by saturated hydrocarbons like methane and ethane, which may allow for higher concentrations of saturated hydrocarbons.

The ethylene stream 102 may be from any suitable source including, but not limited to, ethylene derived from an ethanol dehydration reaction, a steam cracker, a fluidized catalytic cracker (FCC), a catalytic conversion reaction of methanol typically called "Methanol To Olefins (MTO)," and the like, and any combination of sources. Note that most MTO processes may also satisfactorily convert other alcohols like ethanol or butanol, and/or ethers like dimethyl ether (DME) or diethyl ether (DEE), typically in some proportion with methanol, to useful olefins with the same catalysts and equipment given minor adjustments for rates and/or concentrations of various reaction products and contaminants. Other oxygen-containing molecules such as ketones, aldehydes and esters may also be converted to olefins, but not desirably given that their relative hydrogen deficiency to alcohols also produces more carbonaceous coke on the catalysts. Nonetheless, minor quantities of the aforementioned oxygenates are produced by the MTO reaction as byproducts, recovered in some form and recycled back to the MTO reactor in combination with the main alcohol feed. Hence, a more generic term often used for these types of technologies is "oxygenates to olefins."

The first oligomerization 104 may occur in a first oligomerization unit, which may comprise one or more serial reactors, typically fixed bed adiabatic reactor(s) housing (or otherwise containing) the heterogenous oligomerization catalyst or a continuous stir tank reactor (CSTR) or pump-around piping system for housing a homogenous oligomierzation catalyst.

Examples of catalysts used in the first oligomerization 104 may include, but are not limited to, (a) homogenous catalysts including (a1) homogenous catalysts containing organic aluminum, nickel, titanium, and/or zirconium or (a2) Ziegler types where (a1) or (a2) may optionally include a ligand for activating the metal and may optionally include a solvent such as a hydrocarbon or ionic liquid cyclohexane; (b) heterogeneous catalysts such as (b1) solid phosphoric acid, (b2) microporous materials such as zeolites, for example, ZSM-5 catalyst, ZSM-57 catalyst, ZSM-22 catalyst, ZSM-48 catalyst, ZSM-12 catalyst, or (b3) silicoaluminophosphate (SAPO) molecular sieves; (c) the like; and (d) any mixture thereof.

The first oligomerization 104 may utilize a homogeneous organometallic catalyst. This may include, for example, nickel and other metal liganded catalysts as described in "Oligomerization of Monoolefins by Homogeneous Catalysts," A. Forestiére, et al., Oil & Gas Science and Technology—Rev. IFP, Vol. 64 (2009), No. 6, pp. 649-667. Limiting the concentration of C10+ olefins to minor amounts (e.g. no more than about 15 wt % of the total C4+ oligomer product) may be optimal for feeding the stream to the second oligomerization 110. This may be achieved using ethylene oligomerization processes offered for license by IFP (now Axens) called DIMERSOL-E®, and that offered for license by UOP called Linear-1®. The second oligomerization 110 may function acceptably well with C10+ olefins in the reactor system feed, but may function most efficiently with a relatively low concentration of those components. A C10+ molecule is already in the carbon number range of distillate products such as diesel and jet fuel, so the main benefit of feeding it to the second oligomerization 110 is to provide the molecule with an alkyl branch (through adding a lighter olefin) to decrease its freeze point, at the risk of increased deleterious cracking reactions to which higher carbon number olefins are susceptible.

Contact between the ethylene stream 102 and the first oligomerization catalyst may be under conditions suitable for oligomerizing ethylene. For example, the temperature may be about 25° C. to about 300° C. (or about 50° C. to about 200° C.). For example, the pressure may be about 100 psia to about 2000 psia (or about 200 psia to about 1200 psia, or about 250 psia to about 1000 psia).

The propylene/C4+ olefin stream 108 and the C4+ olefin stream 106 undergo the second oligomerization 110 (e.g., in a second oligomerization unit) to produce the isoolefinic stream 112. While illustrated as entering the second oligomerization 110 separately, the method may include mixing (or otherwise blending) the propylene/C4+ olefin stream 108 and the C4+ olefin stream 106 before undergoing the second oligomerization 110.

The second oligomerization 110 that produces the isoolefinic stream 112 may optionally utilize the process described in U.S. Pat. No. 7,692,049, which is incorporated by reference in its entirety.

The propylene/C4+ olefin stream 108 may contain any single C3 to C9 olefin or any mixture thereof in any proportion. The propylene/C4+ olefin stream 108 may contain at least 50 wt % C3+ olefins. The C3+ olefins may be present in the propylene/C4+ olefin stream 108 in an amount of at least 50 wt %, at least 60 wt %, or at least 70 wt %, or at least 80 wt %, or 50 wt % to 95 wt %, or 50 wt % to 80 wt %, or 60 wt % to 90 wt %, or 70 wt % to 90 wt %, or 80 wt % to 95 wt %. The distribution of carbon numbers for the C3+ olefins may vary based on the source of the propylene/C4+ olefin stream 108. For example, the propylene/C4+ olefin stream 108 may comprise at least 5 wt % propylene, at least 5 wt % C4 olefin, and C5+ olefins such that the C3+ olefin concentration is at least 50 wt % of the propylene/C4+ olefin stream 108. C3 olefins may be present in the propylene/C4+ olefin stream 108 in an amount of at least 5 wt %, at least 10 wt %, or at least 20 wt %, or at least 30 wt %, or at least 40 wt %, or 5 wt % to 80 wt %, or 5 wt % to 30 wt %, or 10 wt % to 50 wt %, or 25 wt % to 75 wt %, or 40 wt % to 80 wt % of the propylene/C4+ olefin stream 108. C4 olefins may be present in the propylene/C4+ olefin stream 108 in an amount of at least 5 wt %, at least 10 wt %, or at least 20 wt %, or at least 30 wt %, or at least 40 wt %, or 5 wt % to 80 wt %, or 5 wt % to 30 wt %, or 10 wt % to 50 wt %, or 25 wt % to 75 wt %, or 40 wt % to 80 wt % of the propylene/C4+ olefin stream 108. C5 olefins may be present in the propylene/C4+ olefin stream 108 in an amount of at least 5 wt %, at least 10 wt %, or at least 20 wt %, or at least 30 wt %, or at least 40 wt %, or 5 wt % to 80 wt %, or 5 wt % to 30 wt %, or 10 wt % to 50 wt %, or 25 wt % to 75 wt %, or 40 wt % to 80 wt % of the propylene/C4+ olefin stream 108. C6 olefins may be present in the propylene/C4+ olefin stream 108 in an amount of at least 5 wt %, at least 10 wt %, or at least 20 wt %, or at least 30 wt %, or at least 40 wt %, or 5 wt % to 80 wt %, or 5 wt % to 30 wt %, or 10 wt % to 50 wt %, or 25 wt % to 75 wt %, or 40 wt % to 80 wt % of the propylene/C4+ olefin stream 108. In a nonlimiting example, the propylene/C4+ olefin stream 108 may comprise propylene, at least 5 wt % C4 olefins, at least 40 wt % C5 olefins, and at least 10 wt % C6 olefins. In another nonlimiting example, the propylene/C4+ olefin stream 108 may comprise propylene, at least 20 wt % C4 olefins, at least 40 wt % C5 olefins, and at least 10 wt % C6 olefins. In yet another nonlimiting example, the propylene/C4+ olefin stream 108 may comprise propylene, at least 40 wt % C4 olefins, at least 40 wt % C5 olefins, and at least 10 wt % C6 olefins.

The propylene/C4+ olefin stream 108 may be from any suitable source including, but not limited to, C4+ byproducts derived from a propane dehydrogenation reactor, a butane dehydrogenation reactor, a steam cracker, a fluidized catalytic cracker (FCC), a catalytic conversion reaction of methanol typically called "Methanol To Olefins (MTO)," the like, and any combination of sources.

The second oligomerization 110 may occur in an oligomerization unit, which may comprise a fixed bed adiabatic reactor housing (or otherwise containing) the oligomerization catalyst or an isothermal tubular reactor housing (or otherwise containing) the oligomerization catalyst.

Examples of oligomerization catalysts that may be used in the second oligomerization 110 may include, but are not limited to, the zeolite families respectively comprising, MWW family (e.g., MCM-22), *BEA family (e.g., zeolite beta), FAU catalyst, MTW family (e.g., ZSM-12), TON family (e.g., ZSM-22), MTT family (e.g., ZSM-23), *MRE family (e.g., ZSM-48), MFS family (e.g., ZSM-57), SAPO molecular sieves, the like, and any mixture thereof.

Contacting the propylene/C4+ olefin stream 108 and the C4+ olefin stream 106 (introduced as a mixture or separately) with the second oligomerization catalyst may be under conditions suitable for oligomerizing olefins. For example, the temperature may be about 150° C. to about 300° C. (or about 150° C. to about 250° C., or about 200° C. to about 300° C.). For example, the pressure may be about 600 psia to about 2000 psia (or about 600 psia to about 1200 psia, or about 1000 psia to about 2000 psia).

The second oligomerization unit or a unit between the second oligomerization unit and the hydroprocessing unit may remove at least one light olefin (e.g., C3-C9 olefins, or C3 to C6 olefins, or C3 to C8 olefins) stream from the isoolefinic stream 112. Said light olefins may be recycled back as a portion of the feed to the oligomerization unit along with the propylene/C4+ olefin stream 108 and the C4+ olefin stream 106.

The second oligomerization 110 generates an isoolefinic stream 112. The composition of the isoolefinic stream 112 depends on, among other things, the conditions for the second oligomerization 110, the composition of the propylene/C4+ olefin stream 108, the composition of the C4+ olefin stream 106, and the catalyst.

The isoolefinic stream 112 may contain predominantly C6+ olefins (or C8+ olefins, or C9+ olefins). For example, the isoolefinic stream 112 may contain at least 50 wt % (or at least 60 wt %, or at least 70 wt %, or at least 80 wt %, or 50 wt % to 99 wt %, or 50 wt % to 80 wt %, or 60 wt % to 90 wt %, or 70 wt % to 90 wt %, or 80 wt % to 99 wt %, or 94 wt % to 99 wt %) C6+ olefins (e.g., C6 to C20 olefins) with no greater than 20 wt % C5− olefins (or no greater than 10 wt % C5− olefins, or no greater than 5 wt % C5− olefins). In another example, the isoolefinic stream 112 may contain at least 50 wt % (or at least 60 wt %, or at least 70 wt %, or at least 80 wt %, or 50 wt % to 99 wt %, or 50 wt % to 80 wt %, or 60 wt % to 90 wt %, or 70 wt % to 90 wt %, or 80 wt % to 99 wt %, or 94 wt % to 99 wt %) C8+ olefins (e.g., C8 to C20 olefins) with no greater than 20 wt % C7− olefins (or no greater than 10 wt % C7− olefins, or no greater than 5 wt % C7− olefins). In yet another example, the isoolefinic stream 112 may contain at least 50 wt % (or at least 60 wt %, or at least 70 wt %, or at least 80 wt %, or 50 wt % to 99 wt %, or 50 wt % to 80 wt %, or 60 wt % to 90 wt %, or 70 wt % to 90 wt %, or 80 wt % to 99 wt %, or 94 wt % to 99 wt %) C9+ olefins (e.g., C9 to C20 olefins) with no greater than 20 wt % C8− olefins (or no greater than 10 wt % C8− olefins, or no greater than 5 wt % C8− olefins).

At least 50 wt % (or at least 60 wt %, or at least 70 wt %, or at least 80 wt %, or 50 wt % to 99 wt %, or 50 wt % to 80 wt %, or 60 wt % to 90 wt %, or 70 wt % to 90 wt %, or 80 wt % to 99 wt %, or 94 wt % to 99 wt %) of the olefins in the isoolefinic stream 112 may be isoolefinic.

For example, 80 wt % or more of the isoolefinic stream 112, or 90 wt % or more, or 94 wt % or more, or 97 wt % or more, may be composed of C9 to C20 isoolefins. Further, 2.0 wt % to 25 wt % of the isoolefinic stream 112 may be composed of C9 olefins (e.g., C9 isoolefins), or 2.0 wt % to 15 wt %, or 5.0 wt % to 25 wt %, or 5.0 wt % to 15 wt %, or 2.0 wt % to 10 wt %. Further, 1.0 wt % to 15 wt % of the isoolefinic stream 112 may be composed of C17+ olefins (e.g., C17+ isoolefins), or 2.5 wt % to 15 wt %. In some aspects, 1.0 wt % to 15 wt % of the isoolefinic stream 112 may be composed of C17 and/or C18 olefins (e.g., C17 and/or C18 isoolefins), or 2.5 wt % to 15 wt %, or 1.0 wt % to 10 wt %, or 2.5 wt % to 10 wt %. Further, the isoolefinic stream 112 may contain 5.0 wt % or less of C19+ olefins (e.g., C19+ isoolefins), or 3.0 wt % or less, or 1.0 wt % or less, such as down to having substantially no content of C19+ hydrocarbons. Further, the isoolefinic stream 112 may include 5.0 wt % or less of C8− olefins, or 3.0 wt % or less, or 1.0 wt % or less, or 0.5 wt % or less, such as down to 0.1 wt % or possibly still lower (i.e., substantially no C8− olefins).

In another example, the isoolefinic stream 112 can contain 60 wt % to 90 wt % of C11 to C18 olefins (e.g., C11 to C18 isoolefins). Additionally or alternately, the isoolefinic stream 112 may contain 50 wt % to 75 wt % of C12 to C16 olefins (e.g., C12 to C16 isoolefins). This is particularly advantageous for being suitable for further processing (e.g., hydroprocessing) where the resultant product is flexible for use as an aviation or diesel fuel.

The isoolefinic stream 112 may contain a reduced or minimized amount of aromatics. This can correspond to containing 5.0 wt % or less of aromatics, or 3.0 wt % or less, or 1.0 wt % or less, or 0.5 wt % or less, or 0.1 wt % or less, such as down to having substantially no aromatics content.

The composition of the isoolefinic stream 112, or a portion or fraction thereof, may be a suitable product for use in a variety of applications or suitable for further processing to a suitable product for use in a variety of applications. For example, the isoolefinic stream 112 may be suitable for further processing to produce a blend composition (e.g., jet fuel blend stock, diesel fuel blend stock, distillate blend stock, kerosene blend stock, and the like), specialty chemicals (e.g., surfactants, lubricants, solvents, hydraulic and other working fluids, and the like), and the like. In a nonlimiting example, a portion or all of the isoolefinic stream 112 may be further subjected to hydroprocessing 114 to create the isoparaffinic stream 116 (preferably having no greater than 10 wt % olefin content).

Mild hydroprocessing can generally convert iso-olefins to isoparaffins with a reduced or minimized amount of reduction in the size of the carbon chains in a fraction. In addition to converting iso-olefins to isoparaffins, hydroprocessing of a kerosene fraction can also be used to remove sulfur, remove nitrogen, saturate olefins, saturate aromatics, and/or for other purposes.

During hydroprocessing, a feedstock that is partially or entirely composed of a jet fuel boiling range fraction is treated in a hydrotreatment (or other hydroprocessing) reactor that includes one or more hydrotreatment stages or beds. Optionally, the reaction conditions in the hydrotreatment stage(s) can be conditions suitable for reducing the sulfur content of the feedstream, such as conditions suitable for reducing the sulfur content of the feedstream to 500 wppm or less, or 100 wppm or less, or 10 wppm or less, such as down to 0.5 wppm or possibly still lower. The reaction conditions can include an LHSV of 0.1 to 20.0 hr$^{-1}$, a hydrogen partial pressure from about 50 psig (0.34 MPag) to about 3000 psig (20.7 MPag), a treat gas containing at least about 50% hydrogen, and a temperature of from about 450° F. (232° C.) to about 800° F. (427° C.). Preferably, the reaction conditions include an LHSV of from about 0.3 to about 5 hr$^{-1}$, a hydrogen partial pressure from about 100 psig (0.69 MPag) to about 1000 psig (6.9 MPag), and a temperature of from about 700° F. (371° C.) to about 750° F. (399° C.).

Optionally, a hydrotreatment reactor can be used that operates at relatively low total pressure values, such as total pressures of about 200 psig (1.4 MPag) to about 800 psig (5.5 MPag). For example, the pressure in a stage in the hydrotreatment reactor can be at least about 200 psig (1.4 MPag), or at least about 300 psig (2.1 MPag), or at least about 400 psig (2.8 MPag), or at least about 450 psig (3.1 MPag). The pressure in a stage in the hydrotreatment reactor can be about 800 psig (5.5 MPag) or less, or about 700 psig (4.8 MPag) or less, or about 600 psig (4.1 MPa) or less.

The catalyst in a hydrotreatment stage can be a conventional hydrotreating catalyst, such as a catalyst composed of a Group VIB metal and/or a Group VIII metal on a support. Suitable metals include cobalt, nickel, molybdenum, tungsten, or combinations thereof. Preferred combinations of metals include nickel and molybdenum or nickel, cobalt, and molybdenum. Suitable supports include silica, silica-alumina, alumina, and titania.

The isoparaffinic stream 116 resulting from hydroprocessing 114 may be suitable for creating blend compositions (e.g., jet fuel blend stock, diesel fuel blend stock, distillate blend stock, kerosene blend stock, and the like). Advantageously, the isoolefinic stream 112 and the resultant isoparaffinic stream 116 may have a low aromatic content, which may be advantageous for producing low aromatic content fuels (e.g. jet fuels, jet fuel blend stocks).

The isoparaffinic stream 116 may have a similar carbon number distribution to the isoolefinic stream 112 but as paraffins rather than olefins. Therefore, the isoparaffinic stream 116 may contain predominantly C6+ isoparaffins (or C8+ isoparaffins, or C9+ isoparaffins). For example, the isoparaffinic stream 116 may contain at least 50 wt % (or at least 60 wt %, or at least 70 wt %, or at least 80 wt %, or 50 wt % to 99 wt %, or 50 wt % to 80 wt %, or 60 wt % to 90 wt %, or 70 wt % to 90 wt %, or 80 wt % to 99 wt %, or 94 wt % to 99 wt %) C6+ paraffins (e.g., C6 to C20 paraffins) with no greater than 20 wt % C5− paraffins (or no greater than 10 wt % C5− paraffins, or no greater than 5 wt % C5− paraffins). In another example, the isoparaffinic stream 116 may contain at least 50 wt % (or at least 60 wt %, or at least 70 wt %, or at least 80 wt %, or 50 wt % to 99 wt %, or 50 wt % to 80 wt %, or 60 wt % to 90 wt %, or 70 wt % to 90 wt %, or 80 wt % to 99 wt %, or 94 wt % to 99 wt %) C8+ paraffins (e.g., C8 to C20 paraffins) with no greater than 20 wt % C7− paraffins (or no greater than 10 wt % C7− paraffins, or no greater than 5 wt % C7− paraffins). In yet another example, the isoparaffinic stream 116 may contain at least 50 wt % (or at least 60 wt %, or at least 70 wt %, or at least 80 wt %, or 50 wt % to 99 wt %, or 50 wt % to 80 wt %, or 60 wt % to 90 wt %, or 70 wt % to 90 wt %, or 80 wt % to 99 wt %, or 94 wt % to 99 wt %) C9+ paraffins (e.g., C9 to C20 paraffins) with no greater than 20 wt % C8− paraffins (or no greater than 10 wt % C8− paraffins, or no greater than 5 wt % C8− paraffins).

At least 50 wt % (or at least 60 wt %, or at least 70 wt %, or at least 80 wt %, or 50 wt % to 99 wt %, or 50 wt % to 80 wt %, or 60 wt % to 90 wt %, or 70 wt % to 90 wt %, or 80 wt % to 99 wt %, or 94 wt % to 99 wt %) of the paraffins in the isoparaffinic stream 116 may be isoparaffinic.

For example, 80 wt % or more of the isoparaffinic stream 116, or 90 wt % or more, or 94 wt % or more, or 97 wt % or more, may be composed of C9 to C20 isoparaffins. Further, 2.0 wt % to 25 wt % of the isoparaffinic stream 116 may be composed of C9 paraffins (e.g., C9 isoparaffins), or 2.0 wt % to 15 wt %, or 5.0 wt % to 25 wt %, or 5.0 wt % to 15 wt %, or 2.0 wt % to 10 wt %. Further, 1.0 wt % to 15 wt % of the isoparaffinic stream 116 may be composed of C17+ paraffins (e.g., C17+ isoparaffins), or 2.5 wt % to 15 wt %. In some aspects, 1.0 wt % to 15 wt % of the isoparaffinic stream 116 may be composed of C17 and/or C18 paraffins (e.g., C17 and/or C18 isoparaffins), or 2.5 wt % to 15 wt %, or 1.0 wt % to 10 wt %, or 2.5 wt % to 10 wt %. Further, the isoparaffinic stream 116 may contain 5.0 wt % or less of C19+ paraffins (e.g., C19+ isoparaffins), or 3.0 wt % or less, or 1.0 wt % or less, such as down to having substantially no content of C19+ hydrocarbons. Further, the isoparaffinic stream 116 may include 5.0 wt % or less of C8− paraffins, or 3.0 wt % or less, or 1.0 wt % or less, or 0.5 wt % or less, such as down to 0.1 wt % or possibly still lower (i.e., substantially no C8− paraffins).

In another example, the isoparaffinic stream 116 can contain 60 wt % to 90 wt % of C11 to C18 paraffins (e.g., C11 to C18 isoparaffins). Additionally or alternately, the isoparaffinic stream 116 may contain 50 wt % to 75 wt % of C12 to C16 paraffins (e.g., C12 to C16 isoparaffins). This is particularly advantageous for being suitable for further processing (e.g., hydroprocessing) where the resultant product is flexible for use as an aviation or diesel fuel.

The isoparaffinic stream 116 may contain a reduced or minimized amount of aromatics. This can correspond to containing 5.0 wt % or less of aromatics, or 3.0 wt % or less, or 1.0 wt % or less, or 0.5 wt % or less, or 0.1 wt % or less, such as down to having substantially no aromatics content.

Figure 2:
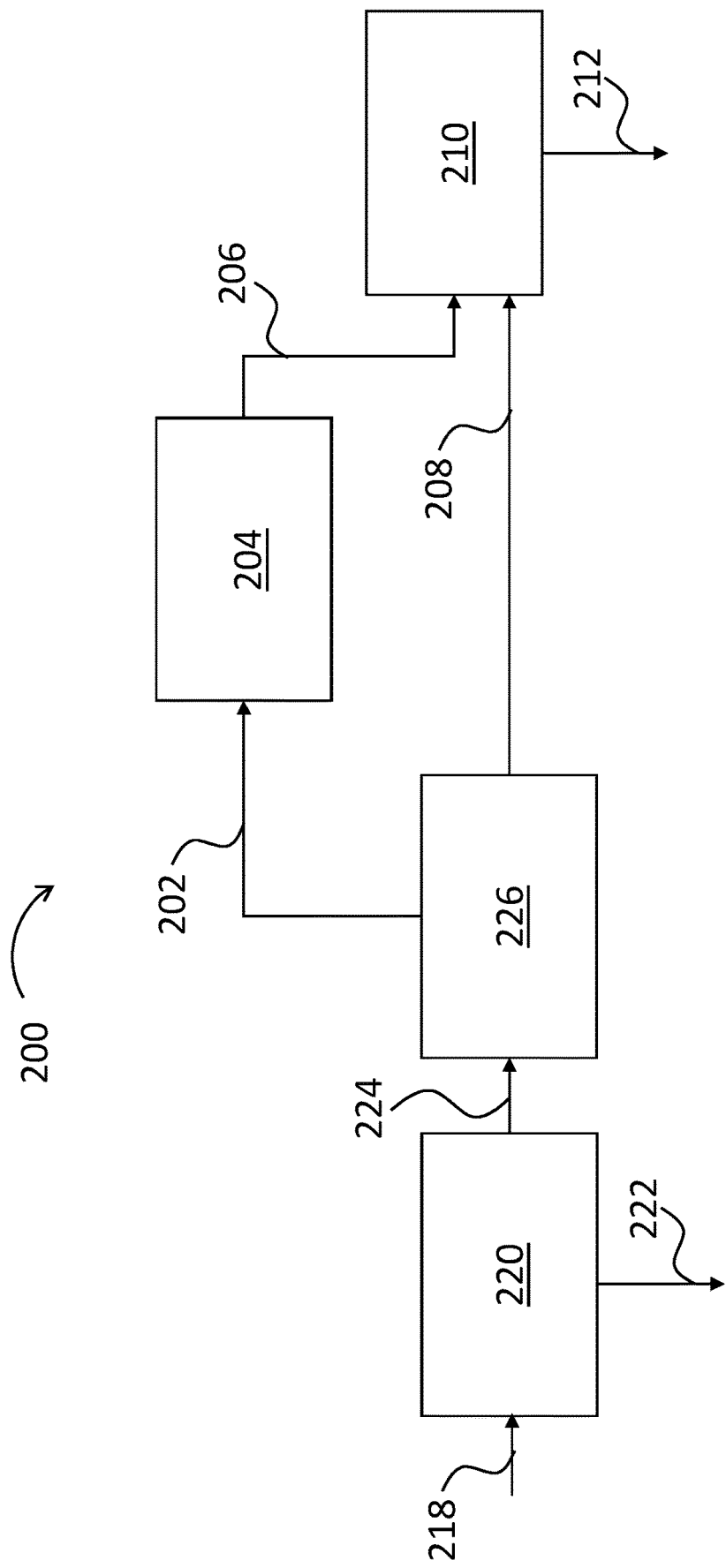
FIG. 2 illustrates a nonlimiting example of a method of the present disclosure.

While the description of FIG. 1 provides nonlimiting examples of sources for the ethylene stream 102 and the propylene/C4+ olefin stream 108, FIG. 1 does not illustrate said sources. FIG. 2 illustrates a nonlimiting example that includes a process for converting an oxygenate to olefin then separating of the olefin product to yield potential sources for both the ethylene stream and the propylene/C4+ olefin stream.

FIG. 2 illustrates a nonlimiting example method 200 of the present disclosure showing an oxygenate to olefin reaction 220, followed by separation 226 of the product from the oxygenate to olefin process 220, a first oligomerization 204, and a second oligomerization 210. Briefly, an oxygenate stream 218 (e.g., comprising methanol and, optionally, dimethyl ether) undergoes an oxygenate to olefin reaction 220, which produces a water stream 222 and a raw olefin stream 224.

The raw olefin stream 224 then undergoes separation 226 into an ethylene stream 202 and a propylene/C4+ olefin stream 208. The ethylene stream 202 then undergoes a first oligomerization 204 to yield a C4+ olefin stream 206. The propylene/C4+ olefin stream 208 and C4+ olefin stream 206 may then be used in a variety of applications. In the illustrated example, the propylene/C4+ olefin stream 208 and C4+ olefin stream 206 are inputs for a second oligomerization 210 to produce an isoolefinic stream 212. In alternative embodiments, the second oligomerization may be excluded, and the propylene/C4+ olefin stream 208 and C4+ olefin stream 206 may be used as feeds for other processes.

The oxygenate stream 218 may be from any suitable source. In nonlimiting examples, the oxygenate (e.g., methanol) may be produced from reforming natural gas, reforming coal, reforming municipal waste, reforming biomass, fermenting biomass, electrolyzing water to produce hydrogen for reaction with carbon monoxide and/or carbon dioxide, and the like, and any combination thereof. Generally, electrolyzing water produces hydrogen and oxygen. The hydrogen may then be reacted with carbon monoxide and/or carbon dioxide to produce methanol.

Examples of methanol conversion catalysts that may be utilized in the oxygenate to olefin reaction 220 may include, but are not limited to, microporous materials, such as zeolites, SAPOs and ALPO materials. Such materials may include, but are not limited to, the zeolite families respectively comprising, MWW family (e.g., MCM-22), *BEA family (e.g., zeolite beta), ZSM-11, (MEL) family (e.g., ZSM-12), TON family (e.g., ZSM-22), MTT family (e.g., ZSM-23), *MRE family (e.g., ZSM-48), MFS family (e.g., ZSM-57), ZSM-5 (MFI), ALPO-18 (AEI) and SAPO-34 (CHA) or their mixtures (including intergrowths).

Contact of the oxygenate stream 218 with the methanol conversion catalyst may be under conditions suitable for producing olefins. For example, the inlet temperature may be about 300° C. to about 625° C. (or about 400° C. to about 600° C., or about 450° C. to about 550° C.). For example, the pressure may be about 20 psia to about 300 psia (or about 30 psia to about 250 psia, or about 50 psia to about 150 psia).

The oxygenate to olefin reaction 220 may occur in a fixed bed adiabatic reactor that houses (or otherwise containing) the methanol conversion catalyst and accepts an input of a oxygenate stream 218.

A resulting raw olefin stream 224 may comprise ethylene, propylene, and C4+ olefins, wherein at least 10 wt % of all olefins in the stream may be ethylene. The raw olefin stream 224 may further comprise at least 1000 wppm each of methane and ethane, and at least 100 wppm each of carbon monoxide and hydrogen. In other aspects, the raw olefin stream 224 may include other components within the volatility range from hydrogen to butanes, such as propane or dimethyl ether. The exact composition of the raw olefin stream 224 will depend on the specific method of producing the raw olefin stream 224, and further on the specific means of operating those methods.

The raw olefin stream 224 may have been treated (e.g., in a unit in which the oxygenate to olefin reaction 220 occurs or downstream thereof) by various methods to remove some of the byproducts generated by a given method of producing olefins. Such methods and related systems may be employed on the raw olefin stream 224 within the scope of the present disclosure, but are not shown in FIG. 2. Examples of such methods may include, but are not limited to, reactor effluent quenching and bulk water removal, gas compression, washing with a caustic solution to remove carbon dioxide, gas drying to bone dry, separation of C5+ species from C4 species, or selective saturation with hydrogen to remove acetylene and methylacetylene, among others well documented in the art. The present disclosure may be readily adapted by one skilled in the art to use the raw olefin stream 224 derived from a wide range of olefin production processes. It may also be useful to combine olefin streams from different sources or processes. In a nonlimiting example, ethylene derived from an ethanol dehydration reaction may be combined with hydrogen, CO, propylene, unreacted propane and C4+ byproducts derived from a propane dehydrogenation reaction to create the raw olefin stream 224.

The raw olefin stream 224 then undergoes separation 226 to produce the ethylene stream 202 and the propylene/C4+ olefin stream 208. The separation 226 may occur in a separation system. Examples of separation apparatuses that may be included in the separation system may include, but are not limited to, fractionators, membranes, the like, and any combination thereof.

The separation 226 may occur in the same unit as the oxygenate to olefin reaction 220 or in a downstream unit.

The separation 226 involves differences in component volatility using equipment such as flash drums and distillation columns, which may be configured in a number of ways to create an ethylene stream 202 that exits the separation 226. From the raw olefin stream 224, hydrogen, carbon monoxide, propylene, and C4+ olefins may be separated out to produce the ethylene stream 202. The ethylene stream 202 may contain at least 50 wt % ethylene, at least 2000 wppm ethane, no greater than 1000 wppm of methane, and no greater than 20 wppm each of carbon monoxide and hydrogen (or (i) at least 50 wt % ethylene, at least 2000 wppm ethane, no greater than 1000 wppm of methane, and no greater than 5 wppm each of carbon monoxide and hydrogen, or (ii) at least 50 wt % ethylene, at least 2000 wppm ethane, no greater than 1000 wppm of methane, and no greater than 1 wppm each of carbon monoxide and hydrogen), and at least 95 wt % of all the ethylene in the raw olefin stream 224 may be recovered in the ethylene stream 202. The ethylene stream 202 may also contain at least 90% of the ethane present in the raw olefin stream 224. Separation 226 creates a separate line for the lower volatility components separated from the ethylene and ethane in the ethylene stream 202, such as propylene and C4+ olefins, which exits the separation as propylene/C4+ olefin stream 208. The separation process may also include membrane and absorption systems instead of or in addition to distillation towers. The compositional description of ethylene stream 102 of FIG. 1 applies to the ethylene stream 202 of FIG. 2.

FIG. 2 illustrates the propylene/C4+ olefin stream 208 after the separation 226 as a single stream, but the propylene/C4+ olefin stream 208 may be two separate streams (e.g., a first stream comprising relatively pure propylene and a second stream comprising relatively pure C4+ olefin). This additional separation may be performed with additional distillation columns, and may include separation of propylene from propane and components of similar or lower volatility like dimethyl ether. This process, known in the art as a "Propylene Concentrator," is particularly useful if the source of olefins is oxygenate conversion that can make significant amounts of dimethyl ether, or catalytic cracking that can make significant amounts of propane, both of which are not particularly desirable to provide to the optional second oligomerization 210.

The disclosure of FIG. 1 for the ethylene stream 102, the first oligomerization 104, the C4+ olefin stream 106, the propylene/C4+ olefin stream 108, the second oligomerization 110, and isoolefinic stream 112 apply to the ethylene stream 202, the first oligomerization 204, the C4+ olefin stream 206, the propylene/C4+ olefin stream 208, the second oligomerization 210, and isoolefinic stream 212 of FIG. 2. Further embodiments may include further processing isoolefinic stream 212 as discussed relative to the further processing of isoolefinic stream 112 including hydroprocessing to produce an isoparaffinic stream.

Figure 3:
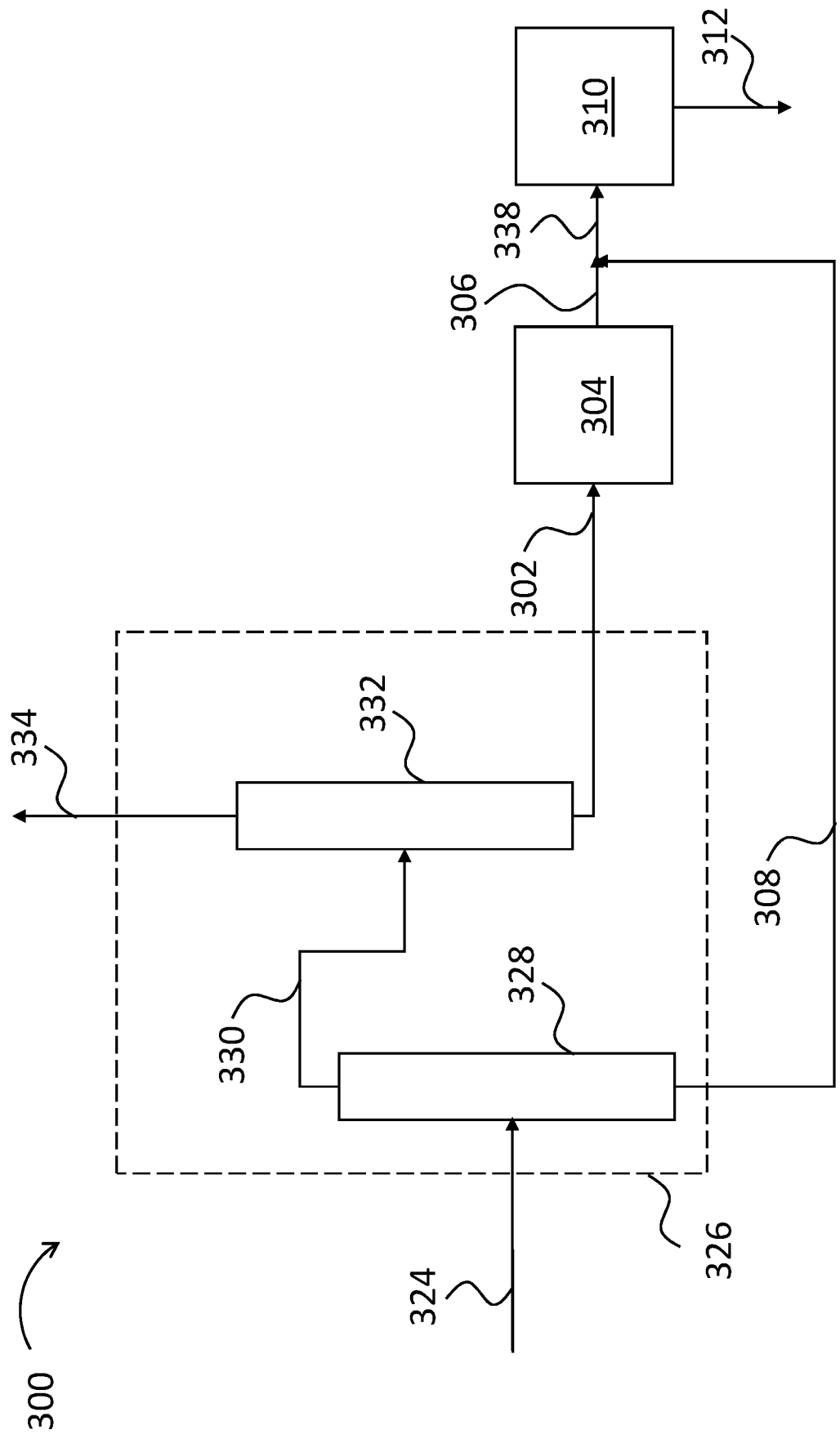
FIG. 3 illustrates a nonlimiting example of a method of the present disclosure.

FIG. 3 illustrates a nonlimiting example of a method 300 of the present disclosure where a nonlimiting example separation 326 is described. The disclosure relating to steps, streams, processes, units, etc. with reference numbers with the final two numbers corresponding to a foregoing reference number in FIG. 1 and/or FIG. 2 (e.g., propylene/C4+ olefin stream 108) applies to the corresponding steps, streams, processes, units, etc. having reference numbers with the same final two numbers in FIG. 3 (e.g., propylene/C4+ olefin stream 308). However, the separation 326 illustrated in FIG. 3 is a nonlimiting example of a separation and is one of many possible separations that may be used in separations shown in any of the other FIGS. in the present disclosure.

As illustrated, a raw olefin stream 324 undergoes separation 326 to remove hydrogen, carbon monoxide, propylene and C4+ olefins from the ethylene and ethane. Briefly, the separation 326 creates three separate streams where (1) the higher volatility components (e.g., methane, hydrogen, and carbon monoxide) form a high volatility stream 334, (2) the lower volatility components (e.g., propylene and C4+ olefins) form a propylene/C4+ olefin stream 308, and (3) the intermediate volatility components (e.g., ethylene and ethane) form the ethylene stream 302.

In the separation 326, the raw olefin stream 324 is first introduced to a deethanizer distillation column 328 that separates the lower volatility components (e.g., propylene and C4+ olefins) from the higher and intermediate volatility components (e.g., ethylene, ethane, methane, carbon monoxide, and hydrogen) to yield the propylene/C4+ olefin stream 308 and a first overhead stream 330, respectively. The first overhead stream 330 is then directed to a demethanizer distillation column 332 to separate the higher volatility components from the intermediate volatility components to yield the high volatility stream 334 and the ethylene stream 302. The ethylene stream 302 may contain at least 50 wt % ethylene, at least 2000 wppm ethane, no greater than 1000 wppm of methane, and no greater than 20 wppm each of carbon monoxide and hydrogen (or (i) at least 50 wt % ethylene, at least 2000 wppm ethane, no greater than 1000 wppm of methane, and no greater than 5 wppm each of carbon monoxide and hydrogen, or (ii) at least 50 wt % ethylene, at least 2000 wppm ethane, no greater than 1000 wppm of methane, and no greater than 1 wppm each of carbon monoxide and hydrogen), and at least 95 wt % of all the ethylene in the raw olefin stream 324 may be recovered in the ethylene stream 302. In this embodiment, the ethylene stream 302 may also contain at least 90% of the ethane present in the raw olefin stream in line 324, which eliminates the need for a distillation column serving to separate ethylene from ethane (known in the art as a "C2 Splitter").

The ethylene stream 302 then undergoes a first oligomerization 304, which produces a C4+ olefin stream 306. The C4+ olefin stream 306 and the propylene/C4+ olefin stream 308 are then used as feed in the second oligomerization 310. As illustrated, the C4+ olefin stream 306 combines with the propylene/C4+ olefin stream 308 into a feed stream 338, which undergoes the second oligomerization 310. The second oligomerization 310 generates the desired isoolefinic stream 312. Further, embodiments may include further processing isoolefinic stream 312 as discussed relative to the further processing of isoolefinic stream 112 including hydroprocessing to produce an isoparaffinic stream.

Figure 4:
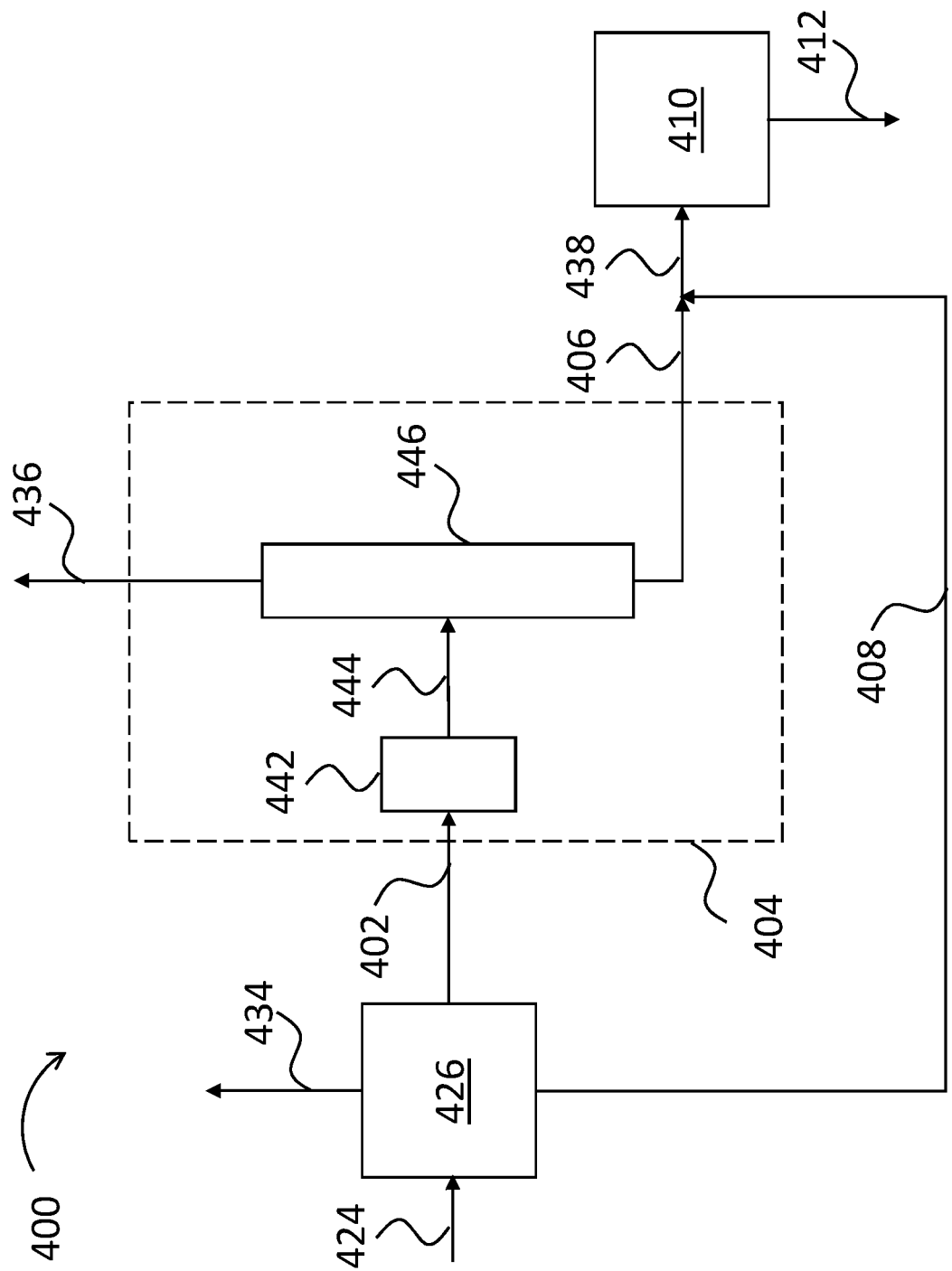
FIG. 4 illustrates a nonlimiting example of a method of the present disclosure.

FIG. 4 illustrates a nonlimiting example of a method 400 of the present disclosure where a nonlimiting example first oligomerization 404 is described. The disclosure relating to steps, streams, processes, units, etc. with reference numbers with the final two numbers corresponding to a foregoing reference number in FIG. 1, FIG. 2, and/or FIG. 3 (e.g., propylene/C4+ olefin stream 108) applies to the corresponding steps, streams, processes, units, etc. having reference numbers with the same final two numbers in FIG. 3 (e.g., propylene/C4+ olefin stream 308). However, the first oligomerization 404 illustrated in FIG. 4 is a nonlimiting example of a separation and is one of many possible separations that may be used in separations shown in any of the other FIGS. in the present disclosure.

Briefly, the raw olefin stream 424 undergoes a separation 426 to create at least two streams: an ethylene stream 402 and a propylene/C4+ olefin stream 408, and, optionally, a high volatility stream 434 (for example, when the separation 426 occurs according to the separation 326 of FIG. 3). The ethylene stream 402 then undergoes a first oligomerization 404, which may convert at least 95% of the ethylene present in the ethylene stream 402 to a C4+ olefin stream 406. The C4+ olefin stream 406 may contain no greater than 10 wt % of methane, ethylene, and ethane combined (or (i) no greater than 5 wt % of methane, ethylene, and ethane combined, or (ii) no greater than 2000 wppm of methane, ethylene, and ethane combined). The C4+ olefin stream 406 and the propylene/C4+ olefin stream 408 then undergo a second oligomerization 410. While optional, as illustrated, said streams 406 and 408 are combined into feed stream 438 before the second oligomerization 410 to yield an isoolefinic stream 412. Further embodiments may include further processing isoolefinic stream 412 as discussed relative to the further processing of isoolefinic stream 112 including hydroprocessing to produce an isoparaffinic stream.

The process of the first oligomerization 404 may include introducing the ethylene stream 402 into a reactor 442 where an oligomerization reaction of the ethylene stream 402 to an intermediate C4+ olefin stream 444 occurs. Said oligomerization may convert at least 95% of that ethylene in the ethylene stream 402 to C4+ oligomers in one pass through the reactor 442. A first oligomerization unit may include two or more reactors arranged in series, with the hydrocarbon product from one reactor, including some product oligomers and unreacted ethylene, sent as feed to the next reactor in the series to convert additional ethylene to the oligomer product. Alternatively, a first oligomerization unit may include two or more reactors arranged in parallel, for example, splitting the feed into two streams to two separate reactors, increasing the overall capacity of first oligomerization unit. Further, a hybrid of the foregoing with some reactors arranged in parallel and others in series may be included in a first oligomerization unit.

The intermediate C4+ olefin stream 444 from the reactor 442 is then introduced to a lights removal column 446 to remove components with volatility higher than butenes, and potentially a minor amount of butenes as well, to generate a light fuel gas stream 436. The higher volatility components in the light fuel gas stream 436 may include mainly methane, ethane, and unreacted ethylene. The separation of saturated hydrocarbons like methane and ethane from the intermediate C4+ olefin stream 444 using the lights removal column 446 may advantageously be less energy intensive and/or require less complicated components than if the saturated hydrocarbons were separated from closer volatility ethylene in the earlier separation 426. That is, the upstream separation may produce only two streams where the higher volatility components remain present in the ethylene stream. Then, said higher volatility components may be removed at the first oligomerization by inclusion of a lights removal column downstream of the oligomerization reactor. Said lights removal column may be within the first oligomerization unit or downstream thereof.

Another advantage of including a lights removal column downstream of the reactor 442 is that the first oligomerization reaction and first oligomerization catalyst may be largely unaffected by the saturated hydrocarbons, as the saturated hydrocarbons are essentially inert in the first oligomerization reaction. Therefore, the requirements for separating the saturated hydrocarbons in separation 426 can be relaxed or eliminated, which has significant energy use benefits and cost benefits.

Figure 5:
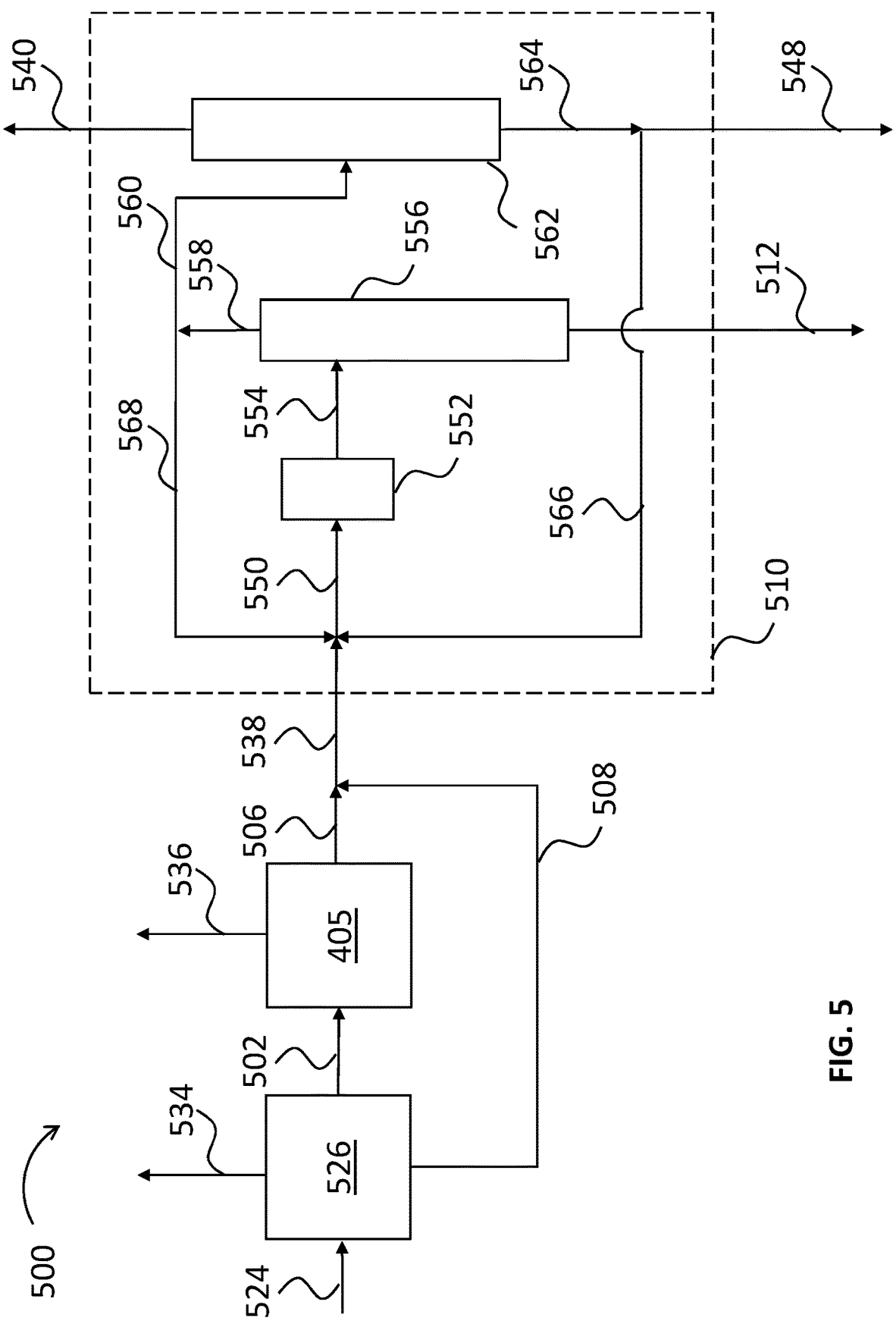
FIG. 5 illustrates a nonlimiting example of a method of the present disclosure.

FIG. 5 illustrates a nonlimiting example of a method 500 of the present disclosure where a nonlimiting example second oligomerization 510 is described. The disclosure relating to steps, streams, processes, units, etc. with reference numbers with the final two numbers corresponding to a foregoing reference number in FIG. 1, FIG. 2, FIG. 3, and/or FIG. 4 (e.g., propylene/C4+ olefin stream 108) applies to the corresponding steps, streams, processes, units, etc. having reference numbers with the same final two numbers in FIG. 3 (e.g., propylene/C4+ olefin stream 308). However, the second oligomerization 510 illustrated in FIG. 5 is a nonlimiting example of a separation and is one of many possible separations that may be used in separations shown in any of the other FIGS. in the present disclosure.

As illustrated, a raw olefin stream 524 enters a separation 526, which produces an ethylene stream 502, and a propylene/C4+ olefin stream 508, and, optionally, a high volatility stream 534 (for example, when the separation 526 occurs according to the separation 326 of FIG. 3). The ethylene stream 502 undergoes a first oligomerization 504 and separation, which produces a C4+ olefin stream 506 and, optionally, a light fuel gas stream 436 (for example, when a lights removal column is used, the first oligomerization 504 may occur according to the first oligomerization 404 of FIG. 4).

The C4+ olefin stream 506 and the propylene/C4+ olefin stream 508 then undergo a second oligomerization 510. While optional, as illustrated, said streams 506 and 508 are combined into feed stream 538 before the second oligomerization 510 to yield an isoolefinic stream 512.

The second oligomerization 510 is illustrated as being conducted in a second oligomerization unit that comprises a reactor 552, a mogas/distillate fractionation column 556, and a debutanizer fractionation column 562.

The feed stream 538 joins with a top recycle stream 568 and a bottom recycle stream 566 to form a combined second oligomerization reactor feed stream 550 comprising C4-C10+ olefins that may contain no greater than about 10 wt % C10+ olefins. Combined feed stream 550 is provided to reactor 552 that generates a reactor product 554 rich in distillate range C10+ olefins (e.g., C10+ isoolefins), along with unreacted and newly made C4-C9 olefins of various isomers.

The reactor product 554 is directed to the mogas/distillate fractionation column 556 that separates a C9− or C10− first mogas stream 558 from a C10+ isoolefin stream 512. The C10+ isoolefin stream 512 is removed from second oligomerization unit 510 and can be used for a variety of applications. The C9− first mogas stream 558 is split into two streams, typically with the majority becoming the top recycle stream 568 and the rest becoming a debutanizer feed stream 560. The debutanizer feed stream 560 is sent to a debutanizer fractionation column 562 that separates a C4− purge stream 540 from a C5+ second mogas stream 564. The C4− purge stream 540 is removed from second oligomerization unit 510 while the C5+ second mogas stream 564 is split into two streams, typically with the majority becoming the bottom recycle stream 566 and the rest becoming a mogas product purge stream 548 that is also removed from second oligomerization unit 510.

As described above, the propylene/C4+ olefin stream 508 and the C4+ olefin stream 506 may be separately introduced to the reactor 552. In variations within the scope of the present disclosure, depending on the exact compositions involved, including olefins and potential small concentration contaminants, it may be desirable to provide each of the streams 506 and 508 to separate points within second oligomerization unit 510. For example, the C4+ olefin stream 508 may contain up to 15 wt % or even greater of C10+ olefins that are already in the distillate range. To minimize the load on reactor 552, the propylene/C4+ olefin stream 508 can be a feed gas for reactor 552 and the C4+ olefin stream 506 can be added directly to the mogas/distillate fractionation column 556. In this manner, the mogas/distillate fractionation column 556 will separate the C10+ molecules in the C4+ olefin stream 506 directly into the isoolefin stream 512, and separate the lower carbon number molecules in the C4+ olefin stream 506 into the mogas range material 558, the great majority of which will become a recycle feed to the reactor 552 to produce additional isoolefin stream 512.

Further embodiments may include further processing isoolefinic stream 512 as discussed relative to the further processing of isoolefinic stream 112 including hydroprocessing to produce an isoparaffinic stream.

Isoparaffinic Blend Component for Blended Diesel Boiling Range and Marine Fuel Products In various aspects, an isoparaffinic blend component (e.g., all or a portion of an isoparaffinic stream discussed in FIGS. 1-5) and/or isoolefinic blend component (e.g., all or a portion of an isoolefinic stream discussed in FIGS. 1-5) can be used to form blended products that can correspond to distillate fuels and/or distillate fuel blending components. In this discussion, to be either an isoparaffinic blend component or an isoolefinic blend component, a fraction will contain 50 wt % or more of a combined weight of isoparaffins and iso-olefins, or 60 wt % or more, or 70 wt % or more, or 80 wt % or more, such as up to the fraction substantially being composed of isoparaffins and iso-olefins (i.e., less than 5.0 wt % of other types of hydrocarbons/compounds, or less than 3.0 wt %, or less than 1.0 wt %, such as down to zero).

In addition to the above, an isoparaffinic blend component refers to a fraction containing less than 5.0 wt % iso-olefins and 80 wt % or more of isoparaffins (relative to the weight of the fraction), or 85 wt % or more, or 90 wt % or more, such as up to having substantially all of the fraction correspond to isoparaffins. An isoolefinic blend component refers to a fraction that a) satisfies the requirement for the combined amount of iso-olefins and isoparaffins, and b) contains 5.0 wt % or more of iso-olefins, or 25 wt % or more, or 50 wt % or more, or 70 wt % or more, such as up to having substantially all of the fraction correspond to iso-olefins.

In various aspects, an isoparaffinic blend component and/or an isoolefinic blend component can have one or more of the following properties. In some aspects, 80 wt % or more of the blend component, or 90 wt % or more, or 94 wt % or more, or 97 wt % or more, is composed of $C_9$ to $C_{20}$ iso-olefins, isoparaffins, or a combination thereof. In some aspects, 2.0 wt % to 25 wt % of the blend component is composed of $C_9$ hydrocarbons, or 2.0 wt % to 15 wt %, or 5.0 wt % to 25 wt %, or 5.0 wt % to 15 wt %, or 2.0 wt % to 10 wt %. In some aspects, 1.0 wt % to 15 wt % of the blend component is composed of $C_{17+}$ hydrocarbons, or 2.5 wt % to 15 wt %. In some aspects, 1.0 wt % to 15 wt % of the blend component is composed of $C_{17}$ and/or $C_{18}$ hydrocarbons, or 2.5 wt % to 15 wt %, or 1.0 wt % to 10 wt %, or 2.5 wt % to 10 wt %. In some aspects, the blend component can contain 5.0 wt % or less of $C_{19+}$ hydrocarbons, or 3.0 wt % or less, or 1.0 wt % or less, such as down to having substantially no content of $C_{19+}$ hydrocarbons. In some aspects, the blend component can include 5.0 wt % or less of $C_{8-}$ hydrocarbons, or 3.0 wt % or less, or 1.0 wt % or less, or 0.5 wt % or less, such as down to 0.1 wt % or possibly still lower (i.e., substantially no $C_{8-}$ content). In some aspects, the blend component has a specific gravity at 15° C. of 0.730 $g/cm^3$ to 0.775 $g/cm^3$.

In some aspects, the blend component can contain 60 wt % to 90 wt % of $C_{11}$ to $C_{18}$ isoparaffins, iso-olefins, or a combination thereof, based on the weight of the blend component. Additionally or alternately, the blend component can contain 50 wt % to 75 wt % of $C_{12}$ to $C_{16}$ isoparaffins, iso-olefins, or a combination thereof based on the weight of the blend component. Having high amounts of larger isoparaffins can be beneficial for diesel fuel and/or diesel fuel blend component applications. Having higher amounts of larger isoparaffins/iso-olefins can be beneficial for marine fuel or marine fuel blend component applications.

In various aspects, the blend component can contain a reduced or minimized amount of aromatics. This can correspond to containing 5.0 wt % or less of aromatics, or 3.0 wt % or less, or 1.0 wt % or less, or 0.5 wt % or less, or 0.1 wt % or less, such as down to having substantially no aromatics content.

In various aspects, the blend component can have a flash point of 38° C. or higher, or 40° C. or higher, or 45° C. or higher, or 50° C. or higher, or 55° C. or higher, such as up to 60° C. or possibly still higher. Additionally or alternately, the blend component can have a cetane rating of 46.0 to 51.0, or 47.0 to 51.0, or 48.0 to 51.0. Further additionally or alternately, the blend component can have a kinematic viscosity at 40° C. of 1.9 cSt to 3.0 cSt, or 2.0 cSt to 3.0 cSt, or 2.2 cSt to 3.0 cSt, or 1.9 cSt to 2.8 cSt, or 2.0 cSt to 2.8 cSt, or 2.2 cSt to 2.8 cSt. Still further additionally or alternately, the blend component can have a cloud point of −50° C. or less, or −60° C. or less, such as down to −100° C. or possibly still lower.

In some aspects, the blend component, prior to adding any additives, can have an electrical conductivity of 10 pS/m or less (according to ASTM Test Method D2624), such as down to having substantially no electrical conductivity. It is noted that an isoparaffinic blend component as described herein has a good response to conductivity additives. After addition of conventional additives for conductivity, an isoparaffinic blend component can have a conductivity of 50 pS/m to 600 pS/m.

An isoparaffinic blend component and/or isoolefinic blend component can be blended with one or more other fractions to form a diesel boiling range product. Examples of fractions that can be blended with an isoparaffinic blend component and/or isoolefinic blend component include, but are not limited to, conventional diesel fractions, mineral diesel boiling range fractions, and various types of synthetic diesel boiling range fractions, such as hydrotreated vegetable oil, biodiesel (e.g., derived from processing of fatty acid methyl esters), other bio-derived diesel fractions, and/or Fischer-Tropsch fractions. Other challenged fractions where at least a portion of the fraction corresponds to diesel boiling range components can also be blended with an isoparaffinic blend component and/or isoolefinic blend component.

In various aspects, a blended product can contain 1.0 vol % or more of an isoparaffinic blend component, or 10 vol % or more, or 20 vol % or more, or 30 vol % or more, or 40 vol % or more, or 60 vol % or more, or 75 vol % or more, such as up to 99 vol % or possibly still higher. In some aspects, such a blended product can include 1.0 vol % to 50 vol % of an isoparaffinic blend component, or 1.0 vol % to 10 vol %, or 1.0 vol % to 30 vol %, or 10 vol % to 50 vol %, or 10 vol % to 30 vol %, or 30 vol % to 50 vol %. In other aspects, such a blended product can include 1.0 vol % to 99 vol % of an isoparaffinic blend component, or 1.0 vol % to 95 vol %, or 1.0 vol % to 70 vol %, or 1.0 vol % to 50 vol %, or 10 vol % to 99 vol %, or 10 vol % to 95 vol %, or 10 vol % to 70 vol %, or 10 vol % to 50 vol %, or 30 vol % to 99 vol %, or 30 vol % to 95 vol %, or 30 vol % to 70 vol %, or 30 vol % to 50 vol %, or 50 vol % to 99 vol %, or 50 vol % to 95 vol %, or 50 vol % to 70 vol %, or 70 vol % to 99 vol %.

Additionally or alternately, in various aspects, a blended product can contain 1.0 vol % or more of an isoparaffinic blend component, or 10 vol % or more, or 20 vol % or more, or 30 vol % or more, or 40 vol % or more, or 60 vol % or more, or 75 vol % or more, such as up to 99 vol % or possibly still higher. In some aspects, such a blended product can include 1.0 vol % to 50 vol % of an isoparaffinic blend component, or 1.0 vol % to 10 vol %, or 1.0 vol % to 30 vol %, or 10 vol % to 50 vol %, or 10 vol % to 30 vol %, or 30 vol % to 50 vol %. In other aspects, such a blended product can include 1.0 vol % to 99 vol % of an isoparaffinic blend component, or 1.0 vol % to 95 vol %, or 1.0 vol % to 70 vol %, or 1.0 vol % to 50 vol %, or 10 vol % to 99 vol %, or 10 vol % to 95 vol %, or 10 vol % to 70 vol %, or 10 vol % to 50 vol %, or 30 vol % to 99 vol %, or 30 vol % to 95 vol %, or 30 vol % to 70 vol %, or 30 vol % to 50 vol %, or 50 vol % to 99 vol %, or 50 vol % to 95 vol %, or 50 vol % to 70 vol %, or 70 vol % to 99 vol %.

In some aspects, the resulting blended product can include an unexpectedly high content of $C_{12-}$ isoparaffins and/or iso-olefins. In such aspects, the resulting blended product can contain 6.0 wt % or more of $C_{12-}$ isoparaffins and/or iso-olefins, or 10 wt % or more, or 15 wt % or more, 20 wt % or more, such as up to 40 wt % or possibly still higher. Additionally or alternately, in some aspects, the resulting blended product can include an unexpectedly high content of $C_{12}$ isoparaffins and/or iso-olefins. In such aspects, the resulting blended product can include 6.0 wt % or more of $C_{12}$ isoparaffins and/or iso-olefins, or 10 wt % or more, such as up to 20 wt % or possibly still higher.

In some aspects, the resulting blended product can have an unexpectedly high content of $C_9$ hydrocarbons. In such aspects, the resulting blended product can contain 5.0 wt % or more of $C_9$ hydrocarbons, or 10 wt % or more, or 15 wt % or more, such as up to 25 wt % or possibly still higher.

In various aspects, the resulting blended product can have a density at 15° C. of 0.760 $g/cm^3$ to 0.840 $g/cm^3$. In aspects where the blended product includes less than 50 vol % of conventional and/or mineral diesel fractions, the density at 15° C. can be 0.760 $g/cm^3$ to 0.825 $g/cm^3$, or 0.760 $g/cm^3$ to 0.810 $g/cm^3$, or 0.760 $g/cm^3$ to 0.800 $g/cm^3$, or 0.775 $g/cm^3$ to 0.825 $g/cm^3$, or 0.775 $g/cm^3$ to 0.810 $g/cm^3$, or 0.775 $g/cm^3$ to 0.800 $g/cm^3$, or 0.790 $g/cm^3$ to 0.825 $g/cm^3$. In aspects where the blended product includes 50 vol % or more of a conventional and/or mineral diesel fraction, the density at 15° C. can be 0.790 $g/cm^3$ to 0.840 $g/cm^3$, or 0.800 $g/cm^3$ to 0.840 $g/cm^3$, or 0.815 $g/cm^3$ to 0.840 $g/cm^3$, or 0.790 $g/cm^3$ to 0.825 $g/cm^3$, or 0.800 $g/cm^3$ to 0.825 $g/cm^3$.

Additionally or alternately, the resulting blended product can have a flash point of 40° C. or higher, or 50° C. or higher, or 60° C. or higher, such as up to 120° C. or possibly still higher.

In some aspects, when an isoparaffinic blend component and/or an isoolefinic blend component is blended with a conventional diesel boiling range fraction and/or a mineral diesel boiling range fraction, the cetane number of the resulting blend can be lower than the cetane number of the conventional diesel boiling range fraction and/or the mineral diesel boiling range fraction. In some aspects, when an isoparaffinic blend component and/or an isoolefinic blend component is blended with a bio-derived diesel boiling range fraction (e.g., biodiesel, hydrotreated vegetable oil, diesel derived from fatty acid methyl ester), the cetane number of the resulting blend can be lower than the cetane number of the bio-derived diesel boiling range fraction. In some aspects, the cetane number of the resulting blend can be 54.0 or less, or 53.0 or less, such as down to 52.0, or down to 50.0.

In various aspects, an isoparaffinic blend component and/or isoolefinic blend component can have favorable cold flow properties relative to other types of blend components. In some aspects where at least 20 vol % (or at least 40 vol %, or at least 60 vol %, such as up to 80 vol %) of an isoparaffinic blend component and/or isoolefinic blend component is blended with at least 20 vol % (or at least 40 vol %, or at least 60 vol %, such as up to 80 vol %) of conventional/mineral diesel boiling range component, the cloud point of the resulting blend can be lower than the cloud point of the conventional/mineral diesel boiling range fraction by 10° C. or more, or 15° C. or more, or 20° C. or more, such as up to 60° C. or possibly still more. In some aspects where at least 20 vol % (or at least 40 vol %, or at least 60 vol %, such as up to 80 vol %) of an isoparaffinic blend component and/or isoolefinic blend component is blended with at least 20 vol % (or at least 40 vol %, or at least 60 vol %, such as up to 80 vol %) of synthetic diesel boiling range component, the cloud point of the resulting blend can be lower than the cloud point of the synthetic diesel boiling range fraction by 10° C. or more, or 15° C. or more, or 20° C. or more, such as up to 60° C. lower or possibly still more.

In various aspects, the resulting blended product can have a kinematic viscosity at 40° C. of 2.0 to 3.5, or 2.0 to 3.2, or 2.0 to 2.8, or 2.0 to 2.4, or 2.0 to 2.2, or 2.2 to 3.5, or 2.2 to 3.2, or 2.2 to 2.8, or 2.2 to 2.4.

In some aspects, the resulting blended product can contain a reduced or minimized amount of aromatics. This can correspond to containing 15 wt % or less of aromatics, or 10 wt % or less, or 5.0 wt % or less, or 3.0 wt % or less, or 1.0 wt % or less, or 0.5 wt % or less, or 0.1 wt % or less, such as down to having substantially no aromatics content. Additionally or alternately, the sulfur content can be 500 wppm or less, or 250 wppm or less, or 100 wppm or less, or 10 wppm or less, such as down to 0.5 wppm or possibly still lower. Additionally, it is noted that an isoparaffinic blend component and/or isoolefinic blend component can contain substantially no polyaromatic hydrocarbons. Thus, blends including an isoparaffinic blend component and/or isoolefinic blend component can have a corresponding reduction in total polyaromatic hydrocarbons (relative to the content of the other blend components).

In some aspects, the resulting blended product can include at least a portion of one or more conventional diesel fuel(s). A conventional diesel fuel is defined herein as a fraction that already qualifies as a diesel fuel under at least one of ASTM D975 and EN 590. In such aspects, the resulting blended product can include 1.0 vol % to 99 vol % of a conventional diesel fuel fraction, or 1.0 vol % to 90 vol %, or 1.0 vol % to 70 vol %, or 1.0 vol % to 50 vol %, or 1.0 vol % to 30 vol %, or 1.0 vol % to 10 vol %, or 10 vol % to 99 vol %, or 10 vol % to 90 vol %, or 10 vol % to 70 vol %, or 10 vol % to 50 vol %, or 10 vol % to 30 vol %, or 30 vol % to 99 vol %, or 30 vol % to 90 vol %, or 30 vol % to 70 vol %, or 50 vol % to 99 vol %, or 50 vol % to 90 vol %, or 70 vol % to 99 vol %, or 70 vol % to 90 vol %. Thus, the resulting blended product can, in some aspects, include 50 vol % or less of a conventional diesel boiling range fraction, or 30 vol % or less, or 10 vol % or less, such as down to 1.0 vol % or possibly still lower.

In some aspects, the resulting blended product can include at least a portion of one or more mineral diesel boiling range fraction(s). In such aspects, the resulting blended product can include 1.0 vol % to 99 vol % of a mineral diesel fuel fraction, or 1.0 vol % to 90 vol %, or 1.0 vol % to 70 vol %, or 1.0 vol % to 50 vol %, or 1.0 vol % to 30 vol %, or 1.0 vol % to 10 vol %, or 10 vol % to 99 vol %, or 10 vol % to 90 vol %, or 10 vol % to 70 vol %, or 10 vol % to 50 vol %, or 10 vol % to 30 vol %, or 30 vol % to 99 vol %, or 30 vol % to 90 vol %, or 30 vol % to 70 vol %, or 50 vol % to 99 vol %, or 50 vol % to 90 vol %, or 70 vol % to 99 vol %, or 70 vol % to 90 vol %. Thus, the resulting blended product can, in some aspects, include 50 vol % or less of a mineral boiling range fraction, or 30 vol % or less, or 10 vol % or less, such as down to 1.0 vol % or possibly still lower.

In some aspects, the resulting blended product can include at least a portion of one or more synthetic diesel boiling range fraction(s), such as bio-derived diesel boiling range fractions and/or Fischer-Trospsch derived diesel boiling range fractions. In such aspects, the resulting blended product can include 1.0 vol % to 99 vol % of a synthetic diesel boiling range fraction, or 1.0 vol % to 90 vol %, or 1.0 vol % to 70 vol %, or 1.0 vol % to 50 vol %, or 1.0 vol % to 30 vol %, or 1.0 vol % to 10 vol %, or 10 vol % to 99 vol %, or 10 vol % to 90 vol %, or 10 vol % to 70 vol %, or 10 vol % to 50 vol %, or 10 vol % to 30 vol %, or 30 vol % to 99 vol %, or 30 vol % to 90 vol %, or 30 vol % to 70 vol %, or 50 vol % to 99 vol %, or 50 vol % to 90 vol %, or 70 vol % to 99 vol %, or 70 vol % to 90 vol %. Thus, the resulting blended product can, in some aspects, include 50 vol % or less of a synthetic diesel boiling range fraction, or 30 vol % or less, or 10 vol % or less, such as down to 1.0 vol % or possibly still lower.

It is noted that an isoparaffinic and/or isoolefinic blend component can be blended with a plurality of different types of fractions. For example, in some aspects, a blended product can include two or more (or three or more) of a conventional diesel fuel fraction, a mineral diesel boiling range fraction, and a synthetic diesel boiling range fraction.

In some aspects, after blending components together to form a diesel fuel boiling range fraction, it may be desirable to further treat the diesel boiling range fraction for any convenient reason, such as by hydroprocessing the diesel fuel boiling range fraction to reduce or remove heteroatoms such as sulfur, nitrogen and oxygen and/or to improve cold flow properties.

In some aspects, an isoparaffinic blend component (e.g., all or a portion of an isoparaffinic stream discussed in FIGS. 1-5) and/or isoolefinic blend component (e.g., all or a portion of an isoolefinic stream discussed in FIGS. 1-5) can be blended with one or more other fractions to form a marine fuel oil product or marine fuel oil blending component, such as a very low sulfur fuel oil (VLSFO) or an ultra low sulfur fuel oil (ULSFO). In other aspects, an isoparaffinic blend component and/or isoolefinic blend component can be blended with one or more other fractions to a form a marine gas oil product and/or marine gas oil blending component.

Examples of fractions that can be blended with an isoparaffinic blend component and/or isoolefinic blend component include, but are not limited to, conventional fuel oil fractions (including low sulfur fuel oil, VLSFO, and/or ULSFO), mineral fuel oil fractions, renewable fractions, hydroprocessed and/or non-hydroprocessed fractions, and cracked fractions.

Examples of hydroprocessed fractions include hydroprocessed distillate fractions (i.e., a hydroprocessed fraction having the distillate boiling range) and hydroprocessed resid fractions (i.e., a hydroprocessed fraction having the resid boiling range). It is noted that a hydroprocessed fraction derived from a biological source, such as hydrotreated vegetable oil, can correspond to a hydroprocessed distillate fraction and/or a hydroprocessed resid fraction, depending on the boiling range of the hydroprocessed fraction.

A cracked fraction refers to a hydrocarbon and/or hydrocarbonaceous fraction that is derived from the effluent of a thermal cracking or catalytic cracking process. A cracked distillate fraction (having the distillate boiling range), such as a light cycle oil from a fluid catalytic cracking process, is an example of a cracked fraction.

Renewable blending components can correspond to renewable distillate and/or vacuum gas oil and/or vacuum resid boiling range components that are renewable based on one or more attributes. Some renewable blending components can correspond to components that are renewable based on being of biological origin. Examples of renewable blending components of biological origin can include, but are not limited to, fatty acid methyl esters (FAME), fatty acid alkyl esters, biodiesel, biomethanol, biologically derived dimethyl ether, oxymethylene ether, liquid derived from biomass, pyrolysis products from pyrolysis of biomass, products from gasification of biomass, and hydrotreated vegetable oil. Other renewable blending components can correspond to components that are renewable based on being extracted from a reservoir using renewable energy, such as petroleum extracted from a reservoir using an extraction method that is powered by renewable energy, such as electricity generated by solar, wind, or hydroelectric power. Still other renewable blending components can correspond to blending components that are made or processed using renewable energy, such as Fischer-Tropsch distillate that is formed using processes that are powered by renewable energy, or conventional petroleum distillate that is hydroprocessed/otherwise refinery processed using reactors that are powered by renewable energy. Yet other renewable blending components can correspond to fuel blending components formed from recycling and/or processing of municipal solid waste, plastic waste, or another source of carbon-containing waste. An example of processing of waste is pyrolysis and/or gasification of waste, such as pyrolysis of plastic waste or gasification of municipal solid waste.

More generally, isoparaffinic blend components and/or isoolefinic blend components as described herein may be blended with any of the following and any combination thereof in order to form a fuel and/or fuel blending component: low sulfur diesel (sulfur content of less than 500 wppm), ultra low sulfur diesel (sulfur content <10 or <15 ppmw), low sulfur gas oil, ultra low sulfur gasoil, low sulfur kerosene, ultra low sulfur kerosene, hydrotreated straight run diesel, hydrotreated straight run gas oil, hydrotreated straight run kerosene, hydrotreated cycle oil, hydrotreated thermally cracked, hydrotreated thermally cracked gas oil, hydrotreated thermally cracked kerosene, hydrotreated coker diesel, hydrotreated coker gas oil, hydrotreated coker kerosene, hydrocracker diesel, hydrocracker gas oil, hydrocracker kerosene, gas-to-liquid diesel, gas-to-liquid kerosene, gas-to-liquid vacuum gas oil, hydrotreated vegetable oil, fatty acid methyl esters, non-hydrotreated straight-run diesel, non-hydrotreated straight-run kerosene, non-hydrotreated straight-run gas oil and any distillates derived from low sulfur crude slates, gas-to-liquid wax, and other gas-to-liquid hydrocarbons, non-hydrotreated cycle oil, non-hydrotreated fluid catalytic cracking slurry oil, non-hydrotreated pyrolysis gas oil, non-hydrotreated cracked light gas oil, non-hydrotreated cracked heavy gas oil, non-hydrotreated pyrolysis light gas oil, non-hydrotreated pyrolysis heavy gas oil, non-hydrotreated pyrolysis distillate (e.g., kerosene and/or diesel), non-hydrotreated pyrolysis residue, non-hydrotreated thermally cracked residue, non-hydrotreated thermally cracked heavy distillate, non-hydrotreated coker heavy distillates, non-hydrotreated vacuum gas oil, non-hydrotreated coker diesel, non-hydrotreated coker gas oil, non-hydrotreated coker vacuum gas oil, non-hydrotreated thermally cracked vacuum gas oil, non-hydrotreated thermally cracked diesel, non-hydrotreated thermally cracked gas oil, hydrotreated fats or oils such as hydrotreated vegetable oil, hydrotreated tall oil, etc., fatty acid methyl ester, Group 1 slack waxes, lube oil aromatic extracts, deasphalted oil, atmospheric tower bottoms, vacuum tower bottoms, steam cracker tar, any residue materials derived from low sulfur crude slates, LSFO, RSFO, or other LSFO/RSFO blend stocks.

In various aspects for forming a fuel oil product or fuel oil blend component, a blended product can contain 1.0 vol % to 50 vol % of an isoparaffinic blend component and/or isoolefinic blend component, or 10 vol % or more to 50 vol %, or 20 vol % to 50 vol %, or 1.0 vol % to 40 vol %, or 10 vol % to 40 vol %, or 20 vol % to 40 vol %, or 1.0 vol % to 30 vol %, or 10 vol % to 30 vol %, or 1.0 vol % to 20 vol %. In some aspects, a blended product can contain 1.0 vol % to 50 vol % of an isoparaffinic blend component, or 10 vol % or more to 50 vol %, or 20 vol % to 50 vol %, or 1.0 vol % to 40 vol %, or 10 vol % to 40 vol %, or 20 vol % to 40 vol %, or 1.0 vol % to 30 vol %, or 10 vol % to 30 vol %, or 1.0 vol % to 20 vol %. In some aspects, a blended product can contain 1.0 vol % to 50 vol % of an isoolefinic blend component, or 10 vol % or more to 50 vol %, or 20 vol % to 50 vol %, or 1.0 vol % to 40 vol %, or 10 vol % to 40 vol %, or 20 vol % to 40 vol %, or 1.0 vol % to 30 vol %, or 10 vol % to 30 vol %, or 1.0 vol % to 20 vol %.

In aspects related to forming a marine gas oil or marine gas oil blending component, a blended product can contain 1.0 vol % or more of an isoparaffinic blend component and/or isoolefinic blend component, or 10 vol % or more, or 20 vol % or more, or 30 vol % or more, or 40 vol % or more, or 60 vol % or more, or 75 vol % or more, such as up to 99 vol % or possibly still higher. In some aspects, such a blended product can include 1.0 vol % to 40 vol % of an isoparaffinic blend component and/or isoolefinic blend component, or 1.0 vol % to 20 vol %, or 10 vol % to 40 vol %, or 10 vol % to 20 vol %, or 20 vol % to 40 vol %. In other aspects, such a blended product can include 1.0 vol % to 99 vol % of an isoparaffinic blend component and/or isoolefinic blend component, or 1.0 vol % to 95 vol %, or 1.0 vol % to 80 vol %, or 1.0 vol % to 60 vol %, or 20 vol % to 99 vol %, or 20 vol % to 95 vol %, or 20 vol % to 80 vol %, or 40 vol % to 99 vol %, or 40 vol % to 95 vol %, or 40 vol % to 80 vol %, or 40 vol % to 60 vol %, or 60 vol % to 99 vol %, or 60 vol % to 95 vol %, or 60 vol % to 80 vol %, or 75 vol % to 99 vol %. In still other aspects, such a blended product can include 20 vol % to 80 vol % of an isoparaffinic blend component and/or isoolefinic blend component, or 20 vol % to 60 vol %, or 20 vol % to 40 vol %, or 40 vol % to 80 vol %, or 40 vol % to 60 vol %, or 60 vol % to 80 vol %.

In some aspects, the resulting blended product can include an unexpectedly high content of $C_{12-}$ isoparaffins and/or iso-olefins. In such aspects, the resulting blended product can contain 6.0 wt % or more of $C_{12-}$ isoparaffins and/or iso-olefins, or 10 wt % or more, or 15 wt % or more, 20 wt % or more, such as up to 40 wt % or possibly still higher. Additionally or alternately, in some aspects, the resulting blended product can include an unexpectedly high content of $C_{12}$ isoparaffins and/or iso-olefins. In such aspects, the resulting blended product can include 6.0 wt % or more of $C_{12}$ isoparaffins and/or iso-olefins, or 10 wt % or more, such as up to 20 wt % or possibly still higher.

In some aspects, the resulting blended product can have an unexpectedly high content of $C_9$ hydrocarbons. In such aspects, the resulting blended product can contain 5.0 wt % or more of $C_9$ hydrocarbons, or 10 wt % or more, or 15 wt % or more, such as up to 25 wt % or possibly still higher.

In various aspects related to a marine fuel oil or marine fuel oil blend component, the resulting blended product can have a density at 15° C. of 0.850 g/cm$^3$ to 0.980 g/cm$^3$, or 0.850 g/cm$^3$ to 0.950 g/cm$^3$, or 0.850 g/cm$^3$ to 0.900 g/cm$^3$, or 0.875 g/cm$^3$ to 0.980 g/cm$^3$, or 0.875 g/cm$^3$ to 0.950 g/cm$^3$, or 0.900 g/cm$^3$ to 0.980 g/cm$^3$, or 0.900 g/cm$^3$ to 0.950 g/cm$^3$, or 0.925 g/cm$^3$ to 0.980 g/cm$^3$, or 0.925 g/cm$^3$ to 0.950 g/cm$^3$. Additionally or alternately, the resulting blended product can have a flash point of 60° C. or higher, or 70° C. or higher, or 80° C. or higher, such as up to 180° C. or possibly still higher.

In various aspects related to a marine gas oil or marine gas oil blend component, the resulting blended product can have a density at 15° C. of 0.760 g/cm$^3$ to 0.855 g/cm$^3$, or 0.760 g/cm$^3$ to 0.825 g/cm$^3$, or 0.760 g/cm$^3$ to 0.810 g/cm$^3$, or 0.760 g/cm$^3$ to 0.800 g/cm$^3$, or 0.775 g/cm$^3$ to 0.825 g/cm$^3$, or 0.775 g/cm$^3$ to 0.810 g/cm$^3$, or 0.775 g/cm$^3$ to 0.800 g/cm$^3$, or 0.790 g/cm$^3$ to 0.825 g/cm$^3$, or 0.790 g/cm$^3$ to 0.855 g/cm$^3$, or 0.800 g/cm$^3$ to 0.855 g/cm$^3$, or 0.815 g/cm$^3$ to 0.855 g/cm$^3$, or 0.800 g/cm$^3$ to 0.825 g/cm$^3$. Additionally or alternately, the resulting blended product can have a flash point of 43° C. or higher, or 50° C. or higher, or 60° C. or higher, such as up to 120° C. or possibly still higher.

In various aspects, an isoparaffinic blend component and/or isoolefinic blend component can have favorable cold flow properties relative to other types of blend components. In aspects where the resulting blended product includes a) 10 vol % or more of an isoparaffinic blend component and/or isoolefinic blend component, and b) 50 vol % or more of a conventional and/or mineral blend component, the resulting blended product can have a cloud point that is lower than the cloud point of the conventional and/or mineral blend component by 10° C. or more, or 15° C. or more, or 20° C. or more, such as up to 60° C. lower or possibly still more. In aspects where the resulting blended product includes a) 10 vol % or more of an isoparaffinic blend component and/or isoolefinic blend component, and b) 40 vol % or more of a synthetic component (different from the isoparaffinic blend component and/or isoolefinic blend component), the resulting blended product can have a cloud point that is lower than the cloud point of the bio-derived component by 10° C. or more, or 15° C. or more, or 20° C. or more, such as up to 60° C. lower or possibly still more. In some aspects, the resulting blended product can have a cloud point of 6° C. or less, or 0° C. or less, or −6° C. or less, or −12° C. or less, such as down to −30° C. or possibly still lower.

In various aspects related to a fuel oil or fuel oil blend component, the resulting blended product can have a kinematic viscosity at 50° C. of 200 cSt or less, or 100 cSt or less, or 50 cSt or less, or 20 cSt or less, or 10 cSt or less, such as down to 1.0 cSt or possibly still lower. In some aspects, the resulting blended product can have a kinematic viscosity at 50° C. of 20 cSt to 100 cSt, or 20 cSt to 50 cSt. In various aspects related to a marine gas oil or marine gas oil blend component, the resulting blended product can have a kinematic viscosity at 40° C. of 2.0 cSt to 6.0 cSt, or 2.0 cSt to 5.0 cSt, or 3.0 cSt to 6.0 cSt, or 3.0 cSt to 5.0 cSt.

In some aspects, the resulting blended product can have a calculated carbon aromaticity index (CCAI) of 780 to 820, or 790 to 810, or 800 to 820.

In some aspects related to a fuel oil or fuel oil blend component, an isoparaffinic blend component and/or isoolefinic blend component can have a favorable estimated cetane number relative to other types of blend components. In aspects where 10 vol % or more of an isoparaffinic blend component and/or isoolefinic blend component is blended with 50 vol % or more of a conventional fuel oil and/or mineral fuel oil, the resulting blended product can have an estimated cetane number that is higher than the estimated cetane number for the conventional fuel oil and/or mineral fuel oil. In aspects where 10 vol % or more of an isoparaffinic blend component and/or isoolefinic blend component is blended with 40 vol % or more of a bio-derived component (different from the isoparaffinic and/or isoolefinic blend component), the resulting blended product can have an estimated cetane number that is higher than the estimated cetane number for the bio-derived component.

In some aspects related to a fuel oil, an isoparaffinic blend component and/or isoolefinic blend component can have a favorable estimated energy content relative to other types of blend components. In aspects where 10 vol % or more of an isoparaffinic blend component and/or isoolefinic blend component is blended with 50 vol % or more of a conventional fuel oil and/or mineral fuel oil, the resulting blended product can have an energy content that is higher than the energy content for the conventional fuel oil and/or mineral fuel oil. In aspects where 10 vol % or more of an isoparaffinic blend component and/or isoolefinic blend component is blended with 40 vol % or more of a bio-derived component (different from the isoparaffinic and/or isoolefinic blend component), the resulting blended product can have an energy content that is higher than the energy content for the bio-derived component.

In various aspects, an isoparaffinic blend component and/or an isoolefinic blend component can assist with reducing the sulfur content of a resulting blend. Because an isoparaffinic blend component and/or isoolefinic blend component typically has less than 100 wppm of sulfur (or less than 50 wppm, such as down to having substantially no sulfur content), such a blend component can offset a higher sulfur content in other components of a blend. In some aspects, the resulting blended product can have a sulfur content of 5000 wppm or less, or 2500 wppm or less, or 1000 wppm or less, or 500 wppm or less, such as down to 10 wppm or possibly still lower. It is noted that in aspects where a blended product includes only an isoparaffinic/isoolefinic blend components mixed with synthetic (e.g., bio-derived, Fischer-Tropsch) blend components, low sulfur contents can be achieved, such as sulfur contents of 100 wppm or less, or 10 wppm or less, such as down to having substantially no sulfur content (0.1 wppm or less).

In some aspects, the resulting blended product can include at least a portion of one or more conventional VLSFO fractions, ULSFO fractions, and/or marine gas oil (MGO) fractions. A conventional VLSFO, ULSFO, or MGO is defined herein as a fraction that already qualifies as a VLSFO fuel, ULSFO fuel, or MGO fuel under ISO 8217 (either Table 1 or Table 2). In such aspects, the resulting blended product can include 1.0 vol % to 99 vol % of a conventional diesel fuel fraction, or 1.0 vol % to 90 vol %, or 1.0 vol % to 70 vol %, or 1.0 vol % to 50 vol %, or 1.0 vol % to 30 vol %, or 1.0 vol % to 10 vol %, or 10 vol % to 99 vol %, or 10 vol % to 90 vol %, or 10 vol % to 70 vol %, or 10 vol % to 50 vol %, or 10 vol % to 30 vol %, or 30 vol % to 99 vol %, or 30 vol % to 90 vol %, or 30 vol % to 70 vol %, or 50 vol % to 99 vol %, or 50 vol % to 90 vol %, or 70 vol % to 99 vol %, or 70 vol % to 90 vol %.

In some aspects, the resulting blended product can include at least a portion of one or more mineral distillate boiling range fractions, vacuum gas oil boiling range fractions, and/or resid boiling range fractions. In such aspects, the resulting blended product can include 1.0 vol % to 99 vol % of one or more mineral fraction(s), or 1.0 vol % to 90 vol %, or 1.0 vol % to 70 vol %, or 1.0 vol % to 50 vol %, or 1.0 vol % to 30 vol %, or 1.0 vol % to 10 vol %, or 10 vol % to 99 vol %, or 10 vol % to 90 vol %, or 10 vol % to 70 vol %, or 10 vol % to 50 vol %, or 10 vol % to 30 vol %, or 30 vol % to 99 vol %, or 30 vol % to 90 vol %, or 30 vol % to 70 vol %, or 50 vol % to 99 vol %, or 50 vol % to 90 vol %, or 70 vol % to 99 vol %, or 70 vol % to 90 vol %.

In some aspects, the resulting blended product can include at least a portion of one or more synthetic fractions (different from the isoparaffinic blend component and/or isoolefinic blend component), such as bio-derived fractions and/or Fischer-Trospsch derived fractions. In such aspects, the resulting blended product can include 1.0 vol % to 99 vol % of a fraction, or 1.0 vol % to 90 vol %, or 1.0 vol % to 70 vol %, or 1.0 vol % to 50 vol %, or 1.0 vol % to 30 vol %, or 1.0 vol % to 10 vol %, or 10 vol % to 99 vol %, or 10 vol % to 90 vol %, or 10 vol % to 70 vol %, or 10 vol % to 50 vol %, or 10 vol % to 30 vol %, or 30 vol % to 99 vol %, or 30 vol % to 90 vol %, or 30 vol % to 70 vol %, or 50 vol % to 99 vol %, or 50 vol % to 90 vol %, or 70 vol % to 99 vol %, or 70 vol % to 90 vol %.

It is noted that an isoparaffinic and/or isoolefinic blend component can be blended with a plurality of different types of fractions. For example, in some aspects, a blended product can include two or more (or three or more) of a conventional fraction, a mineral fraction, and a synthetic fraction.

In some aspects, after blending components together to form a marine fuel or fuel blending component, it may be desirable to further treat the resulting blended product for any convenient reason, such as by hydroprocessing the blended product to reduce or remove heteroatoms such as sulfur, nitrogen and oxygen.

Isoparaffinic Blend Component for Blended Jet/Kerosene Boiling Range Products

In various aspects, an isoparaffinic blend component (e.g., all or a portion of an isoparaffinic stream discussed in FIGS. 1-5) can be used to form blended products that can correspond to jet fuels and/or jet fuel blending components. Optionally, an isoolefinic blend component can be used instead of or in addition to an isoparaffinic blend component.

In this discussion, to be either an isoparaffinic blend component or an isoolefinic blend component, a fraction will contain 50 wt % or more of a combined weight of isoparaffins and iso-olefins, or 60 wt % or more, or 70 wt % or more, or 80 wt % or more, such as up to the fraction substantially being composed of isoparaffins and iso-olefins (i.e., less than 5.0 wt % of other types of hydrocarbons/compounds, or less than 3.0 wt %, or less than 1.0 wt %, such as down to zero). In addition to the above, an isoparaffinic blend component refers to a fraction containing less than 5.0 wt % iso-olefins and 80 wt % or more of isoparaffins (relative to the weight of the fraction), or 85 wt % or more, or 90 wt % or more, such as up to having substantially all of the fraction correspond to isoparaffins. An isoolefinic blend component refers to a fraction that a) satisfies the requirement for the combined amount of iso-olefins and isoparaffins, and b) contains 5.0 wt % or more of iso-olefins, or 25 wt % or more, or 50 wt % or more, or 70 wt % or more, such as up to having substantially all of the fraction correspond to iso-olefins.

In various aspects, an isoparaffinic blend component and/or an isoolefinic blend component can have one or more of the following properties. In some aspects, 80 wt % or more of the blend component, or 90 wt % or more, or 94 wt % or more, or 97 wt % or more, is composed of $C_9$ to $C_{20}$ iso-olefins, isoparaffins, or a combination thereof. In some aspects, 2.0 wt % to 25 wt % of the blend component is composed of $C_9$ hydrocarbons, or 2.0 wt % to 15 wt %, or 5.0 wt % to 25 wt %, or 5.0 wt % to 15 wt %, or 2.0 wt % to 10 wt %. In some aspects, 1.0 wt % to 15 wt % of the blend component is composed of $C_{17+}$ hydrocarbons, or 2.5 wt % to 15 wt %. In some aspects, 1.0 wt % to 15 wt % of the blend component is composed of $C_{17}$ and/or $C_{18}$ hydrocarbons, or 2.5 wt % to 15 wt %, or 1.0 wt % to 10 wt %, or 2.5 wt % to 10 wt %. In some aspects, the blend component can contain 5.0 wt % or less of $C_{19+}$ hydrocarbons, or 3.0 wt % or less, or 1.0 wt % or less, such as down to having substantially no content of $C_{19+}$ hydrocarbons. In some aspects, the blend component can include 5.0 wt % or less of $C_{8-}$ hydrocarbons, or 3.0 wt % or less, or 1.0 wt % or less, or 0.5 wt % or less, such as down to 0.1 wt % or possibly still lower (i.e., substantially no $C_{8-}$ content). In some aspects, the blend component has a specific gravity at 15° C. of 0.730 g/cm³ to 0.775 g/cm³.

In some aspects, the blend component can contain 60 wt % to 90 wt % of $C_{11}$ to $C_{18}$ isoparaffins, based on the weight of the blend component. Additionally or alternately, the blend component can contain 50 wt % to 75 wt % of $C_{12}$ to $C_{16}$ isoparaffins, based on the weight of the blend component. This is particularly advantageous for the flexible use of the composition as an aviation or diesel fuel.

In various aspects, the blend component can contain a reduced or minimized amount of aromatics. This can correspond to containing 5.0 wt % or less of aromatics, or 3.0 wt % or less, or 1.0 wt % or less, or 0.5 wt % or less, or 0.1 wt % or less, such as down to having substantially no aromatics content.

In various aspects, the blend component can have a flash point of 38° C. or higher, or 40° C. or higher, or 45° C. or higher, or 50° C. or higher, or 55° C. or higher, such as up to 60° C. or possibly still higher. Additionally or alternately, the blend component, when tested alone (i.e., prior to blending with another fraction), can have a Jet Fuel Thermal Oxidation Test (JFTOT) breakpoint result of 260° C. or higher, or 270° C. or higher, or 280° C. or higher, such as up to 320° C. or possibly still higher.

In some aspects, the blend component, prior to adding any additives, can have an electrical conductivity of 10 pS/m or less (according to ASTM Test Method D2624), such as down to having substantially no electrical conductivity. It is noted that an isoparaffinic blend component as described herein has a good response to conductivity additives. After addition of conventional additives for conductivity, an isoparaffinic blend component can have a conductivity of 50 pS/m to 600 pS/m.

An isoparaffinic blend component can be blended with one or more other fractions to form a kerosene/jet boiling range product. Examples of fractions that can be blended with an isoparaffinic blend component include, but are not limited to, conventional jet fractions, mineral naphtha and/or jet and/or diesel boiling range fractions, and various types of synthetic naphtha, jet, and/or diesel boiling range fractions, such as sustainable aviation fuel fractions and/or Fischer-Tropsch fractions. Other challenged fractions where at least a portion of the fraction corresponds to jet/kerosene boiling range components can also be blended with an isoparaffinic blend component.

In various aspects, a blended product can contain 1.0 vol % or more of an isoparaffinic blend component, or 10 vol % or more, or 30 vol % or more, or 50 vol % or more, or 65 vol % or more, or 75 vol % or more, such as up to 99 vol % or possibly still higher. In some aspects, such a blended product can include 1.0 vol % to 20 vol % of an isoparaffinic blend component, or 1.0 vol % to 15 vol %, or 5.0 vol % to 20 vol %, or 5.0 vol % to 15 vol %, or 10 vol % to 20 vol %. In other aspects, such a blended component can include 30 vol % to 99 vol % of an isoparaffinic blend component, or 30 vol % to 95 vol %, or 30 vol % to 80 vol %, or 30 vol % to 60 vol %, or 30 vol % to 45 vol %, or 50 vol % to 99 vol %, or 50 vol % to 95 vol %, or 50 vol % to 80 vol %, or 70 vol % to 99 vol %.

In some aspects, 0.1 wt % to 15 wt % of the resulting blended product can be $C_{17}+$ hydrocarbons, or 1.0 wt % to 15 wt %, or 2.5 wt % to 15 wt %, or 0.1 wt % to 10 wt %, or 1.0 wt % to 10 wt %, or 2.5 wt % to 10 wt %, or 1.0 wt % to 6.0 wt %, or 2.5 wt % to 6.0 wt %, or 1.0 wt % to 3.0 wt %, or 0.1 wt % to 6.0 wt %, or 0.1 wt % to 3.0 wt %. In some aspects, 0.1 wt % to 15 wt % of the resulting blended product can be $C_{17}$ and/or $C_{18}$ hydrocarbons. For example, the resulting blended product can include 0.1 wt % or more of $C_{17}$-$C_{18}$ hydrocarbons, or 1.0 wt % or more, or 1.5 wt % or more, or 2.0 wt % or more, or 4.0 wt % or more, or 6.0 wt % or more, or 10 wt % or more, such as up to 15 wt %. In some aspects, the resulting blended product can contain 5.0 wt % or less of $C_{19+}$ hydrocarbons, or 3.0 wt % or less, or 1.0 wt % or less, or 0.1 wt % or less, such as down to having substantially no content of $C_{19+}$ hydrocarbons.

In some aspects, the resulting blended product can have an unexpectedly high content of $C_9$ hydrocarbons. In such aspects, the resulting blended product can contain 5.0 wt % or more of $C_9$ hydrocarbons, or 10 wt % or more, or 15 wt % or more, such as up to 25 wt % or possibly still higher.

In various aspects, the resulting blended product can have a specific gravity at 15° C. of 0.775 g/cm³ to 0.840 g/cm³. Additionally or alternately, the resulting blended product can have a flash point of 38° C. or higher, or 40° C. or higher, or 45° C. or higher, or 50° C. or higher, such as up to 60° C. or possibly still higher. Further additionally or alternately, the resulting blended product can have a Jet Fuel Thermal Oxidation Test (JFTOT) breakpoint result of 260° C. or higher, or 270° C. or higher, or 280° C. or higher, such as up to 320° C. or possibly still higher. Still further additionally or alternately, the resulting blended product can have a freeze point of −40° C. or less, or −47° C. or less, or −50° C. or less, or −55° C. or less, such as down to −70° C. or possibly still lower.

In some aspects, the resulting blended product can have a final boiling point of 300° C. or less, even though the resulting blended product contains 1.0 wt % or more of $C_{17}$ hydrocarbons.

In various aspects, the resulting blended product can contain a reduced or minimized amount of aromatics. This can correspond to containing 15 wt % or less of aromatics, or 10 wt % or less, or 5.0 wt % or less, or 3.0 wt % or less, or 1.0 wt % or less, or 0.5 wt % or less, or 0.1 wt % or less, such as down to having substantially no aromatics content. Additionally or alternately, the sulfur content can be 500 wppm or less, or 250 wppm or less, or 100 wppm or less, or 10 wppm or less, such as down to 0.5 wppm or possibly still lower.

In some aspects, the resulting blended product can include at least a portion of one or more conventional jet fuel(s). A conventional jet fuel is defined herein as a fraction that already qualifies as a jet fuel under at least one of ASTM D1655, UK Ministry of Defence Standard 91-091, and Canadian General Standards Board 3.23. In such aspects, the resulting blended product can include 1.0 vol % to 99 vol % of a conventional jet fuel fraction, or 1.0 vol % to 90 vol %, or 1.0 vol % to 70 vol %, or 1.0 vol % to 50 vol %, or 1.0 vol % to 30 vol %, or 1.0 vol % to 10 vol %, or 10 vol % to 70 vol %, or 10 vol % to 50 vol %, or 10 vol % to 30 vol %, or 30 vol % to 70 vol %. Thus, the resulting blended product can, in some aspects, include 50 vol % or less of a conventional jet fuel fraction, or 30 vol % or less, or 10 vol % or less, such as down to 1.0 vol % or possibly still lower.

In some aspects, the resulting blended product can include at least a portion of one or more mineral kerosene/jet boiling range fraction(s). In such aspects, the resulting blended product can include 1.0 vol % to 99 vol % of a jet/kerosene boiling range fraction, or 1.0 vol % to 90 vol %, or 1.0 vol % to 70 vol %, or 1.0 vol % to 50 vol %, or 1.0 vol % to 30 vol %, or 1.0 vol % to 10 vol %, or 10 vol % to 70 vol %, or 10 vol % to 50 vol %, or 10 vol % to 30 vol %, or 30 vol % to 70 vol %. Thus, the resulting blended product can, in some aspects, include 50 vol % or less of a jet/kerosene boiling range fraction, or 30 vol % or less, or 10 vol % or less, such as down to 1.0 vol % or possibly still lower.

In some aspects, the resulting blended product can include at least a portion of one or more synthetic jet boiling range fraction(s), optionally as defined in ASTM D7566. In such aspects, the resulting blended product can include 1.0 vol % to 99 vol % of a synthetic jet boiling range fraction, or 1.0 vol % to 90 vol %, or 1.0 vol % to 70 vol %, or 1.0 vol % to 50 vol %, or 1.0 vol % to 30 vol %, or 1.0 vol % to 10 vol %, or 10 vol % to 70 vol %, or 10 vol % to 50 vol %, or 10 vol % to 30 vol %, or 30 vol % to 70 vol %. Thus, the resulting blended product can, in some aspects, include 50 vol % or less of a synthetic jet boiling range fraction, or 30 vol % or less, or 10 vol % or less, such as down to 1.0 vol % or possibly still lower.

It is noted that an isoparaffinic and/or isoolefinic component can be blended with a plurality of different types of fractions. For example, in some aspects, a blended product can include two or more (or three or more) of a conventional jet fuel fraction, a mineral jet boiling range fraction, and a synthetic fraction. Examples of synthetic fractions include bio-derived fractions, sustainable aviation fuels, and/or Fischer-Tropsch fractions.

In some aspects, after blending components together to form a kerosene/jet fuel boiling range fraction, it may be desirable to further treat the kerosene/jet boiling range fraction for any convenient reason. Examples of further treatment methods can include, but are not limited to, wet treating, clay treatment, acid and/or caustic treatment, mercaptan oxidation, salt drying, and hydroprocessing.

Distribution of Carbon Atom Types in Isoparaffinic Stream and Related Blend Components and Blends In some aspects, an isoparaffinic stream formed according to this method may have a distribution of types of carbon atoms within the hydrocarbons of the isoparaffinic stream that is distinct from a fraction containing isoparaffins that are formed by another method, such as by isomerization of an n-paraffin feed. This difference in the types of carbon atoms can be characterized using various types of nuclear magnetic resonance (NMR) analysis, including $^1$H NMR and $^{13}$C NMR.

$^1$H NMR can be used to roughly characterize the amount of hydrogen in a sample that corresponds to $CH_3$ groups (primary or terminal carbons), $CH_2$ groups (secondary carbons) and CH groups (tertiary carbons). The reason that this is only an approximate characterization is that the presence of aromatic rings can alter the resonance location for certain types of hydrogens. However, this impact of aromatic rings is general for all types of $^1$H NMR, and the change in the detected number of $CH_3$ groups, $CH_2$ groups, and CH groups is minimal for any sample containing less than 60 wt % aromatics. Thus, $^1$H NMR can be used to characterize in a repeatable manner the content of $CH_3$ groups, $CH_2$ groups, and CH groups in a sample.

In general, $^1$H NMR can be used to characterize the number of $CH_3$ groups, $CH_2$ groups, and CH groups in a sample in the following manner. Based on peak position, $^1$H NMR can generally characterize hydrogens in a hydrocarbon (or hydrocarbon-like) sample as falling into one of 6 types of groups: 1) hydrogens attached to an aromatic ring; 2) hydrogens attached to carbons that are part of an olefinic bond; 3) hydrogens attached to a carbon that is alpha to an aromatic ring (i.e., hydrogen is attached to a first carbon, the first carbon is attached to a second carbon that is part of an aromatic ring); 4) hydrogens that are part of a $CH_3$; 5) hydrogens that are part of a $CH_2$ group, and 6) hydrogens that are part of a CH group. The peaks corresponding to these 6 types of hydrogen can then be integrated. This provides relative ratios of for the amount of each type of hydrogen that is present. These ratios can then be used to determine the relative percentages of the corresponding types of carbons that are present in a sample. In particular, for the hydrogens attached to $CH_3$ groups and $CH_2$ groups, the amount of hydrogens present needs to be divided by 3 or 2, respectively, in order to convert the relative hydrogen amount detected by NMR into a relative number of $CH_3$ groups or $CH_2$ groups.

In this discussion, "$CH_3$ groups" are defined as paraffinic/aliphatic $CH_3$ groups as determined based on $^1$H NMR. This is determined by integration of the hydrogen peak corresponding to the peak in the NMR spectrum that corresponds to hydrogens that are part of a $CH_3$ group. It is noted that hydrogens from any $CH_3$ group where the carbon of the $CH_3$ group is in the alpha or beta position relative to an aromatic ring (e.g., the $CH_3$ is part of a methyl or ethyl group attached to an aromatic ring) are not part of this peak. $CH_3$ groups in a side chain from an aromatic ring that are in the gamma position or farther away are included here. Therefore, to the degree aromatics are present, the amount of $CH_3$ groups detected based on $^1$H NMR may be slightly lower than the actual content of $CH_3$ groups. However, this is a small error for samples having less than 60 wt % aromatics. Thus, in this discussion, references to $CH_3$ groups in a sample are defined as $CH_3$ groups as detected by $^1$H NMR, without an attempt to correct the NMR value based on this possible undercounting error due to the presence of aromatics.

In this discussion, "$CH_2$ groups" are defined as paraffinic/aliphatic $CH_2$ groups as determined based on $^1$H NMR. This is determined by integration of the hydrogen peak corresponding to the peak in the NMR spectrum that corresponds to hydrogens that are part of a $CH_2$ group. It is noted that hydrogens from any $CH_2$ group that is alpha or beta to an aromatic ring are not part of this peak. Additionally, hydrogens from a $CH_3$ group that is beta to an aromatic ring are included in this peak. Therefore, to the degree aromatics are present, the amount of $CH_2$ groups detected based on $^1$H NMR may be slightly lower, slightly higher, or the same as the actual content of $CH_2$ groups. However, this is a small error for samples having less than 60 wt % aromatics. Thus, in this discussion, references to $CH_2$ groups in a sample are defined as $CH_2$ groups as detected by $^1$H NMR, without an attempt to correct the NMR value based on possible undercounting and/or overcounting errors due to the presence of aromatics. It is noted that $CH_2$ groups that are part of a naphthene ring are included in the $CH_2$ NMR peak.

In this discussion, "CH groups" are defined as paraffinic/aliphatic CH groups as determined based on $^1$H NMR. This is determined by integration of the hydrogen peak corresponding to the peak in the NMR spectrum that corresponds to hydrogens that are part of a CH group. As noted above, any hydrogens directly attached to an aromatic ring are not included in this peak. Additionally, it is noted that hydrogens from any CH group that is alpha or beta to an aromatic ring are not part of this peak. Further, hydrogens from a $CH_2$ group that is beta to an aromatic ring are included in this peak. Therefore, to the degree aromatics are present, the amount of CH groups detected based on $^1$H NMR may be slightly lower, slightly higher, or the same as the actual content of CH groups. However, this is a small error for samples having less than 60 wt % aromatics. Thus, in this discussion, references to CH groups in a sample are defined as paraffinic/aliphatic CH groups as detected by $^1$H NMR, without an attempt to correct the NMR value based on possible undercounting and/or overcounting errors due to the presence of aromatics. It is noted that CH groups that are part of a naphthene ring are included in the CH NMR peak.

In various aspects, an isoparaffinic stream (e.g., an isoparaffinic stream discussed in FIGS. 1-5) can have a ratio of $CH_3$ groups (as determined based on $^1$H NMR) to $CH_2$ groups (as determined based on $^1$H NMR) of 1.01 to 1.35, or 1.01 to 1.25, or 1.10 to 1.35, or 1.10 to 1.25. By blending an at least a portion of the isoparaffinic stream (also referred to as an isoparaffinic blend component) with another fraction, a resulting blend can be formed that has a ratio of $CH_3$ groups to $CH_2$ groups (both as determined based on $^1$H NMR) of 1.01 to 2.30, or 1.01 to 2.00, or 1.01 to 1.80, or 1.01 to 1.50, or 1.01 to 1.15, or 1.36 to 2.30, or 1.36 to 2.00, or 1.36 to 1.80, or 1.70 to 2.30. It is noted that the ratio of $CH_3$ to $CH_2$ groups can vary depending on the type of fraction that is blended with an isoparaffinic blend component. For example, blending an isoparaffinic blend component with a mineral jet boiling range fraction, a mineral distillate boiling range fraction, or a Fischer-Tropsch fraction and/or fraction with a high n-paraffin content, will tend to result in blends having a lower ratio. By contrast, blending an isoparaffinic blend component with a fraction that has been highly isomerized in a catalytic dewaxing/isomerization process will tend to result in blends having a higher ratio.

In addition to characterizing hydrogen for full samples, $^{13}$C NMR was used to characterize the quaternary carbon content of the $C_{12}$ fraction of various samples. For this type of measurement, gas chromatography can be used to separate the $C_{12}$ compounds present in a sample from the remaining hydrocarbons. A straightforward method that can be used for forming a $C_{12}$ fraction is the normal paraffin (or linear paraffin) gas chromatograph method. That is, for an appropriate gas chromatograph with a separation column of adequate resolution, a normal paraffin of a given carbon number is assumed to delineate a peak, above which, species may be assumed to comprise the carbon number of the next higher carbon number normal paraffin peak. For example, all peaks for material eluting in between the peaks for n-decane and n-undecane are assumed to be $C_{11}$ species.

The resulting $C_{12}$ fraction can then be characterized using $^{13}C$ NMR. It has been discovered that the $C_{12}$ fraction of an isoparaffinic blend component made according to the methods described herein can have an unexpectedly low content of quaternary carbons relative to a fraction made by catalytic isomerization of n-paraffins. In such aspects, the quaternary carbon content of the $C_{12}$ fraction of an isoparaffinic blend component can be 1.5% or less of the total carbons present in the $C_{12}$ fraction, or 1.4% or less, or 1.3% or less, such as down to 1.0% or possibly still lower.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the incarnations of the present inventions. At the very least, and not as an attempt to limit the application of the doctrine of equivalents to the scope of the claim, each numerical parameter should at least be construed in light of the number of reported significant digits and by applying ordinary rounding techniques.

One or more illustrative incarnations incorporating one or more invention elements are presented herein. Not all features of a physical implementation are described or shown in this application for the sake of clarity. It is understood that in the development of a physical embodiment incorporating one or more elements of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

Additional Embodiments

Embodiment 1. A method for producing an isoolefinic stream comprising: oligomerizing an ethylene stream to a C4+ olefin stream in a first olefin oligomerization unit comprising a serial reactor and a lights removal column, wherein the C4+ olefin stream contains no greater than 10 wt % of methane, ethylene, and ethane combined; and wherein the ethylene stream contains at least 50 wt % ethylene, at least 2000 wppm ethane, no greater than 1000 wppm of methane, and no greater than 20 wppm each of carbon monoxide and hydrogen; and oligomerizing the C4+ olefin stream and a propylene/C4+ olefin stream in a second oligomerization unit to produce the isoolefinic stream.

Embodiment 2. The method of Embodiment 1, wherein the C4+ olefin stream contains no greater than 5 wt % of methane, ethylene, and ethane combined.

Embodiment 3. The method of any one of Embodiments 1-2, wherein the C4+ olefin stream contains no greater than 2000 wppm of methane, ethylene, and ethane combined.

Embodiment 4. The method of any one of Embodiments 1-3, wherein the ethylene stream contains at least 50 wt % ethylene, at least 2000 wppm ethane, no greater than 1000 wppm of methane, and no greater than 5 wppm each of carbon monoxide and hydrogen.

Embodiment 5. The method of any one of Embodiments 1-4, wherein the ethylene stream contains at least 50 wt % ethylene, at least 2000 wppm ethane, no greater than 1000 wppm of methane, and no greater than 1 wppm each of carbon monoxide and hydrogen.

Embodiment 6. The method of any one of Embodiments 1-5 further comprising: hydroprocessing the isoolefinic stream with hydrogen as treat gas to produce an isoparaffinic stream having no greater than 10 wt % olefin content.

Embodiment 7. The method of any one of Embodiments 1-6 further comprising: combining the C4+ olefin stream and the propylene/C4+ olefin stream before the second oligomerization.

Embodiment 8. The method of any one of Embodiments 1-7, wherein the first oligomerization unit utilizes a homogeneous catalyst, and wherein the second oligomerization unit utilize a heterogeneous catalyst.

Embodiment 9. The method of any one of Embodiments 1-8 further comprising: recycling a portion of the C4+ olefin stream that is not oligomerized during the second oligomerization back to the second oligomerization again.

Embodiment 10. A method comprising: converting an oxygenate to olefins to produce a raw olefin stream; wherein the raw olefin stream comprises ethylene, propylene, and C4+ olefins, wherein at least 10 wt % of all olefins in the raw olefin stream are ethylene, and further containing at least 1000 wppm of each methane and ethane, and at least 100 wppm of each carbon monoxide and hydrogen; separating the raw olefin stream to remove hydrogen, carbon monoxide, propylene and C4+ olefins from the raw olefin stream, and produce an ethylene stream containing at least 50 wt % ethylene, at least 2000 wppm ethane, no greater than 1000 wppm of methane, and no greater than 20 wppm each of carbon monoxide and hydrogen, wherein at least 95 wt % of all the ethylene in the raw olefin stream is recovered in the ethylene stream; and oligomerizing at least a portion of the ethylene stream to convert at least 90% of the ethylene contained in the ethylene stream to a C4+ olefin stream containing no greater than 10 wt % of methane, ethylene, and ethane combined.

Embodiment 11. The method of Embodiment 10, wherein the C4+ olefin stream contains no greater than 5 wt % of methane, ethylene, and ethane combined.

Embodiment 12. The method of any one of Embodiments 10-11, wherein the C4+ olefin stream contains no greater than 2000 wppm of methane, ethylene, and ethane combined.

Embodiment 13. The method of any one of Embodiments 10-12, wherein the ethylene stream contains at least 50 wt % ethylene, at least 2000 wppm ethane, no greater than 1000 wppm of methane, and no greater than 5 wppm each of carbon monoxide and hydrogen.

Embodiment 14. The method of any one of Embodiments 10-13, wherein the ethylene stream contains at least 50 wt % ethylene, at least 2000 wppm ethane, no greater than 1000 wppm of methane, and no greater than 1 wppm each of carbon monoxide and hydrogen.

Embodiment 15. The method of any one of Embodiments 10-14, wherein the ethylene stream contains at least 90% of the ethane present in the raw olefin stream.

Embodiment 16. The method of any one of Embodiments 10-15, wherein the oxygenate is converted to olefins using a silicoaluminophosphate catalyst, an aluminosilicate catalyst, or steam cracking.

Embodiment 17. The method of any one of Embodiments 10-16, wherein the first oligomerization unit utilizes a homogeneous catalyst, and wherein the second oligomerization unit utilize a heterogeneous catalyst Embodiment 18. The method of any one of Embodiments 10-17, wherein the hydrogen and carbon monoxide are separated from the propylene and C4+ olefins when separated from the raw olefin stream.

Embodiment 19. A method for producing an isoolefinic stream comprising: providing a raw olefin stream comprising ethylene, propylene and C4+ olefins, wherein at least 10 wt % of all olefins in the raw olefin stream are ethylene, and further containing at least 1000 wppm of each methane and ethane, and at least 100 wppm of each carbon monoxide and hydrogen; separating the raw olefin stream to remove hydrogen, carbon monoxide, propylene and C4+ olefins from the raw olefin stream, and produce an ethylene stream containing at least 50 wt % ethylene, at least 2000 wppm ethane, no greater than 1000 wppm of methane, and no greater than 20 wppm each of carbon monoxide and hydrogen, wherein at least 95 wt % of all the ethylene in the raw olefin stream is recovered in the ethylene stream; oligomerizing at least a portion of the ethylene stream in a first olefin oligomerization unit comprising a serial reactor and a lights removal column, to convert in a single pass through the serial reactor(s) at least 90% of the ethylene contained in the ethylene stream to a C4+ olefin stream containing no greater than 10 wt % of methane, ethylene, and ethane combined; and oligomerizing at least a portion of each of the propylene and the C4+ olefins removed from the raw olefins stream, and at least a portion of the C4+ stream in a second olefin oligomerization unit comprising a serial reactor and a fractionation column to produce the isoolefinic stream.

Embodiment 20. The method of Embodiment 19, wherein the C4+ olefin stream contains no greater than 5 wt % of methane, ethylene, and ethane combined.

Embodiment 21. The method of any one of Embodiments 19-20, wherein the C4+ olefin stream contains no greater than 2000 wppm of methane, ethylene, and ethane combined.

Embodiment 22. The method of any one of Embodiments 19-21, wherein the ethylene stream contains at least 50 wt % ethylene, at least 2000 wppm ethane, no greater than 1000 wppm of methane, and no greater than 5 wppm each of carbon monoxide and hydrogen.

Embodiment 23. The method of any one of Embodiments 19-22, wherein the ethylene stream contains at least 50 wt % ethylene, at least 2000 wppm ethane, no greater than 1000 wppm of methane, and no greater than 1 wppm each of carbon monoxide and hydrogen.

Embodiment 24. The method of any one of Embodiments 19-23, wherein the ethylene stream contains at least 90% of the ethane present in the raw olefin stream.

Embodiment 25. The method of any one of Embodiments 19-24 further comprising: hydroprocessing the isoolefinic stream with hydrogen as treat gas to produce an isoparaffinic stream having no greater than 10 wt % olefin content.

Embodiment 26. The method of any one of Embodiments 19-25, wherein the separating of the raw olefin stream comprises: separating propylene and C4+ from the raw olefin stream in a deethanizer distillation column; and separating methane, hydrogen, and carbon monoxide from the raw olefin stream in a demethanizer distillation column to produce the ethylene stream.

Embodiment 27. The method of Embodiment 26, further comprising: separating the propylene from the C4+ olefins, and then further separating the propylene from propane and components of similar or lower volatility by using additional distillation columns.

Embodiment 28. The method of any one of Embodiments 19-27, wherein the first oligomerization unit utilizes a homogeneous catalyst, and wherein the second oligomerization unit utilize a heterogeneous catalyst.

Embodiment 29. The method of any one of Embodiments 19-28, wherein the fractionation column in the second oligomerization unit comprises: a distillate fractionation column that outputs the isoolefinic stream; and a debutanizer fractionation column that purges C4− olefins.

Embodiment 30. The method of Embodiment 29, wherein the distillate fractionation column also outputs C9− olefins, of which a first portion is recycled to the serial reactor and a second portion is sent to the debutanizer fractionation column.

Embodiment 31. The method of Embodiment 29, wherein the debutanizer fractionation column also outputs C5+ olefins, of which a first portion is recycled to the serial reactor and a second portion is purged.

Embodiment 32. The method of Embodiment 29, wherein the C4+ stream travels first to the distillate fractionation tower when entering the second oligomerization unit, while the propylene and the C4+ olefins removed from the raw olefins stream travel first to the serial reactor.

Embodiment 33. The method of any one of Embodiments 19-32 further comprising: converting an oxygenate to olefins to produce a raw olefin stream.

Embodiment 34. The method of Embodiment 33, wherein the oxygenate is converted to olefins by using a silicoaluminophosphate catalyst, an aluminosilicate catalyst, or steam cracking.

To facilitate a better understanding of the embodiments of the present invention, the following examples of preferred or representative embodiments are given. In no way should the following examples be read to limit, or to define, the scope of the invention.

EXAMPLES

Example 1—Carbon Chain Length Distribution in Isoparaffinic Blend Component

Several different samples of isoparaffinic blend component were formed using the synthesis methods described herein. Table 1A shows the weight percentage of isoparaffins having various hydrocarbon chain lengths in the resulting isoparaffinic blend components. The samples are referred to as IPB-1, IPB-2, and IPB-3 (for Isoparaffinic Blend Component). For comparison, isoparaffin carbon chain length distributions in a representative hydroprocessed vegetable oil (HVO) sample. The HVO represents a vegetable oil that has been exposed to hydrotreating and some type of hydroisomerization. Although not shown in Table 1A below, it is noted that the HVO sample also included 0.25 wt % of $C_{7-}$ isoparaffin components, while the IPB samples included no components below $C_8$.

TABLE 1A

Isoparaffin Chain Length Distribution

| [wt % isoparaffins] | C8 | C9 | C10 | C11 | C12 | C13/14 | C15/16 | C17/18 | C19/20 | C21+ |
|---|---|---|---|---|---|---|---|---|---|---|
| HVO | 0.42 | 0.49 | 0.72 | 0.89 | 0.83 | 2.28 | 8.66 | 63.16 | 0.76 | 0.30 |
| IPB-1 | 0.4 | 5 | 8.7 | 16.1 | 31.6 | 18.7 | 14 | 3.8 | 1.8 | |
| IPB-2 | 0.3 | 20 | 7.3 | 13.6 | 26.6 | 15.7 | 11.8 | 3.2 | 1.5 | |
| IPB-3 | 0.2 | 12.6 | 12.6 | 14.3 | 22.8 | 18.6 | 13 | 4.3 | 1.6 | |

As shown in Table 1A, more than 70 wt % of the hydrotreated vegetable oil sample corresponds to $C_{15}$-$C_{18}$ isoparaffins. By contrast, the isoparaffin chain length distribution for the IPB samples peaks at $C_{12}$, while still retaining a small but noticeable content of $C_{17}$-$C_{20}$ hydrocarbons.

Tables 1B, 1C, 1D, and 1E show the weight percentage of isoparaffins of various chain lengths that would be incorporated into a blended product that included 70 wt % of an isoparaffinic blend component (Table 1B), 50 wt % (Table 1C), 30 wt % (Table 1D), or 10 wt % (Table 1E). Due to the difference in the peaks for the chain length distributions, even adding 10 wt % of an isoparaffinic (or isoolefinic) blend component to a hydrotreated vegetable oil can result in substantial changes in the $C_{12-}$ portion of the isoparaffin chain length distribution of the resulting blended product.

TABLE 1B

Blend Contributions at 70 wt % IPB

| [wt % isoparaffins] | C8 | C9 | C10 | C11 | C12 | C13/14 | C15/16 | C17/18 | C19/20 | C21+ |
|---|---|---|---|---|---|---|---|---|---|---|
| HVO | 0.1 | 0.1 | 0.2 | 0.3 | 0.2 | 0.7 | 2.6 | 18.9 | 0.2 | 0.1 |
| IPB-1 | 0.3 | 3.5 | 6.1 | 11.3 | 22.1 | 13.1 | 9.8 | 2.7 | 1.3 | 0.0 |
| IPB-2 | 0.2 | 14.0 | 5.1 | 9.5 | 18.6 | 11.0 | 8.3 | 2.2 | 1.1 | 0.0 |
| IPB-3 | 0.1 | 8.8 | 8.8 | 10.0 | 16.0 | 13.0 | 9.1 | 3.0 | 1.1 | 0.0 |

TABLE 1C

Blend Contributions at 50 wt % IPB

| [wt % isoparaffins] | C8 | C9 | C10 | C11 | C12 | C13/14 | C15/16 | C17/18 | C19/20 | C21+ |
|---|---|---|---|---|---|---|---|---|---|---|
| HVO | 0.2 | 0.2 | 0.4 | 0.4 | 0.4 | 1.1 | 4.3 | 31.6 | 0.4 | 0.1 |
| IPB-1 | 0.2 | 2.5 | 4.4 | 8.1 | 15.8 | 9.4 | 7.0 | 1.9 | 0.9 | 0.0 |
| IPB-2 | 0.2 | 10.0 | 3.7 | 6.8 | 13.3 | 7.9 | 5.9 | 1.6 | 0.8 | 0.0 |
| IPB-3 | 0.1 | 6.3 | 6.3 | 7.2 | 11.4 | 9.3 | 6.5 | 2.2 | 0.8 | 0.0 |

TABLE 1D

Blend Contributions at 30 wt % IPB

| [wt % isoparaffins] | C8 | C9 | C10 | C11 | C12 | C13/14 | C15/16 | C17/18 | C19/20 | C21+ |
|---|---|---|---|---|---|---|---|---|---|---|
| HVO | 0.3 | 0.3 | 0.5 | 0.6 | 0.6 | 1.6 | 6.1 | 44.2 | 0.5 | 0.2 |
| IPB-1 | 0.1 | 1.5 | 2.6 | 4.8 | 9.5 | 5.6 | 4.2 | 1.1 | 0.5 | 0.0 |
| IPB-2 | 0.1 | 6.0 | 2.2 | 4.1 | 8.0 | 4.7 | 3.5 | 1.0 | 0.5 | 0.0 |
| IPB-3 | 0.1 | 3.8 | 3.8 | 4.3 | 6.8 | 5.6 | 3.9 | 1.3 | 0.5 | 0.0 |

TABLE 1E

Blend Contributions at 10 wt % IPB

| [wt % isoparaffins] | C8 | C9 | C10 | C11 | C12 | C13/14 | C15/16 | C17/18 | C19/20 | C21+ |
|---|---|---|---|---|---|---|---|---|---|---|
| HVO | 0.4 | 0.4 | 0.6 | 0.8 | 0.7 | 2.1 | 7.8 | 56.8 | 0.7 | 0.3 |
| IPB-1 | 0.0 | 0.5 | 0.9 | 1.6 | 3.2 | 1.9 | 1.4 | 0.4 | 0.2 | 0.0 |
| IPB-2 | 0.0 | 2.0 | 0.7 | 1.4 | 2.7 | 1.6 | 1.2 | 0.3 | 0.2 | 0.0 |
| IPB-3 | 0.0 | 1.3 | 1.3 | 1.4 | 2.3 | 1.9 | 1.3 | 0.4 | 0.2 | 0.0 |

A similar comparison of isoparaffin content and chain lengths was made relative to a conventional diesel sample. Table 2A shows the isoparaffin contents for the conventional diesel and the three different IPB samples.

TABLE 2A

Isoparaffin Chain Length Distribution

| [wt % isoparaffins] | C8 | C9 | C10 | C11 | C12 | C13/14 | C15/16 | C17/18 | C19/20 | C21+ |
|---|---|---|---|---|---|---|---|---|---|---|
| Diesel | 0.00 | 0.08 | 0.40 | 0.39 | 0.20 | 2.83 | 8.49 | 2.84 | 1.33 | 0.24 |
| IPB-1 | 0.4 | 5 | 8.7 | 16.1 | 31.6 | 18.7 | 14 | 3.8 | 1.8 | 0 |
| IPB-2 | 0.3 | 20 | 7.3 | 13.6 | 26.6 | 15.7 | 11.8 | 3.2 | 1.5 | 0 |
| IPB-3 | 0.2 | 12.6 | 12.6 | 14.3 | 22.8 | 18.6 | 13 | 4.3 | 1.6 | 0 |

As shown in Table 2A, the conventional diesel sample contained relatively few $C_{14-}$ isoparaffins. The $C_{13}$-$C_{14}$ isoparaffins corresponded to less than 3 wt % of the diesel sample, while the $C_{12-}$ isoparaffins corresponded to less than 1.1 wt % of the sample. By contrast, the IPB samples are highly isomerized, so that 95+ wt % or more of the hydrocarbons in the IPB samples correspond to isoparaffins. As a result, the IPB samples include 15 wt % or more of $C_{13}$-$C_{14}$ isoparaffins, 22 wt % or more of $C_{12}$ isoparaffins, and 30 wt % or more of $C_{11}$ isoparaffins. This provides an unexpected chain length distribution for a diesel blend component.

Tables 2B, 2C, 2D), and 2E show the weight percentage of isoparaffins of various chain lengths that would be incorporated into a blended product that included 70 vol % of an isoparaffinic blend component (Table 2), 50 vol % (Table 3), or 30 vol % (Table 4), with the balance corresponding to the diesel sample. Again, addition of as little as 10 wt % of an isoparaffinic (or isoolefinic) blend component to a conventional/mineral diesel fraction can result in substantial changes in the $C_{12-}$ branched hydrocarbon content of the resulting blended product.

TABLE 2B

Blend Contributions at 70 wt % IPB

| [wt % isoparaffins] | C8 | C9 | C10 | C11 | C12 | C13/14 | C15/16 | C17/18 | C19/20 | C21+ |
|---|---|---|---|---|---|---|---|---|---|---|
| Diesel | 0.0 | 0.0 | 0.1 | 0.1 | 0.1 | 0.8 | 2.5 | 0.9 | 0.4 | 0.1 |
| IPB-1 | 0.3 | 3.5 | 6.1 | 11.3 | 22.1 | 13.1 | 9.8 | 2.7 | 1.3 | 0.0 |
| IPB-2 | 0.2 | 14.0 | 5.1 | 9.5 | 18.6 | 11.0 | 8.3 | 2.2 | 1.1 | 0.0 |
| IPB-3 | 0.1 | 8.8 | 8.8 | 10.0 | 16.0 | 13.0 | 9.1 | 3.0 | 1.1 | 0.0 |

TABLE 2C

Blend Contributions at 50 wt % IPB

| [wt % isoparaffins] | C8 | C9 | C10 | C11 | C12 | C13/14 | C15/16 | C17/18 | C19/20 | C21+ |
|---|---|---|---|---|---|---|---|---|---|---|
| Diesel | 0.0 | 0.0 | 0.2 | 0.2 | 0.1 | 1.4 | 4.2 | 1.4 | 0.7 | 0.1 |
| IPB-1 | 0.2 | 2.5 | 4.4 | 8.1 | 15.8 | 9.4 | 7.0 | 1.9 | 0.9 | 0.0 |
| IPB-2 | 0.2 | 10.0 | 3.7 | 6.8 | 13.3 | 7.9 | 5.9 | 1.6 | 0.8 | 0.0 |
| IPB-3 | 0.1 | 6.3 | 6.3 | 7.2 | 11.4 | 9.3 | 6.5 | 2.2 | 0.8 | 0.0 |

TABLE 2D

Blend Contributions at 30 wt % IPB

| [wt % isoparaffins] | C8 | C9 | C10 | C11 | C12 | C13/14 | C15/16 | C17/18 | C19/20 | C21+ |
|---|---|---|---|---|---|---|---|---|---|---|
| Diesel | 0.0 | 0.1 | 0.3 | 0.3 | 0.1 | 2.0 | 5.9 | 2.0 | 0.9 | 0.2 |
| IPB-1 | 0.1 | 1.5 | 2.6 | 4.8 | 9.5 | 5.6 | 4.2 | 1.1 | 0.5 | 0.0 |
| IPB-2 | 0.1 | 6.0 | 2.2 | 4.1 | 8.0 | 4.7 | 3.5 | 1.0 | 0.5 | 0.0 |
| IPB-3 | 0.1 | 3.8 | 3.8 | 4.3 | 6.8 | 5.6 | 3.9 | 1.3 | 0.5 | 0.0 |

TABLE 2E

Blend Contributions at 10 wt % IPB

| [wt % isoparaffins] | C8 | C9 | C10 | C11 | C12 | C13/14 | C15/16 | C17/18 | C19/20 | C21+ |
|---|---|---|---|---|---|---|---|---|---|---|
| Diesel | 0.0 | 0.1 | 0.4 | 0.4 | 0.2 | 2.5 | 7.6 | 2.6 | 1.2 | 0.2 |
| IPB-1 | 0.0 | 0.5 | 0.9 | 1.6 | 3.2 | 1.9 | 1.4 | 0.4 | 0.2 | 0.0 |

TABLE 2E-continued

| | Blend Contributions at 10 wt % IPB | | | | | | | | | |
|---|---|---|---|---|---|---|---|---|---|---|
| [wt % isoparaffins] | C8 | C9 | C10 | C11 | C12 | C13/14 | C15/16 | C17/18 | C19/20 | C21+ |
| IPB-2 | 0.0 | 2.0 | 0.7 | 1.4 | 2.7 | 1.6 | 1.2 | 0.3 | 0.2 | 0.0 |
| IPB-3 | 0.0 | 1.3 | 1.3 | 1.4 | 2.3 | 1.9 | 1.3 | 0.4 | 0.2 | 0.0 |

Example 2—Diesel Boiling Range Blends

Using an empirical blending model, the isoparaffinic blend components corresponding to IPB-1 and IPB-2 in Example 1 were used, in combination with two conventional European diesel fuels and two bio-derived fractions, to produce model blended fuels based on the various fractions. As input for the modeling, a series of measurements were made on IPB-1, IPB-2, two different diesel fuels that meet the requirements of EN 590 (the fuels are referred to herein as EPD-1 and EPD-2), the hydrotreated vegetable oil from Example 1, and diesel boiling range fraction based on rapeseed methyl ether (RME). Table 3 shows the measured properties of the various fractions.

TABLE 3

| Measured Values for Diesel Blend Components | | | | | | |
|---|---|---|---|---|---|---|
| Neat Components | IPB-1 | IPB-2 | EPD-1 | EPD-2 | RME | HVO |
| Test methods | — | — | — | — | | |
| Cetane Number, Value | 48.2 | 47 | 54.2 | 51.2 | — | — |
| Density, kg/m³ | 767.0 | 758.0 | 831.8 | 842.9 | 860 | 784.8 |
| Polyaromatic hydrocarbon, Mass % | 0 | 0 | 4.8 | 2.9 | — | — |
| Sulfur, mg/kg | 0 | 0 | 8.8 | 5.9 | 5.0 | 0.0 |
| Flash Point, °C. | 58.5 | 43.3 | 56.5 | 78 | — | — |
| Distillation E250, Vol % | 80 | 90 | 46 | 29 | — | — |
| Distillation E350, Vol % | 100 | 100 | 99 | 97 | — | — |
| Distillation T95, °C. | 284 | 272 | 336 | 343 | — | — |
| Cloud Point, °C. | −80 | −62 | −10 | −5 | — | — |
| Viscosity @ 40°C., cSt | 2.601 | 1.955 | 2.286 | 3.137 | 4.439 | 3.13 |

As shown in Table 3, the IPB-1 and IPB-2 samples have a cetane number between 47-49. This is in contrast to the conventional European diesel samples, which have a cetane number greater than 51. The density of the IPB-1 and IPB-2 samples is also lower than any of the other fractions shown in Table 3. However, the IPB-1 and IPB-2 samples also provide a substantially lower cloud point than the conventional European diesel samples. It is noted that the "Distillation E250" and Distillation E350" rows refer to the volume of a fraction that boils at a temperature of 250° C. or 350° C., respectively.

The measured values in Table 3 were used as the basis for preparing a series of model blends to form potential diesel boiling range fuels. Table 4 shows model blend results for blends formed using 25 wt % of either IPB-1 or IPB-2 in combination with 75 wt % of either EPD-1 or EPD-2.

TABLE 4

| Blends with Conventional Diesel | | | | |
|---|---|---|---|---|
| Neat Components | 25 wt % IPB-1 75 wt % EPD-1 | 25 wt % IPB-1 75 wt % EPD-2 | 25 wt % IPB-2 75 wt % EPD-1 | 25 wt % IPB-2 75 wt % EPD-2 |
| Test methods | — | — | — | — |
| Cetane Number, Value | 51 | 52.7 | 50.7 | 52.4 |
| Density, kg/m³ | 815.6 | 823.9 | 813.4 | 821.7 |
| Polyaromatic hydrocarbon, Mass % | 3.7 | 2.2 | 3.7 | 2.2 |
| Sulfur, mg/kg | 6.7 | 4.5 | 6.7 | 4.5 |
| Flash Point, °C. | 57 | 70 | 52 | 59 |
| Distillation E250, Vol % | 55 | 42 | 55 | 44 |
| Distillation E350, Vol % | 99 | 98 | 99 | 98 |
| Distillation T95, °C. | 331 | 338 | 331 | 338 |
| Cloud Point, °C. | −27 | −24 | −27 | −24 |
| Viscosity @ 40°C., cSt | 2.34 | 2.98 | 2.20 | 2.21 |

As shown in Table 4, all of the modeled blends including 25 wt % of an isoparaffinic blend component resulted in cetane numbers greater than 50. Additionally, each of the resulting blends had a cloud point of −20° C. or less, so that the cloud point of the resulting blend was more than 15° C. lower than the cloud point of the conventional diesel used in the blend.

Table 5 shows a second series of model blends. In this series of model blends, the first two blends include higher percentages of IPB-2 mixed with EPD-2. The second two blends include IPB-1, EPD-2, and either one or both bio-derived fractions shown in Table 3.

TABLE 5

Blends with Higher Content of an Isoparaffinic Blend Component

| Component Concentrations | 30% IPB-1, 70% EPD-2 | 44% IPB-1, 56% EPD-2 | 40% IPB-1, 20% RME, 40% EPD-2 | 33% IPB-1, 20% RME, 10% HVO, 37% EPD-2 |
|---|---|---|---|---|
| Test methods | — | — | — | — |
| Cetane Number, Value | 52.4 | 50.8 | 51.9 | 54.4 |
| Density, kg/m$^3$ | 820 | 800 | 820 | 820 |
| Polyaromatic hydrocarbon, Mass % | 2.1 | 1.3 | 1.2 | 1.1 |
| Sulfur, mg/kg | 4.3 | 2.7 | 2.4 | 2.2 |
| Flash Point, ° C. | 69 | 64 | 69 | 69 |
| Distillation E250, Vol % | 45 | 60 | 43 | 38 |
| Distillation E350, Vol% | 99 | 99 | 97 | 98 |
| Distillation T95, ° C. | 336 | 302 | 343 | 343 |
| Cloud Point, ° C. | −25 | −31 | −27 | −26 |
| Viscosity @ 40° C., cSt | 2.96 | 2.89 | 3.10 | 3.15 |

As shown in Table 5, an isoparaffinic blend component can be added to a conventional diesel in quantities of 30 wt % or more, or 40 wt % or more, while still provide a kinematic viscosity at 40° C. of greater than 2.0 cSt. With regard to the second two blends where bio-derived components are included, it is noted that bio-derived fractions generally have poor cloud point properties. In spite of the addition of 20 wt % or 30 wt % of bio-derived material, the addition of the IPB-1 was still able to reduce the cloud point of the resulting blend to −27° C. or −26° C., so that the cloud point of the resulting blend was more than 15° C. lower than the cloud point of the mineral/conventional fraction included in the blend.

Table 6 shows additional modeled blends where an isoparaffinic blend component is mixed with one or both of the bio-derived fractions shown in Table 3.

TABLE 6

Blends with Bio-Derived Fractions

| Component Concentrations | 54% IPB-1, 46% RME | 50% IPB-1, 50% HVO | 40% IPB-1, 20% RME, 40% HVO |
|---|---|---|---|
| Test methods | — | — | — |
| Cetane Number, Value | 51.1 | 61.9 | 60.4 |
| Density, kg/m$^3$ | 820 | 776 | 797 |
| Polyaromatic hydrocarbon, Mass % | 0 | 0 | 0 |
| Sulfur, mg/kg | 2.5 | 0 | 2 |
| Flash Point, ° C. | 68 | 62 | 66 |
| Distillation E250, Vol % | 42 | 42 | 38 |
| Distillation E350, Vol % | 99 | 100 | 98 |
| Distillation T95, ° C. | 344 | 298 | 341 |
| Cloud Point, ° C. | −31 | −33 | −30 |
| Viscosity @ 40° C., cSt | 3.37 | 2.85 | 3.10 |

As shown in Table 6, due to the higher cetane number of bio-derived fractions, a greater percentage of the isoparaffinic blend component could be added to the blended product while still achieving a cetane number of 51 or higher. This also allowed the resulting blended products to have a cloud point of −30° C. or lower, which is more than 15° C. below the cloud point of either of the bio-derived fractions used for the blends.

Example 3—Marine Fuel Blends

The empirical blending model was also used to generate model blends for incorporating isoparaffinic blend components into various types of marine fuels. Table 7 shows blends of IPB-1 and IPB-2 with a commercially available VLSFO. The measured properties of the VLSFO are also provided for comparison, along with portions of the specification for RMG 380 (the type of VLSFO) from ISO 8217 Table 2.

TABLE 7

Blends with Conventional Fuel Oil

| Component Concentrations | ISO 8217 Table 2 (RMG380) | VLSFO (measured) | 20 wt % IPB-1, 80 wt % VLSFO | 20 wt % IPB-2, 80 wt % VLSFO |
|---|---|---|---|---|
| Density at 15° C. (g/mL) | 0.991 Max | 0.9628* | 0.9236 | 0.9218 |
| KV50 (cSt) | 380.00 Max | 217.3* | 37.9 | 34.1 |
| Net energy content (MJ/kg) | — | 41.49 | 41.95 | 41.96 |
| Estimated Cetane Number | — | 20* | 26 | 25 |
| CCAI | 870 Max | 830 | 814 | 814 |
| Sulfur (ppm m/m) | 5000 Max | 4700* | 3919 | 3927 |
| BMCI | — | 64 | 52.9 | 52.4 |
| TE | — | 40* | 40 | 40 |
| BMCI-TE | — | 20 | 13 | 12 |
| MCR (wt %) | 18.00 Max | 6.16* | 5.1 | 5.1 |
| Pour Point (° C.) | 30 Max | 6.0* | −8.7 | −9.0 |
| Flash Point (° C.) | 60 Min | 119* | 83 | 66 |

*= Measured values for the VLSFO

In Table 7, 20 wt % of an isoparaffinic blend component was blended with the VLSFO. This is believed to be near the compatibility limit for maintaining the heavier aromatic cores in the VLSFO in solution in the resulting blend. Based on the modeled results, addition of an isoparaffinic blend component to the VLSFO provided a variety of advantages for the resulting blended product. First, the estimated cetane number of the blended product increased. Additionally, the pour point of the blended product was lower than the pour point of the VLSFO by 10° C. or more. The isoparaffinic blend components also reduced the sulfur content of the resulting product relative to the sulfur content of the VLSFO. Additionally, the kinematic viscosity at 50° C. was substantially lowered. Finally, a flash point of greater than 60° C. was maintained for the resulting blended product.

Isoparafinnic (and/or isoolefinic) blend components can also be used to make ULSFO fuels or fuel blending components. Table 8 shows modeled examples of blending IPB-1 or IPB-2 with a hydroprocessed vacuum resid fraction. Measured values for the neat hydroprocessed resid (HDP VR) are also shown, along with values for HDME 50, a commercially available ULSFO. Portions of the specification for an RMD8 fuel oil from ISO 8217 Table 2 are also provided.

TABLE 8

Blends with Hydroprocessed Vacuum Resid

| Component Concentrations | ISO 8217 Table 2 (RMD80) | HDP VR | 40 wt % IPB-1, 60 wt % HDP VR | 30 wt % IPB-2, 70 wt % HDP VR | HDME50 (Comp. Example) |
|---|---|---|---|---|---|
| Density at 15° C. (g/mL) | 0.975 Max | 0.9754* | 0.8920 | 0.9102 | 0.9082* |
| KV50 (cSt) | 80.00 Max | 4300* | 24.6 | 50.1 | 33.95* |
| Estimated Cetane Number | — | 43* | 45 | 44 | 66* |
| CCAI | 860 Max | 815 | 790 | 796 | 802* |
| Sulfur (ppm m/m) | 1000 Max | 1360* | 892 | 1020 | 720* |
| BMCI | — | 64.0 | 41.7 | 46.6 | 42.0 |
| TE | — | 0 | 0 | 0 | 0 |
| BMCI-TE | — | 64 | 42 | 47 | 42* |
| MCR (wt %) | 14.00 Max | 8.86* | 5.8 | 6.6 | 0.35* |
| Pour Point (° C.) | 30 Max | 24* | 5.8 | 10.5 | 9* |
| Flash Point (° C.) | 60 Min | 253* | 73 | 61 | 178* |

*= measured values

As shown in Table 8, blending a hydroprocessed vacuum resid with 30 wt % or 40 wt % of an isoparaffinic blend component results in a blended product with substantially lower values for density, kinematic viscosity at 50° C., and pour point. These reductions allow the blended product to have density, KV50, and pour point values that are comparable to the commercially available ULSFO. Also, blending the hydroprocessed resid with the isoparaffinic blend component results in an increase in estimated cetane number. It is noted that higher percentages of the isoparaffinic blend component (up to 50 wt %) can be added to the hydroprocessed vacuum resid. Finally, even at 40 wt % (or more) of the isoparaffinic blend component, the resulting blend has a flash point of 160° C. or higher.

Blends of an isoparaffinic blend component (and/or an isoolefinic blend component) with both renewable fractions and mineral fraction can also be used to form marine fuel oils. Table 9 shows modeled blends of IPB-1 with a higher sulfur content fuel oil (either lightly hydroprocessed or not hydroprocessed). One of the blends corresponds to a 50 wt %/50 wt % mixture of IPB-1 and the fuel oil (FO). The other blend includes 35 wt % IPB-1, 50 wt % of a fatty acid methyl ester fraction, and 15 wt % of the fuel oil. For comparison, measured values for the neat fuel oil are provided, along with some of the specification for an RMA fuel oil according to ISO 8217 Table 2.

TABLE 9

Blends with Fuel Oil and FAME

| Component Concentrations | ISO 8217 Table 2 (RMA) | 100% FO | 35 wt % IPB-1, 50 wt % FAME, 15 wt % FO | 50 wt % IPB-1, 50 wt % FO |
|---|---|---|---|---|
| Density at 15° C. (g/mL) | 0.920 Max | 0.9852* | 0.8566 | 0.8761 |
| KV50 (cSt) | 10.00 Max | 318.5* | 3.5 | 7.47 |
| Net energy content (MJ/kg) | — | ~40.5 | ~39.9 | ~42.2 |
| Estimated Cetane Number | — | ~15 | 19 | 32 |
| CCAI | 850 Max | 848 | 803 | 800 |
| Sulfur (ppm m/m) | 5000 Max | 8200* | 1415 | 4611 |
| BMCI | — | 69.7 | 32.9 | 38.9 |
| TE | — | 11.5* | 12 | 12 |
| BMCI-TE | — | 58 | 21 | 27 |
| MCR (wt %) | 2.50 Max | 10.32* | 1.8 | 5.8 |
| Pour Point (° C.) | 0/6 Max | 9.0* | ~4.5 | ~27.8 |
| Flash Point (° C.) | 60 Min | 129* | 75 | 69 |

*= Measured values

As shown in Table 9, if the isoparaffinic blend component is formed from a renewable source (such as a renewable methanol source), a blend containing up to 85 wt % of renewable content can be used to make a VLSFO fuel. Additionally, as shown in the final modeled blend in Table 9, up to 50 wt % of an isoparaffinic blend component can be mixed with a fuel oil while still maintaining a BMCI value that suggests the blend would be compatible for retaining asphaltenes in solution.

Isoparaffinic blend components (and/or isoolefinic blend components) can also be used for formation of blended products corresponding to marine gas oils or marine gas oil blending components. Table 10 shows modeled blends of 70 wt % of IPB-1 with either 30 wt % of a commercially available MGO or 30 wt % of a fatty acid methyl ester. Measured values for the neat MGO are provided, along with some of the specifications for a DMA marine gas oil under ISO 8217 Table 1.

TABLE 10

Marine Gas Oil Blends

| Component Concentrations | ISO 8217 Table 1 (DMA) | 100% MGO | 70 wt % IPB-1, 30 wt % MGO | 70 wt % IPB-1, 30 wt % FAME |
|---|---|---|---|---|
| Test methods | — | — | — | — |
| Cetane Number, Value | 40 Min | *50 | 48.7 | 53.4 |
| Density, kg/m³ | — | *855 | 793.1 | 801.6 |
| Sulfur, Mass % | 1.00 Max | *0.526 | 0.17 | 1.5 <wppm> |
| Flash Point, ° C. | 43.0 | *91.8 | 62 | 64 |
| Pour Point, ° C. | Report | *9 | -46 | -24 |
| Viscosity @ 40° C., cSt | 2.000 Min 6.000 Max | *5.42 | 3.20 | 3.02 |

*= Measured values

As shown in Table 10, using an isoparaffinic blend component to form an MGO fuel or MGO fuel blending component results in a blended product with kinematic viscosity at 40° C. between 2.0 and 6.0, a flash point of greater than 50° C., or greater than 60° C., and pour point well below 0° C. Additionally, use of an isoparaffinic blend component results in a blended product with a reduced sulfur content (or possibly substantially no sulfur content, if blended with a renewable fraction). The cetane number is reduced relative to the commercially available MGO, but still well above 40. It is noted that the specification for MGO is based on cetane index, rather than cetane number. However, the values of 48.7 and 53.4 shown in Table 10 are sufficiently above 40 that the standard should still be satisfied when measured as cetane index.

Example 4—$^1$H NMR Analysis of Blend Components

The isoparaffinic blend component IPB-1 was formed according to the method described herein, where an isoolefinic blend component was formed by olefin oligomerization. A portion of the isoolefinic blend component was then exposed to hydrotreating conditions to saturate the portion, thus forming the IPB-1 sample. In addition to forming the isoparaffinic blend component, two additional portions of the isoolefinic blend component were exposed to conditions for partial saturation of olefins, resulting in components containing roughly 30 wt % olefins/70 wt % paraffins and 70 wt % olefins/30 wt % paraffins.

The isoolefinic blend component, the isoparaffinic blend component, and the two partially saturated components were characterized using $^1$H NMR to characterize the ratio of $CH_3$ groups to $CH_2$ groups, as determined from the $^1$H NMR results. FIG. 6 shows results from the $^1$H NMR analysis. In FIG. 6, the first column of data corresponds to data for the substantially fully saturated isoparaffinic blend component (IPB-1). The second column and third column show the partially saturated products, while the final column corresponds to data for the isoolefinic blend component, as made from the oligomerization process.

As shown in FIG. 6, the isoolefinic blend component (prior to any saturation) had the highest ratio of $CH_3$ groups to $CH_2$ groups. As saturation increased, the ratio of $CH_3$ groups to $CH_2$ groups went decreased, with the isoparaffinic blend component (IPB-1) having a ratio of $CH_3$ to $CH_2$ groups (as determined based on $^1$H NMR) of 1.18.

For comparison with the values shown in FIG. 6, a variety of other types of fractions were also characterized using $^1$H NMR to determine the ratio of $CH_3$ groups to $CH_2$ groups. Table 11 shows the values that were obtained for these various other types of fractions. Where a range is given, this indicates that multiple different samples were characterized, with the range corresponding to the minimum and maximum values.

TABLE 11

| $CH_3/CH_2$ Ratio as Determined by $^1$H NMR for Other Components | |
|---|---|
| Sample Type | $CH_3$ to $CH_2$ Ratio |
| JET A-1 | 0.75 |
| Diesel | 0.57-1.00 |
| Gas Oil | 0.54 |
| Primarily Isoparaffin Liquid (formed by catalytic isomerization) | 2.50-3.21 |

TABLE 11-continued

| $CH_3/CH_2$ Ratio as Determined by $^1$H NMR for Other Components | |
|---|---|
| Sample Type | $CH_3$ to $CH_2$ Ratio |
| Primarily N-Paraffin Liquid | 0.24-0.33 |
| Naphthenic Liquid (Petroleum Distillate) | 2.35 |
| Fischer-Tropsch Liquid | 0.37 |

As shown in Table 11, liquids with high n-paraffin contents tend to have ratios of $CH_3$ to $CH_2$ that are well below 1.00. Commercial fuel products generally have ratios below 1.00, although a high isoparaffin content/low aromatic content diesel can approach 1.00. Fluids containing high contents of naphthenes have $CH_3$ to $CH_2$ ratios above 2.30. Similarly, fractions with high isoparaffin content, where the isoparaffin content is formed by catalytic isomerization, have $CH_3$ to $CH_2$ ratios above 2.30.

Example 5—Quaternary Carbon Content

A sample of IPB-1 was separated using a gas chromatograph to form a $C_{12}$ fraction. The resulting $C_{12}$ fraction was analyzed using $^{13}$C NMR to determine the content of quaternary carbons in the sample. For comparison, $C_{12}$ fractions were also formed from two other mineral sources after exposing the sources to deep catalytic isomerization. Table 12 shows the results from analysis of the $C_{12}$ fractions.

TABLE 12

| $^{13}$C NMR Analysis of $C_{12}$ Fractions | | | |
|---|---|---|---|
| | $C_{12}$ Comparative #1 | $C_{12}$ Comparative #2 | $C_{12}$ from IPB-1 |
| Average Carbon Number (by GC) | 11.95 | 11.88 | 12.0 |
| Naphthenic Content | 8 | 8 | 0 |
| Number of Branches per Molecule | 2.97 | 2.39 | 2.78 |
| Quaternaries (% of total number of carbons) | 1.64 | 1.77 | 1.35 |

As shown in Table 12, the quaternary carbon content of the $C_{12}$ fraction was substantially lower than the other fractions. For both comparative samples, the $C_{12}$ fraction had a quaternary carbon content of greater than 1.60% relative to the total number of carbons in the sample, while the $C_{12}$ fraction from the isoparaffinic blend component has a quaternary carbon content of 1.60% or less, or 1.50% or less, or 1.40% or less, such as down to 1.20% or possibly still lower.

Example 6—Carbon Chain Length Distribution in Isoparaffinic Blend Component

One of the unusual features of the isoparaffinic blend component as described herein is that the isoparaffinic blend component can contain a substantial portion of $C_{17+}$ hydrocarbons while still forming a blend with a final boiling point of 300° C. or less, as measured according to ASTM D86. To illustrate this, several different samples of isoparaffinic blend component were formed using the synthesis methods described herein. Table 13 shows the volume percentage of the hydrocarbon chain lengths in the resulting isoparaffinic blend components. The samples are referred to as IPB 1, 2, and 3 (for Isoparaffinic Blend Component). For comparison, the hydrocarbon chain length distribution in a representative JET A-1 sample is also shown.

TABLE 13

Hydrocarbon Chain Length Distribution

[vol %]

| | C8 | C9 | C10 | C11 | C12 | C13/ 14 | C15/ 16 | C17/ 18 | C19/ 20 |
|---|---|---|---|---|---|---|---|---|---|
| JET A-1 | 1.7 | 3.2 | 7.3 | 12.7 | 15.2 | 27.4 | 13.4 | 1.5 | 0.0 |
| IPB 1 | 0.3 | 3.8 | 6.6 | 12.3 | 24.3 | 14.3 | 10.7 | 2.9 | 1.4 |
| IPB 2 | 0.2 | 15.1 | 5.5 | 10.3 | 20.1 | 11.9 | 8.9 | 2.4 | 1.1 |
| IPB 3 | 0.2 | 9.6 | 9.6 | 10.9 | 17.4 | 14.2 | 9.9 | 3.3 | 1.2 |

As shown in Table 13, the representative JET A-1 sample includes less than 2.0 vol % of $C_{17}$-$C_{18}$ components, and no $C_{19}$ or $C_{20}$ components. By contrast, each of the isoparaffinic blend components include more than 3.0 vol % of $C_{17}$-$C_{18}$ hydrocarbons, as well as more than 4.5 vol % of $C_{17+}$ hydrocarbons.

The increased concentration of $C_{17+}$ hydrocarbons in the isoparaffinic blend components can result in a corresponding increase in $C_{17+}$ hydrocarbons in blends that include a portion of an isoparaffinic blend component. Tables 14-16 show the volume percentage of hydrocarbons of various chain lengths that would be incorporated into a blended product that included 70 vol % of an isoparaffinic blend component (Table 14), 50 vol % (Table 15), or 30 vol % (Table 16).

TABLE 14

Contribution to Blend at 70 vol %

[vol %]

| | C8 | C9 | C10 | C11 | C12 | C13/ 14 | C15/ 16 | C17/ 18 | C19/ 20 |
|---|---|---|---|---|---|---|---|---|---|
| JET A-1 | 1.2 | 2.3 | 5.1 | 8.9 | 10.6 | 19.2 | 9.4 | 1.0 | 0.0 |
| IPB 1 | 0.2 | 2.7 | 4.7 | 8.6 | 17.0 | 10.0 | 7.5 | 2.1 | 1.0 |
| IPB 2 | 0.2 | 10.6 | 3.9 | 7.2 | 14.1 | 8.3 | 6.2 | 1.7 | 0.8 |
| IPB 3 | 0.1 | 6.7 | 6.7 | 7.7 | 12.2 | 10.0 | 7.0 | 2.3 | 0.9 |

TABLE 15

Contribution to Blend at 50 vol %

[vol %]

| | C8 | C9 | C10 | C11 | C12 | C13/ 14 | C15/ 16 | C17/ 18 | C19/ 20 |
|---|---|---|---|---|---|---|---|---|---|
| JET A-1 | 0.8 | 1.6 | 3.6 | 6.3 | 7.6 | 13.7 | 6.7 | 0.7 | 0.0 |
| IPB 1 | 0.1 | 1.9 | 3.3 | 6.2 | 12.1 | 7.2 | 5.4 | 1.5 | 0.7 |
| IPB 2 | 0.1 | 7.6 | 2.8 | 5.1 | 10.1 | 5.9 | 4.5 | 1.2 | 0.6 |
| IPB 3 | 0.1 | 4.8 | 4.8 | 5.5 | 8.7 | 7.1 | 5.0 | 1.6 | 0.6 |

TABLE 16

Contribution to Blend at 30 vol %

[vol %]

| | C8 | C9 | C10 | C11 | C12 | C13/ 14 | C15/ 16 | C17/ 18 | C19/ 20 |
|---|---|---|---|---|---|---|---|---|---|
| JET A-1 | 0.5 | 1.0 | 2.2 | 3.8 | 4.5 | 8.2 | 4.0 | 0.4 | 0.0 |
| IPB 1 | 0.1 | 1.1 | 2.0 | 3.7 | 7.3 | 4.3 | 3.2 | 0.9 | 0.4 |
| IPB 2 | 0.1 | 4.5 | 1.7 | 3.1 | 6.0 | 3.6 | 2.7 | 0.7 | 0.3 |
| IPB 3 | 0.0 | 2.9 | 2.9 | 3.3 | 5.2 | 4.3 | 3.0 | 1.0 | 0.4 |

As shown in Tables 14-16, blends including 70 vol % of an isoparaffinic blend component can include 1.6 vol % or more of $C_{17}$-$C_{18}$ hydrocarbons, or 2.0 vol % or more, such as up to 2.3 vol %. For a 50% blend, the isoparaffinic blend component can contribute 1.2 vol % or more of $C_{17}$-$C_{18}$ hydrocarbons, such as up to 1.6 vol %. Based on a typical $C_{17}$-$C_{18}$ content in a conventional jet fuel of roughly 1.5 vol %, it is clear that an isoparaffinic blend component as described herein can allow for incorporation of a higher volume percentage of $C_{17}$-$C_{18}$ hydrocarbons into a potential blended jet fuel product.

Example 7—Blends with Conventional Jet Fuels

The isoparaffinic blend components corresponding to IPB 1 and IPB 2 in Example 6 were used in combination with conventional jet fuels (JET A-1 or JP-5) to form blended jet boiling range products. Even for blends with 50 vol % or more of an isoparaffinic blend component, or 70 vol % or more, the resulting blended jet boiling range products still satisfied the specification for the corresponding type of jet fuel.

FIG. 7 shows results from characterization of a conventional JET A-1 sample, a sample of IPB 1, a blend formed from 30 vol % IPB 1 and 70 vol % JET A-1, and a blend formed from 70 vol % IPB 1 and 30 vol % JET A-1. As shown in FIG. 7, IPB 1 alone does not satisfy all of the standard requirements for a JET A-1 jet fuel. However, blending 70 vol % of IPB 1 with 30 vol % of a conventional JET A-1 resulted in a blended product that satisfied all of the JET A-1 requirements shown in FIG. 7, with the exception of electrical conductivity. However, the conductivity of a potential jet fuel product can be readily raised to meet the required standard using conventional additives.

As explained in Example 6, the blend containing 70 vol % IPB 1 included at least 2.0 vol % of $C_{17}$-$C_{18}$ hydrocarbons even without considering the contributions from the JET A-1. The blend including 70 vol % IPB 1 also provided a higher JFTOT breakpoint temperature and a higher smoke point. In combination with the generally beneficial cold flow properties of an isoparaffinic blend component, FIG. 7 shows the value of an isoparaffinic blend component as described herein for potentially returning off-specification jet fuel samples back to specification.

A similar characterization was performed on a JET A-1 sample, IPB 2, a blend of 30 vol % IPB 2 with 70 vol % JET A-1, and a blend of 70 vol % IPB 2 with 30 vol % JET A-1. The results from characterization of these blend products are shown in FIG. 8. Similar to FIG. 7, blending of 50 vol % or more, or 70 vol % or more of an isoparaffinic blend component with a conventional jet fuel sample results in a blended product that can still satisfy all of the required standards that are shown in FIG. 8.

Example 8—Isoparaffinic Blend Component as Lubricity Improver

It has been discovered that in aspects where the resulting blended product includes at least 10 vol % of a mineral jet boiling range fraction and 40 vol % or more (or 50 vol % or more) of an isoparaffinic blend component, the resulting blended product can have an unexpectedly improved lubricity. Lubricity can be measured based on wear scar diameter as determined according to ASTM D5001. For example, such a blended product can include 10 vol %-50 vol % of a mineral jet boiling range fraction, or 10 vol % to 60 vol %, or 20 vol % to 50 vol %, or 20 vol % to 60 vol %. Such a blended component can also include 40 vol % to 90 vol % of an isoparaffinic blend component, or 50 vol % to 90 vol %, or 40 vol % to 80 vol %, or 50 vol % to 80 vol %.

The unexpected nature of the lubricity improvement when adding 50 vol % or more of an isoparaffinic blend component to a mineral jet boiling range fraction can be understood by comparing the lubricity behavior of the blends shown in Table 17. Table 17 shows results from testing various jet boiling range fractions under the method of ASTM D5001 to determine a wear scar diameter. In Table 17, the first two samples correspond to neat samples of JET A-1 and JP-5. The remaining samples are blends of an isoparaffinic blend component (either IPB-1 or IPB-2) with the JET A-1 or JP-5. Conventionally, it would be expected that adding a highly paraffinic blend component to a mineral jet boiling range fraction would result in poorer lubricity performance. For comparison, it is noted that some diesel fuel standards have a maximum wear scar diameter under the ASTM D5001 of 0.85 mm or less.

TABLE 17

Measured Lubricity Values for Jet Boiling Range Fractions

| Fuel | Wear Scar Diameter | Test Method |
|---|---|---|
| 100% JET A-1 | 0.72 mm | D5001 |
| 100% JP-5 | 0.62 mm | D5001 |
| 30% IPB-1/70% JET A-1 | 0.67 mm | D5001 |
| 70% IPB-1/30% JET A-1 | 0.52 mm | D5001 |
| 30% IPB-2/70% JET A-1 | 0.68 mm | D5001 |
| 70% IPB-2/30% JET A-1 | 0.53 mm | D5001 |
| 25% IPB-1/75% JP-5 | 0.63 mm | D5001 |
| 50% IPB-1/50% JP-5 | 0.60 mm | D5001 |

As shown in Table 17, at blend amounts of 30 vol % of either IPB-1 or IPB-2 with JET A-1, if a linear weighted average model is used to describe the wear scar diameter result for the blends, the linear weighted average model predicts that IPB-1 or IPB-2 alone would have a wear scar diameter of roughly 0.60 mm. By contrast, for the blends including 50 wt % or more of IPB-1 or IPB-2, a linear weighted average model predicts a wear scar diameter below 0.60 mm. It is further noted that for blends of higher amounts of an isoparaffinic blend component with the JET A-1 sample (such as 50 vol % or more of an isoparaffinic blend component), the wear scar diameter for the blended composition is reduced by 10% or more relative to the wear scar diameter for the mineral jet boiling range fraction alone.

Similarly, for the blend of 25 vol % IPB-1 with JP-5, a linear weighted average model predicts that IPB-1 would have a wear scar diameter of around 0.63 mm. In fact, addition of IPB-1 appears to increase the wear scar diameter when mixed with JP-5, in accordance with the conventional expectation. However, increasing the amount of IPB-1 in this blend to 50 wt % results in a reduction of wear scar diameter relative to neat JP-5, with a predicted wear scar diameter for neat IPB-1 of roughly 0.58 mm.

Based on Table 17, a synergy is observed for blends at 50% of an isoparaffinic blend component or greater, where an unexpected reduction in wear scar diameter is achieved at larger quantities of isoparaffinic blend component in a blend.

Example 9—$^1$H NMR Analysis of Blend Components

The isoparaffinic blend component IPB-1 was formed according to the method described herein, where an isoolefinic blend component was formed by olefin oligomerization. A portion of the isoolefinic blend component was then exposed to hydrotreating conditions to saturate the portion, thus forming the IPB-1 sample. In addition to forming the isoparaffinic blend component, two additional portions of the isoolefinic blend component were exposed to conditions for partial saturation of olefins, resulting in components containing roughly 30 wt % olefins/70 wt % paraffins and 70 wt % olefins/30 wt % paraffins.

The isoolefinic blend component, the isoparaffinic blend component, and the two partially saturated components were characterized using $^1$H NMR to characterize the ratio of $CH_3$ groups to $CH_2$ groups, as determined from the $^1$H NMR results. FIG. 9 shows results from the $^1$H NMR analysis. In FIG. 9, the first column of data corresponds to data for the substantially fully saturated isoparaffinic blend component (IPB-1). The second column and third column show the partially saturated products, while the final column corresponds to data for the isoolefinic blend component, as made from the oligomerization process.

As shown in FIG. 9, the isoolefinic blend component (prior to any saturation) had the highest ratio of $CH_3$ groups to $CH_2$ groups. As saturation increased, the ratio of $CH_3$ groups to $CH_2$ groups went decreased, with the isoparaffinic blend component (IPB-1) having a ratio of $CH_3$ to $CH_2$ groups (as determined based on $^1$H NMR) of 1.18.

For comparison with the values shown in FIG. 9, a variety of other types of fractions were also characterized using $^1$H NMR to determine the ratio of $CH_3$ groups to $CH_2$ groups. Table 18 shows the values that were obtained for these various other types of fractions. Where a range is given, this indicates that multiple different samples were characterized, with the range corresponding to the minimum and maximum values.

TABLE 18

$CH_3/CH_2$ Ratio as Determined by $^1$H NMR for Other Components

| Sample Type | $CH_3$ to $CH_2$ Ratio |
|---|---|
| JET A-1 | 0.75 |
| Diesel | 0.57-1.00 |
| Gas Oil | 0.54 |
| Primarily Isoparaffin Liquid (formed by catalytic isomerization) | 2.50-3.21 |
| Primarily N-Paraffin Liquid | 0.24-0.33 |
| Naphthenic Liquid (Petroleum Distillate) | 2.35 |
| Fischer-Tropsch Liquid | 0.37 |

As shown in Table 18, liquids with high n-paraffin contents tend to have ratios of $CH_3$ to $CH_2$ that are well below 1.00. Commercial fuel products generally have ratios below 1.00, although a high isoparaffin content/low aromatic content diesel can approach 1.00. Fluids containing high contents of naphthenes have $CH_3$ to $CH_2$ ratios above 2.30. Similarly, fractions with high isoparaffin content, where the isoparaffin content is formed by catalytic isomerization, have $CH_3$ to $CH_2$ ratios above 2.30.

Example 10—Quaternary Carbon Content

A sample of IPB-1 was separated using a gas chromatograph to form a $C_{12}$ fraction. The resulting $C_{12}$ fraction was analyzed using $^{13}C$ NMR to determine the content of quaternary carbons in the sample. For comparison, $C_{12}$ fractions were also formed from two other mineral sources after exposing the sources to deep catalytic isomerization. Table 19 shows the results from analysis of the $C_{12}$ fractions.

TABLE 19

$^{13}C$ NMR Analysis of $C_{12}$ Fractions

|  | $C_{12}$ Comparative #1 | $C_{12}$ Comparative #2 | $C_{12}$ from IPB-1 |
|---|---|---|---|
| Average Carbon Number (by GC) | 11.95 | 11.88 | 12.0 |
| Naphthenic Content | 8 | 8 | 0 |
| Number of Branches per Molecule | 2.97 | 2.39 | 2.78 |
| Quaternaries (% of total number of carbons) | 1.64 | 1.77 | 1.35 |

As shown in Table 19, the quaternary carbon content of the $C_{12}$ fraction was substantially lower than the other fractions. For both comparative samples, the $C_{12}$ fraction had a quaternary carbon content of greater than 1.60% relative to the total number of carbons in the sample, while the $C_{12}$ fraction from the isoparaffinic blend component has a quaternary carbon content of 1.60% or less, or 1.50% or less, or 1.40% or less, such as down to 1.20% or possibly still lower.

Therefore, the present invention is well adapted to attain the ends and advantages mentioned as well as those that are inherent therein. The particular examples and configurations disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative examples disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

What is claimed is:

1. A method for producing an isoolefinic stream comprising:
   oligomerizing an ethylene stream to a C4+ olefin stream in a first olefin oligomerization unit comprising a reactor and a lights removal column, wherein the C4+ olefin stream contains no greater than 10 wt % of methane, ethylene, and ethane combined; and wherein the ethylene stream contains at least 50 wt % ethylene, at least 2000 wppm ethane, no greater than 1000 wppm of methane, and no greater than 20 wppm each of carbon monoxide and hydrogen; and
   oligomerizing the C4+ olefin stream and a propylene/C4+ olefin stream in a second oligomerization unit to produce the isoolefinic stream.

2. The method of claim 1, wherein the C4+ olefin stream contains no greater than 5 wt % of methane, ethylene, and ethane combined.

3. The method of claim 1, wherein the C4+ olefin stream contains no greater than 2000 wppm of methane, ethylene, and ethane combined.

4. The method of claim 1, wherein the ethylene stream contains at least 50 wt % ethylene, at least 2000 wppm ethane, no greater than 1000 wppm of methane, and no greater than 5 wppm each of carbon monoxide and hydrogen.

5. The method of claim 1, wherein the ethylene stream contains at least 50 wt % ethylene, at least 2000 wppm ethane, no greater than 1000 wppm of methane, and no greater than 1 wppm each of carbon monoxide and hydrogen.

6. The method of claim 1 further comprising:
   hydroprocessing the isoolefinic stream with hydrogen as treat gas to produce an isoparaffinic stream having no greater than 10 wt % olefin content.

7. The method of claim 1 further comprising:
   combining the C4+ olefin stream and the propylene/C4+ olefin stream before the second oligomerization.

8. The method of claim 1, wherein the first oligomerization unit utilizes a homogeneous catalyst, and wherein the second oligomerization unit utilize a heterogeneous catalyst.

9. The method of claim 1 further comprising:
   recycling a portion of the C4+ olefin stream that is not oligomerized during the second oligomerization back to the second oligomerization again.

10. A method comprising:
    converting an oxygenate to olefins to produce a raw olefin stream;
    wherein the raw olefin stream comprises ethylene, propylene, and C4+ olefins, wherein at least 10 wt % of all olefins in the raw olefin stream are ethylene, and further containing at least 1000 wppm of each methane and ethane, and at least 100 wppm of each carbon monoxide and hydrogen;
    separating the raw olefin stream to remove hydrogen, carbon monoxide, propylene and C4+ olefins from the raw olefin stream, and produce an ethylene stream containing at least 50 wt % ethylene, at least 2000 wppm ethane, no greater than 1000 wppm of methane, and no greater than 20 wppm each of carbon monoxide and hydrogen, wherein at least 95 wt % of all the ethylene in the raw olefin stream is recovered in the ethylene stream;
    oligomerizing at least a portion of the ethylene stream in a first oligomerization unit to convert at least 90% of the ethylene contained in the ethylene stream to a C4+ olefin stream containing no greater than 10 wt % of methane, ethylene, and ethane combined; and oligomerizing the C4+ olefin stream and a propylene/C4+ olefin stream in a second oligomerization unit to produce the isoolefinic stream.

11. The method of claim 10, wherein the C4+ olefin stream contains no greater than 5 wt % of methane, ethylene, and ethane combined.

12. The method of claim 10, wherein the C4+ olefin stream contains no greater than 2000 wppm of methane, ethylene, and ethane combined.

13. The method of claim 10, wherein the ethylene stream contains at least 50 wt % ethylene, at least 2000 wppm ethane, no greater than 1000 wppm of methane, and no greater than 5 wppm each of carbon monoxide and hydrogen.

14. The method of claim 10, wherein the ethylene stream contains at least 50 wt % ethylene, at least 2000 wppm ethane, no greater than 1000 wppm of methane, and no greater than 1 wppm each of carbon monoxide and hydrogen.

15. The method of claim 10, wherein the ethylene stream contains at least 90% of the ethane present in the raw olefin stream.

16. The method of claim 10, wherein the oxygenate is converted to olefins using a silicoaluminophosphate catalyst, an aluminosilicate catalyst, or steam cracking.

17. The method of claim 10, wherein the first oligomerization unit utilizes a homogeneous catalyst, and wherein the second oligomerization unit utilizes a heterogeneous catalyst.

18. The method of claim 10, wherein the hydrogen and carbon monoxide are separated from the propylene and C4+ olefins when separated from the raw olefin stream.

19. A method for producing an isoolefinic stream comprising:

providing a raw olefin stream comprising ethylene, propylene and C4+ olefins, wherein at least 10 wt % of all olefins in the raw olefin stream are ethylene, and further containing at least 1000 wppm of each methane and ethane, and at least 100 wppm of each carbon monoxide and hydrogen;

separating the raw olefin stream to remove hydrogen, carbon monoxide, propylene and C4+ olefins from the raw olefin stream, and produce an ethylene stream containing at least 50 wt % ethylene, at least 2000 wppm ethane, no greater than 1000 wppm of methane, and no greater than 20 wppm each of carbon monoxide and hydrogen, wherein at least 95 wt % of all the ethylene in the raw olefin stream is recovered in the ethylene stream;

oligomerizing at least a portion of the ethylene stream in a first olefin oligomerization unit comprising a reactor and a lights removal column, to convert in a single pass through the reactor at least 90% of the ethylene contained in the ethylene stream to a C4+ olefin stream containing no greater than 10 wt % of methane, ethylene, and ethane combined; and oligomerizing at least a portion of each of the propylene and the C4+ olefins removed from the raw olefins stream, and at least a portion of the C4+ stream in a second olefin oligomerization unit comprising a reactor and a fractionation column to produce the isoolefinic stream.

20. The method of claim 19, wherein the separating of the raw olefin stream comprises:

separating propylene and C4+ from the raw olefin stream in a deethanizer distillation column; and separating methane, hydrogen, and carbon monoxide from the raw olefin stream in a demethanizer distillation column to produce the ethylene stream.

* * * * *